US010260049B2

(12) United States Patent
Kim et al.

(10) Patent No.: US 10,260,049 B2
(45) Date of Patent: Apr. 16, 2019

(54) ATTENUATED REOVIRUS

(75) Inventors: Manbok Kim, Calgary (CA); Randal N. Johnston, Calgary (CA)

(73) Assignee: VIROCURE, INC., Seoul (KR)

( * ) Notice: Subject to any disclaimer, the term of this patent is extended or adjusted under 35 U.S.C. 154(b) by 777 days.

(21) Appl. No.: 11/997,537

(22) PCT Filed: Jul. 31, 2006

(86) PCT No.: PCT/IB2006/004149
§ 371 (c)(1),
(2), (4) Date: Oct. 14, 2008

(87) PCT Pub. No.: WO2007/099401
PCT Pub. Date: Sep. 7, 2007

(65) Prior Publication Data
US 2009/0214479 A1 Aug. 27, 2009

Related U.S. Application Data

(60) Provisional application No. 60/704,604, filed on Aug. 1, 2005.

(51) Int. Cl.
*C12N 7/04* (2006.01)
*A61K 35/765* (2015.01)
*C12N 7/00* (2006.01)
C12N 7/08 (2006.01)
C12N 15/86 (2006.01)

(52) U.S. Cl.
CPC .............. *C12N 7/00* (2013.01); *A61K 35/765* (2013.01); *C12N 2720/12232* (2013.01); *C12N 2720/12264* (2013.01)

(58) Field of Classification Search
CPC .................. A61K 35/765; C12N 7/08; C12N 2720/12021; C12N 2720/12033; C12N 2720/12064
See application file for complete search history.

(56) References Cited

U.S. PATENT DOCUMENTS

| | | | |
|---|---|---|---|
| 5,210,272 A | 5/1993 | Palmer | |
| 5,344,939 A | 9/1994 | Palmer | |
| 6,110,461 A | 8/2000 | Lee et al. | 424/93.6 |
| 6,136,307 A | 10/2000 | Lee et al. | 424/93.6 |
| 6,261,555 B1 | 7/2001 | Lee et al. | 424/93.6 |
| 6,344,195 B1 | 2/2002 | Lee et al. | 424/93.6 |
| 6,455,038 B1 | 9/2002 | Lee et al. | 424/93.6 |
| 6,528,305 B2 | 3/2003 | Thompson et al. | 435/325 |
| 6,565,831 B1 | 5/2003 | Coffey et al. | 424/39.2 |
| 6,576,234 B2 | 6/2003 | Lee et al. | 424/93.6 |
| 6,596,268 B1 | 7/2003 | Coffey et al. | 424/93.2 |
| 6,605,589 B1 | 8/2003 | Uckun et al. | |
| 6,649,157 B2 | 11/2003 | Coffey et al. | 424/93.1 |
| 6,703,232 B2 | 3/2004 | Thompson et al. | 435/235.1 |
| 6,808,916 B2 | 10/2004 | Coffey et al. | 435/238 |
| 6,811,775 B2 | 11/2004 | Lee et al. | 424/93.6 |
| 6,994,858 B2 | 2/2006 | Morris et al. | |
| 7,014,847 B2 | 3/2006 | Coffey et al. | 424/93.1 |
| 7,049,127 B2 | 5/2006 | Thompson et al. | 435/235.1 |
| 7,122,182 B2 | 10/2006 | Groene et al. | 435/325 |
| 7,163,678 B2 | 1/2007 | Norman et al. | 424/93.1 |
| 7,186,542 B2 | 3/2007 | Coffey et al. | 435/239 |
| 7,192,580 B2 | 3/2007 | Atkins et al. | 424/215.1 |
| 7,264,798 B2 | 9/2007 | Coffey et al. | 424/93.6 |
| 7,270,812 B2 | 9/2007 | Shino et al. | 424/93.2 |
| 7,300,650 B2 | 11/2007 | Lee et al. | 424/93.2 |
| 7,431,932 B2 | 10/2008 | Morris et al. | |
| 7,708,987 B2 | 5/2010 | Coffey et al. | |
| 2001/0048919 A1 | 12/2001 | Morris et al. | |
| 2002/0037543 A1 | 3/2002 | Atkins et al. | 435/7.23 |
| 2002/0168344 A1 | 11/2002 | Coffey et al. | 424/93.2 |
| 2003/0044384 A1 | 3/2003 | Roberts et al. | 424/93.2 |
| 2003/0165465 A1 | 9/2003 | Roberts et al. | |
| 2004/0005329 A1 | 1/2004 | Uckun et al. | |
| 2004/0115170 A1 | 6/2004 | Brown et al. | 424/93.2 |
| 2004/0126869 A1 | 7/2004 | Thompson et al. | 435/235.1 |
| 2004/0146491 A1 | 7/2004 | Norman et al. | 424/93.6 |
| 2004/0202663 A1 | 10/2004 | Hu et al. | 424/155.1 |
| 2004/0265271 A1 | 12/2004 | Lee et al. | 424/93.2 |
| 2005/0019308 A1 | 1/2005 | Norman et al. | 424/93.2 |

(Continued)

FOREIGN PATENT DOCUMENTS

| | | |
|---|---|---|
| CA | 2411397 | 11/2002 |
| CA | 2422245 | 3/2003 |

(Continued)

OTHER PUBLICATIONS

Duby et al, Identification of attenuating mutations on the reovirus type 3 S1 double-stranded RNA segment with a rapid sequencing technique. JVi 1986, pp. 64-67.*
Hoyt et al, Nonstructural Protein _1s Is a Determinant of Reovirus Virulence and Influences the Kinetics and Severity of Apoptosis Induction in the Heart and Central Nervous System, Journal of Virology, Mar. 2005, p. 2743-2753.*
International Preliminary Report on Patentability, issued in International Application No. PCT/IB2006/004149, dated Feb. 5, 2008.
International Search Report and Written Opinion, issued in International Application No. PCT/IB2006/004149, dated Dec. 13, 2007.
Alain et al., "The oncolytic effect in vivo of reovirus on tumor cells that have survived reovirus cell killing in vitro," *British J. Cancer*, 95:1020-1027, 2006.

(Continued)

*Primary Examiner* — Maria Marvich
(74) *Attorney, Agent, or Firm* — Vorys, Sater, Seymour & Pease LLP; Mih Suhn Koh

(57) ABSTRACT

Compositions and methods are provided that relate to an attenuated reovirus exhibiting oncolytic activity toward cancer cells while displaying reduced lytic activity toward non-malignant cells. Exemplified is an attenuated human reovirus derived from persistently infected fibrosarcoma cells that lacks wild-type reovirus S1 and S4 genes and consequently lacks a detectable reoviral outer capsid σ1 protein and expresses a mutated reoviral outer capsid σ3 protein.

8 Claims, 18 Drawing Sheets

Specification includes a Sequence Listing.

(56) References Cited

U.S. PATENT DOCUMENTS

| | | | |
|---|---|---|---|
| 2005/0026289 A1 | 2/2005 | Morris et al. | 435/456 |
| 2005/0063954 A1 | 3/2005 | Lee et al. | 424/93.2 |
| 2005/0123513 A1 | 6/2005 | Lee et al. | 424/93.2 |
| 2005/0214266 A1 | 9/2005 | Morris et al. | 424/93.21 |
| 2006/0029598 A1 | 2/2006 | Morris et al. | 424/133.1 |
| 2006/0073166 A1 | 4/2006 | Coffey et al. | 424/204.1 |
| 2006/0088869 A1 | 4/2006 | Coffey | 435/6 |
| 2009/0104162 A1 | 4/2009 | Kim et al. | |
| 2017/0049824 A1 | 2/2017 | Nordrum et al. | |
| 2017/0049829 A1 | 2/2017 | Kim et al. | |

FOREIGN PATENT DOCUMENTS

| | | |
|---|---|---|
| CA | 2434995 | 7/2003 |
| CA | 2435967 | 7/2003 |
| CA | 2436196 | 7/2003 |
| CA | 2374388 | 7/2005 |
| WO | WO 1999/008692 | 2/1999 |
| WO | WO 1999/018799 | 4/1999 |
| WO | WO 2000/050051 | 8/2000 |
| WO | WO 2000/062735 | 10/2000 |
| WO | WO 2001/019380 | 3/2001 |
| WO | WO 2001/035970 | 5/2001 |
| WO | WO 2001/083711 | 11/2001 |
| WO | WO 2002/000233 | 1/2002 |
| WO | WO 2002/011742 | 2/2002 |
| WO | WO 2002/012435 | 2/2002 |
| WO | WO 2002/039117 | 5/2002 |
| WO | WO 2002/040042 | 5/2002 |
| WO | WO 2002/043647 | 6/2002 |
| WO | WO 2002/050304 | 6/2002 |
| WO | WO 2002/066040 | 8/2002 |
| WO | WO 2002/074940 | 9/2002 |
| WO | WO 2002/091997 | 11/2002 |
| WO | WO 2003/080083 | 10/2003 |
| WO | WO 2003/093463 | 11/2003 |
| WO | WO 2003/094938 | 11/2003 |
| WO | WO 2003/094939 | 11/2003 |
| WO | WO 2004/003562 | 1/2004 |
| WO | WO 2004/066947 | 8/2004 |
| WO | WO 2005/002607 | 1/2005 |
| WO | WO 2005/014017 | 2/2005 |
| WO | WO 2001/083710 | 1/2008 |
| WO | WO 2008/112911 | 9/2008 |

OTHER PUBLICATIONS

Kim et al., "Reovirus and tumor oncolysis," *J. Microbiol.*, 45:187-192, 2007.
Wilson et al., "Persistent reovirus infections of L cells select sigma-1 that alter oligomer stability," *J. Virol.*, 70:6598-6606, 1996.
Ahmed et al., "Role of the S4 gene in the establishment of persistent reovirus infection in L cells," *Cell*, 28 (3):605-612, 1982.
Baer et al., "Mutations in reovirus outer-capsid protein sigma3 selected during persistent infections of L cells confer resistance to protease inhibitor E64," *J. Virol.*, 71 (7):4921-4928, 1997.
Baer et al., "Mutant cells selected during persistent reovirus infection do not express mature cathespin L and do not support reovirus disassembly," *Journal of Virology*, 73 (11):9532-9543, 1999.
Brown et al., "Bioengineering the oncolytic potential of reovirus," *Gene Therapy*, 8 (1):s7, 2001.
Campbell et al., "Junctional Adhesion Molecule A Serves as a Receptor for Prototype and Field-Isolate Strains of Mammalian Reovirus," *J. of Virol.*, 19 (13): 7967-7978, 2005.
Chandran et al., "Complete in vitro assembly of the reovirus outer capsid produces highly infectious particles suitable for genetic studies of the receptor-binding protein," *J. Virol.*, 75 (1): 5335-5342, 2001.
Chandran et al., "In vitro recoating of reovirus cores with baculovirus-expressed outer-capsid proteins mu1 and sigma3," *J. Virol.*, 73: 3941, 1999.

Chapell et al., "Identification of carbohydrate-binding domains in the attachment proteins of type 1 and type 3 reoviruses," *J. Virol.*, 74 (18):8472-8479, 2000.
Chapell et al., "Mutations in type 3 reovirus that determine binding to sialic acid are contained in the fibrous tail domain of viral attachment protein sigma1," *J. Virol.*, 71 (3): 1834-1841, 1997.
Chiocca, "Oncolytic viruses," *Nature Reviews Cancer*, 2 (12):938-950, 2002.
Clarke et al., "Mechanisms of reovirus-induced cell death and tissue host-cell signaling and transcription factor activation," *Viral Immunology*, 18 (1):89-115, 2005.
Clarke et al., "Reovirus infection activates JNK and the JNK-dependent transcription factor c-jun," *Journal of Virology*, 75 (23):11275-11283, 2001.
Coffey et al., "Reovirus therapy of tumors with activated Ras pathway," *Science*, 282 (5392): 1332-1334, 1998.
Connolly et al., "Reovirus binding to cell surface sialic acid potentiates virus-induced apoptosis," J. Virol., 75 (9):4029-4039, 2001.
Dermody et al., "Eradication of persistent reovirus infection from a B-cell hybridoma," Virol., 212 (1):272-276, 1995.
Dermody et al., "Sequence Diversity in S1 Genes and S1 Translation Products of 11 Serotype 3 Reovirus Strains," *J. Virol.*, 64 (10): 4842-4850, 1990.
Dermody et al., "Cells and viruses with mutations affecting viral entry are selected during persistent infections of L cells with mammalian reoviruses," *J. Virol.*, 67 (4):2055-2063, 1993.
Dermody, "Molecular Mechanisms of Persistent Infection by Reovirus," *Current Topics in Microbiology and Immunology*, 233 (2): 1-22, 1998.
Duncan et al., "Conformational and functional analysis of the C-terminal globular head of the reovirus cell attachment protein," Virology, 182 (2): 810-819, 1991.
Ebert et al., "Cathespin B is inhibited in mutant cells selected during persistent reovirus infection," *The Journal of Biological Chemistry*, 279 (5):3837-3851, 2004.
Everts et al., "Replication-selective oncolytic viruses in the treatment of cancer," *Cancer Gene Therapy*, 12 (2):141-161, 2005.
Haller et al., "Genetic mapping of reovirus virulence and organ tropism in severe combined immunodeficient mice: organ-specific virulence genes," *J. Virol.*, 69 (1): 357-364, 1995.
Helander et al., "Protective Immunoglobulin A and G Antibodies Bind to Overlapping Intersubunit Epitopes in the Head Domain of Type 1 Reovirus Adhesin σ1," *J. Virol.* 78 (19): 10695-10705, 2004.
Hoyt et al., "Nonstructural Protein σ 1s is a Determinant of Reovirus Virulence and Influences the Kinetics and Severity of Apoptosis Induction in the Heart and Central Nervous System," *J. Virol.*, 79 (5). 2743-2753, 2005.
Kaye et al., "Genetic basis for altered pathogenesis of an immune-selected antigenic variant of reovirus type 3 (Dearing)," *J. Virol.*, 59 (1):90-97, 1986.
Larson et al., "Reovirus exists in the form of 13 particle species that differ in their content of protein sigma 1," Virology, 201 (2):303-311, 1994.
Lee et al., "Protein sigma 1 is the reovirus cell attachment protein," Virology, 108 (1): 156-163, 1981.
Lee et al., "Reovirus protein sigma 1: from cell attachment to protein oligomerization and folding mechanisms," *Bioessays*, 16 (3):199-206, 1994.
Leone et al., "The N-terminal heptad repeat region of reovirus cell attachment protein sigma 1 is responsible for sigma 1 oligomer stability and possesses intrinsic oligomerization function," *Virology*, 182 (1):336-345, 1991.
Leone et al., "The reovirus cell attachment protein possesses two independently active trimerization domains: basis of dominant negative effects," *Cell*, 71 (3):479-488, 1992.
Loken et al., "Morbidity in immunosuppressed (SCID/NOD) mice treated with reovirus (dearing 3) as an anti-cancer biotherapeutic," *Cancer Biology & Therapy*, 3 (8):734-738, 2004.
Mah et al., "The N-terminal quarter of reovirus cell attachment protein sigma 1 possesses intrinsic virion-anchoring function," *Virology*, 179 (1):95-103, 1990.

(56) References Cited

OTHER PUBLICATIONS

Monks et al., "Feasibility of a high-flux anticancer drug screen using a diverse panel of cultured human tumor cell lines," *J. Nat. Canc. Inst.*, 83 (11) 757-766, 1991.

Mullen et al., "Viral oncolysis," *Oncologist*, 7 (2):106-119, 2002.

Nagata et al., Analysis of functional domains on reovirus cell attachment protein sigma 1 using cloned S1 gene deletion mutants, Virology, 160 (1):162, 1987.

Norman et al., "Reovirus as a novel oncolytic agent," *Journal of Clinical Investigation*, 105 (8):1035-1038, 2000.

Ring, "Cytolytic viruses as potential anti-cancer agents," *Journal of General Virology*, 83 (3):491-502, 2002.

Russell, "RNA viruses as virotherapy agents," *Cancer Gene Therapy*, 9 (12):961-966, 2002.

Strong et al., "The molecular basis of viral oncolysis: usurpation of the Ras signaling pathway by reovirus," *EMBO J.*, 17 (12): 3351-3362, 1998.

Thirukkumaran et al., "Reovirus oncolysis as a novel purging strategy for autologous stem cell transplant," *Blood*, 102 (1):377-387, 2003.

Turner et al., "Site-directed mutagenesis of the C-terminal portion of reovirus protein sigma-1: evidence for a conformation-dependent receptor binding domain," *Virology*, 186 (1):219-227, 1992.

Tyler et al., "Reoviruses and the host cell," *Trends in Microbiology*, 9 (11):560-564, 2001.

Weiner et al., "Absolute linkage of virulence and central nervous system cell tropism of reoviruses to viral hemagglutinin," *J. Infect Dis.*, 141 (5): 609-616, 1980.

Wetzel et al., "Reovirus Variants Selected During Persistent Infections of L Cells Contain Mutations in the Viral S1 and S4 Genes and Are Altered in Viral Disassembly," *J. Virol.*, 71 (2): 1362-1369, 1997.

Wickramasinghe et al., "Cathespin B promotes both motility and invasiveness of oral carcinoma cells," *Arch. Biochem. Biophys.*, 436 (1):187-195, 2005.

Wildner et al., "Comparison of replication-selective, oncolytic viruses for the treatment of human cancers," *Current Opinion in Molecular Therapeutics*, 5 (4):351-361, 2003.

Wilson et al., "Association of the reovirus S1 gene with serotype 3-induced biliary atresia in mice," *J. Virol.*, 68 (10): 6458-6465, 1994.

Spriggs, D.R. et al., "Attenuated Reovirus Type 3 Strains Generated by Selection of Haemagglutinin Antigenic Variants," Nature 297:68-70, Macmillian Journals Ltd (1982).

Alain et al., "Reovirus therapy of lymphoid malignancies," Blood 100:4146-53, American Society of Hematology, Washington, DC (2002).

Chandran et al., "Strategy for nonenveloped virus entry: a hydrophobic conformer of the reovirus membrane penetration protein micro I mediates membrane disruption," J. Virol. 76:9920-9933, American Society for Microbiology, Washington, DC (2002).

De Biasi et al., "Caspase inhibition protects against reovirus-induced myocardial injury in vitro and in vivo," J. Virol. 78:11040-11050, American Society for Microbiology (2004).

Imani, F. et al., "Inhibitory Activity for the Interferon-Induced Protein Kinase is Associated with the Reovirus Stereotype 1 σ3 Protein," Proc. Natl. Acad Sci., USA 85:7887-7981, United States National Academy of Sciences, Washington, DC (1988).

Kim et al., "Caspar, a suppressor of antibacterial immunity in *Drosophila*," Proc. Natl. Acad. Sci. 103:16358-16363, United States National Academy of Sciences, Washington, DC (2006).

Takahashi et al., "Role of ERas in promoting tumour-like properties in mouse embryonic stem cells," Nature 423:541-555, Nature Publishing Group, London, UK (2003).

Terheggen et al., "Myocarditis associated with reovirus infection," Eur. J. Clin. Microbial. Infect. Dis. 22:197-198, Springer-Verlag, Berlin, Germany (2003).

Wilcox et al., "Reovirus as an oncolytic agent against experimental human malignant gliomas," J. Natl. Cancer Inst. 93:903-12, Oxford Univ. Press (2001).

Yang et al., "Efficacy and safety evaluation of human reovirus type 3 in immunocompetent animals: racine and nonhuman primates," Clin. Cancer Res. 10:8561-76, American Associate for Cancer Research, Philadelphia, PA (2004).

Yang et al., "Reovirus as an exprimental therapeutic for brain and leptomeningeal metastases from breast cancer," Gene Therapy 11: 1579-1589, Nature Publishing Group, London UK(2004).

Harrington et al., "Clinical Trials with Oncolytic Reovirus: Moving Beyond Phase I into Combinations with Standard Therapeutics," *Cytokine Growth Factor Rev.*, 21(0):91-98, Elsevier Ltd.(2010).

Kim, M. et al., "Acquired Resistance to Reoviral Oncolysis in Ras-transformed Fibrosarcoma Cells," *Oncogene*, 26:4124-4134, Nature Publishing Group (2007).

Amit, M. "Clonally Derived Human Embryonic Stem Cell Lines Maintain Pluripotency and Proliferative Potential for Prolonged Periods of Culture," *Developmental Biology*, 227:271-278, Academic Press (2000).

Wilcox, M.E., "Evaluation of Reovirus as an Oncolytic Agent in Malignant Gliomas", *University of Calgary, Dept. of Med. Sci.*, 1-92, M.E. Wilcox (2000).

Wu, A., et al., "Biological Purging of Breast Cancer Cells Using an Attenuated Replication-competent Herpes Simplex Virus in Human Hematopoietic Stem Cell Transplantation," Cancer Research, 6:3009-3015 (2001).

Alain et al., "Reovirus Decreases Azoxymethane-Induced Aberrant Crypt Foci and Colon Cancer in a Rodent Model," *Cancer Gene Ther.*, 14:867-872 (2007).

Norman et al., "Reovirus Oncolysis: the Ras/RalGEF/p38 Pathway Dictates Host Cell Permissiveness to Reovirus Infection," Proc. Natl. Acad Sci., 101:11099-11104 (2004).

Thirukkumaran et al., "Biological Purging of Breast Cancer Cell Lines Using a Replication-Competent Oncolytic Virus in Human Stem Cell Autografts," *Bone Marrow Transplant*, 35:1055-1064 (2005).

\* cited by examiner

FIG. 8A Nucleotide sequence alignments of Reovirus S1 (product: sigma1) gene wild type in literature (upper row), wild type in lab strain (middle row) and Attenuated (AV) reovirus (lower row)

```
5'-GCTATTGGTCGG ATG GAT CCT CGC CTA CGT GAA GAA GTA GTA CGG CTG ATA ATC GCA TTA ACG AGT GAT AAT GGA   75
   (sigma1)     met asp pro arg leu arg glu glu val val arg leu ile ile ala leu thr ser asp asn gly    21
   (sigma1s)                                                                                met glu     2

ATG GAT CCT CGC CTA CGT GAA GAA GTA GTA CGG CTG ATA ATC GCA TTA ACG AGT GAT AAT GGA   WT
                ATG GAT CCT CGC C A CGT GAA GAA GTA GTA CGG CTG ATA ATC GCA TTA ACG AGT GAT AAT GGA   AV
                              Deletion-> premature stop*
                              R V E * Y G * *

GGA CTT GAT TCG AGT GTT ACC CAG TTG GGT GCT CGA GTG GGA CAA CTT GAG ACA GGA CTT GCA GAC GTA CGC GTT   375
gly leu asp ser ser val thr gln leu gly ala arg val gly gln leu glu thr gly leu ala asp val arg val   121
    asp leu ile arg val leu pro ser trp val leu glu trp asp asn leu arg gln asp leu gln thr tyr ala leu 102

GGA CTT GAT TCG AGT GTT ACC CAG TTG GGT GCT CGA GTG GGA CAA CTT GAG ACA GGA CTT GCA GAG CTA CGC GTT
GGA CTT GAT TCG AGT GTT ACC CAG TTG GGT GCT CGA GTG GGA CAA CTT GAG ACA GGA ▓▓▓ GCA GAG CTA CGC GTT
                                                                             Pro     Glu Leu
                                                                                     Ser

GAT CAC GAC AAT CTC GTT GCG AGA GTG GAT ACT GCA GAA CGT AAC ATT GGA TCA TTG ACC ACT GAG CTA TCA ACT   450
asp his asp asn leu val ala arg val asp thr ala glu arg asn ile gly ser leu thr thr glu leu ser thr   146
    ile thr thr ile ser leu arg glu trp ile leu gln asn val thr leu asp his                          120

GAT CAC GAC AAT CTC GTT GCG AGA GTG GAT ACT GCA GAA CGT AAC ATT GGA TCA TTG ACC ACT GAG CTA TCA ACT
GAT CAC GAC AAT CTC ▓▓▓ GCG AGA GTG GAT ACT GCA GAA CGT AAC ATT GGA TCA TTG ACC ACT GAG CTA TCA ACT
                    Ala

CTG ACG TTA CGA GTA ACA TCC ATA CAA GCG GAT TTC GAA TCT AGG ATA TCC ACG TTA GAG CGC ACG GCG GTC ACT   525
leu thr leu arg val thr ser ile gln ala asp phe glu ser arg ile ser thr leu glu arg thr ala val thr   171

CTG ACG TTA CGA GTA ACA TCC ATA CAA GCG GAT TTC GAA TCT AGG ATA TCC ACG TTA GAG CGC ACG GCG GTC ACT
CTG ACG TTA CGA GTA ACA TCC ATA CAA GCG GAT TTC GAA TCT AGG ATA TCC ACG TTA GAG CGC ACG GCG GTC ACT

AGC GCG GGA GCT CCC CTC TCA ATC CGT AAT AAC CGT ATG ACC ATG GGA TTA AAT GAT GGA CTC ACG TTG TCA GGG   600
ser ala gly ala pro leu ser ile arg asn asn arg met thr met gly leu asn asp gly leu thr leu ser gly   196

AGC GCG GGA GCT CCC CTC TCA ATC CGT AAT AAC CGT ATG ACC ATG GGA TTA AAT GAT GGA CTC ACG TTG TCA GGG
AGC GCG GGA GCT CCC CTC TCA ATC CGT AAT AAC CGT ATG ACC ATG GGA TTA AAT GAT GGA CTC ACG TTG TCA GGG

AAT AAT CTC GCC ATC CGA TTG CCA GGA AAT ACG GGT CTG AAT ATT CAA AAT GGT GGA CTT CAG TTT CGA TTT AAT   675
asn asn leu ala ile arg leu pro gly asn thr gly leu asn ile gln asn gly gly leu gln phe arg phe asn   221

AAT AAT CTC GCC ATC CGA TTG CCA GGA AAT ACG GGT CTG AAT ATT CAA AAT GGT GGA CTT CAG TTT CGA TTT AAT
AAT AAT CTC GCC ATC CGA TTG CCA GGA AAT ACG GGT CTG AAT ATT CAA AAT GGT GGA CTT CAG TTT CGA TTT AAT

ACT GAT CAA TTC CAG ATA GTT AAT AAT AAC TTG ACT CTC AAG ACG ACT GTG TTT GAT TCT ATC AAC TCA AGG ATA   750
thr asp gln phe gln ile val asn asn asn leu thr leu lys thr thr val phe asp ser ile asn ser arg ile   246

ACT GAT CAA TTC CAG ATA GTT AAT AAT AAC TTG ACT CTC AAG ACG ACT GTG TTT GAT TCT ATC AAC TCA AGG ATA
ACT GAT CAA TTC CAG ATA GTT AAT AAT AAC TTG ACT CTC AAG ACG ACT GTG TTT GAT TCT ATC AAC TCA AGG ATA

GGC GCA ACT GAG CAA AGT TAC GTG GCG TCG GCA GTG ACT CCC TTG AGA TTA AAC AGT AGC ACG AAG GTG CTG GAT   825
gly ala thr glu gln ser tyr val ala ser ala val thr pro leu arg leu asn ser ser thr lys val leu asp   271

GGC GCA ACT GAG CAA AGT TAC GTG GCG TCG GCA GTG ACT CCC TTG AGA TTA AAC AGT AGC ACG AAG GTG CTG GAT
GGC GCA ACT GAG ▓▓▓ AGT TAC GTG GCG TCG GCA GTG ACT CCC TTG AGA TTA AAC AGT AGC ACG AAG GTG CTG GAT
                Stop codon mutation ATG CTA ATA GAC AGT TCA ACA CTT GAA ATT AAT TCT AGT GGA CAG CTA ACT GTT AGA TCG ACA TCC CCG AAT TTG   900
met leu ile asp ser ser thr leu glu ile asn ser ser gly gln leu thr val arg ser thr ser pro asn leu   296

ATG CTA ATA GAC AGT TCA ACA CTT GAA ATT AAT TCT AGT GGA CAG CTA ACT GTT AGA TCG ACA TCC CCG AAT TTG
ATG CTA ATA GAC AGT TCA ACA CTT GAA ATT AAT TCT AGT GGA CAG CTA ACT GTT AGA TCG ACA TCC CCG AAT TTG

AGG TAT CCG ATA GCT GAT GTT AGC GGC GGT ATC GGA ATG AGT CCA AAT TAT AGG TTT AGG CAG AGC ATG TGG ATA   975
arg tyr pro ile ala asp val ser gly gly ile gly met ser pro asn tyr arg phe arg gln ser met trp ile   321

AGG TAT CCG ATA GCT GAT GTT AGC GGC GGT ATC GGA ATG AGT CCA AAT TAT AGG TTT AGG CAG AGC ATG TGG ATA
AGG TAT CCG ▓▓▓ GCT GAT GTT AGC GGC GGT ATC GGA ATG AGT CCA AAT TAT AGG TTT AGG CAG AGC ATG TGG ATA
            Met
```

```
GGA ATT GTC TCC TAT TCT GGT AGT GGG CTG AAT TGG AGG GTA CAG GTG AAC TCC GAC ATT TTT ATT GTA GAT GAT    1050
gly ile val ser tyr ser gly ser gly leu asn trp arg val gln val asn ser asp ile phe ile val asp asp     346

GGA ATT GTC TCC TAT TCT GGT AGT GGG CTG AAT TGG AGG GTA CAG GTG AAC TCC GAC ATT TTT ATT GTA GAT GAT
GGA ATT GTC TCC TAT TCT GGT AGT GGG CTG AAT TGG AGG GTA CAG GTG AAC TCC GAC ATT TTT ATT GTA GAT GAT

TAC ATA CAT ATA TGT CTT CCA GCT TTT GAC GGT TTC TCT ATA GCT GAC GGT GGA GAT CTA TCG TTG AAC TTT GTT    1125
tyr ile his ile cys leu pro ala phe asp gly phe ser ile ala asp gly gly asp leu ser leu asn phe val     371

TAC ATA CAT ATA TGT CTT CCA GCT TTT GAC GGT TTC TCT ATA GCT GAC GGT GGA GAT CTA TCG TTG AAC TTT GTT
TAC ATA CAT ATA TGT CTT CCA GCT TTT GAC GGT TTC TCT ATA GCT GAC GGT GGA GAT CTA TCG TTG AAC TTT GTT

ACC GGA TTG TTA CCA CCG TTA CTT ACA GGA GAC ACT GAG CCC GCT TTT CAT AAT GAC GTG GTC ACA TAT GGA GCA    1200
thr gly leu leu pro pro leu leu thr gly asp thr glu pro ala phe his asn asp val val thr tyr gly ala     396

ACC GGA TTG TTA CCA CCG TTA CTT ACA GGA GAC ACT GAG CCC GCT TTT CAT AAT GAC GTG GTC ACA TAT GGA GCA
ACC GGA TTG TTA CCA CCG TTA CTT ACA GGA GAC ACT GAG CCC GCT TTT CAT AAT GAC GTG GTC ACA TAT GGA GCA

CAG ACT GTA GCT ATA GGG TTG TCG TCG GGT GGT GCG CCT CAG TAT ATG AGT AAG AAT CTG TGG GTG GAG CAG TGG    1275
gln thr val ala ile gly leu ser ser gly gly ala pro gln tyr met ser lys asn leu trp val glu gln trp     421

CAG ACT GTA GCT ATA GGG TTG TCG TCG GGT GGT GCG CCT CAG TAT ATG AGT AAG AAT CTG TGG GTG GAG CAG TGG
CAG ACT GTA GCT ATA GGG TTG TCG TCG GGT GGT GCG CCT CAG TAT ATG AGT AAG AAT CTG TGG GTG GAG CAG TGG

CAG GAT GGA GTA CTT CGG TTA CGT GTT GAG GGG GGT GGC TCA ATT ACG CAC TCA AAC AGT AAG TGG CCT GCC ATG    1350
gln asp gly val leu arg leu arg val glu gly gly gly ser ile thr his ser asn ser lys trp pro ala met     446

CAG GAT GGA GTA CTT CGG TTA CGT GTT GAG GGG GGT GGC TCA ATT ACG CAC TCA AAC AGT AAG TGG CCT GCC ATG
CAG GAT GGA GTA CTT CGG TTA CGT GTT GAG GGG GGT GGC TCA ATT ACG CAC TCA AAC AGT AAG TGG CCT GCC ATG

ACC GTT TCG TAC CCG CGT AGT TTC ACG TGA GGA TCA GAC CAC CCC GCG GCA CTG GGC ATT TTC ATC-3'             1416
thr val ser tyr pro arg ser phe thr                                                                     455

ACC GTT TCG TAC
ACC
```

FIG. 8A (cont.)

FIG. 8B Attenuated Reovirus (AV) S1 gene putative translation, showing many in-frame stop codons

```
        M  D  P  R  H  V  K  K  *  Y  G  *  *  S  H  *  R  V  I  M
1       atggatcctcgccacgttaagaagtagtacggctgataatcgcattaacgagtgataatg    60
        E  H  H  C  Q  K  G  L  N  Q  G  S  R  R  S  R  R  R  L  K
61      gagcatcactgtcaaagggcttgaatcaagggtctcggcgctcgagaagacgtctcaaa    120
        Y  T  L  I  L  S  S  G  S  P  R  D  S  M  M  Q  T  N  E  S
121     tacactctgatactatcctccggatcacccagggactcgatgatgcaaacaaacgaatca   180
        S  L  L  S  K  V  G  M  T  W  L  H  Q  S  V  M  L  N  L  Q
181     tcgctcttgagcaaagtcgggatgacttggttgcatcagtcagtgatgctcaacttgcaa   240
        S  P  D  W  K  A  L  S  E  P  S  K  Q  L  S  M  D  L  I  R
241     tctccagattggaaagctctatcggagccctccaaacagttgtcaatggacttgattcga   300
        V  L  P  S  W  V  L  E  W  D  N  L  R  Q  D  L  Q  S  Y  A
301     gtgttacccagttgggtgctcgagtgggacaacttgagacaggacctgcagagctacgcg   360
        L  I  T  T  I  S  L  R  E  W  I  L  Q  N  V  T  L  D  H  *
361     ttgatcacgacaatctcgctgcgagagtggatactgcagaacgtaacattggatcattga   420
        P  L  S  Y  Q  L  *  R  Y  E  *  H  P  Y  K  R  I  S  N  L
421     ccactgagctatcaactctgacgttacgagtaacatccatacaagcggatttcgaatcta   480
        G  Y  P  R  *  S  A  R  R  S  L  A  R  E  L  P  S  Q  S  V
481     ggatatccacgttagagcgcacggcggtcactagcgcgggagctcccctctcaatccgta   540
        I  T  V  *  P  W  D  *  M  M  D  S  R  C  Q  G  I  I  S  P
541     ataaccgtatgaccatgggattaaatgatggactcacgttgtcagggaataatctcgcca   600
        S  D  C  Q  E  I  R  V  *  I  F  K  M  V  D  F  S  F  D  L
601     tccgattgccaggaaatagggtctgaatattcaaaatggtggacttcagtttcgattta    660
        I  L  I  N  S  R  *  L  I  I  T  *  L  S  R  L  C  L  I
661     atactgatcaattccagatagttaataataacttgactctcaagacgactgtgtttgatt   720
        L  S  T  Q  G  *  A  Q  L  S  K  V  T  W  R  R  Q  *  L  P
721     ctatcaactcaaggataggcgcaactgagtaaagttacgtggcgtcggcagtgactccct   780

*  D  *  T  V  A  R  R  C  W  I  C  *  *  T  V  Q  H  L  K
781     tgagattaaacagtagcacgaaggtgctggatatgctaatagacagttcaacacttgaaa   840
        L  I  L  V  D  S  *  L  L  D  R  H  P  R  I  *  G  I  R  W
841     ttaattctagtggacagctaactgttagatcgcatccccgaatttgaggtatccgatgg    900
        L  M  L  A  A  V  S  E  *  V  Q  I  I  G  L  G  R  A  C  G
901     ctgatgttagcggcggtatcggaatgagtccaaattataggtttaggcagagcatgtgga   960
        *  E  L  S  P  I  L  V  V  G  *  I  G  G  Y  R  *  T  P  T
961     taggaattgtctcctattctggtagtgggctgaattggagggtacaggtgaactccgaca  1020
        F  L  L  *  M  I  T  Y  I  Y  V  F  Q  L  L  T  V  S  L  *
1021    tttttattgtagatgattacatacatatatgtcttccagcttttgacggtttctctatag  1080
        L  T  V  E  I  Y  R  *  T  L  L  P  D  C  Y  H  R  Y  L  Q
1081    ctgacggtggagatctatcgttgaactttgttaccggattgttaccaccgttacttacag  1140
        E  T  L  S  P  L  F  I  M  T  W  S  H  M  E  H  R  L  *  L
1141    gagacactgagcccgcttttcataatgacgtggtcacatatggagcacagactgtagcta  1200
        *  G  C  R  R  V  V  R  L  S  I  *  V  R  I  C  G  W  S  S
1201    tagggttgtcgtcgggtggtgcgcctcagtatatgagtaagaatctgtgggtggagcagt  1260
        G  R  M  E  Y  F  G  Y  V  L  R  G  V  A  Q  L  R  T  Q  T
1261    ggcaggatggagtacttcggttacgtgttgagggggtggctcaattacgcactcaaaca   1320
        V  S  G  L  P  *
1321    gtaagtggcctgccatgacc  1340
```

FIG. 12

AV S4 gene sequence (black: WT (K02739), green: WT lab stock, blue: AV)

ATTENUATED REOVIRUS

This application is a national phase application under 35 U.S.C. § 371 of International Application No. PCT/IB2006/004149, filed Jul. 31, 2006, which claims the benefit of U.S. Provisional Application No. 60/704,604, filed Aug. 1, 2005. These applications are incorporated by reference.

BACKGROUND OF THE INVENTION

I. Field of the Invention

The present invention relates generally to the use of viruses as biological therapeutics for treating diseases, disorders or conditions associated with cellular proliferation, and in particular, for treating malignant conditions such as cancer. More specifically, invention embodiments as disclosed herein relate to novel oncolytic attenuated reoviruses.

II. Description of the Related Art

Cancer includes a broad range of diseases characterized by the presence of inappropriate or unregulated cellular proliferation in a variety of cells and tissues. Worldwide, approximately one in four humans is afflicted with one of the various forms that cancer may take, and reliable therapeutic strategies remain a major clinical challenge for most cancer types. Current approaches include surgical excision of cancerous tissues containing malignant tumors, and radiological, chemotherapeutic or immunotherapeutic ablation of neoplastic or malignant cells. Each of these approaches provides less than ideal efficacy, with shortcomings that include incomplete removal of cancer cells and/or undesired damage or toxicity to normal, healthy tissues and/or inadequate delivery of the anti-cancer agent to the malignantly transformed target cells.

Oncolytic properties of reoviruses have been recognized in the past (Bennette et al., 1967), and more recently, naturally occurring human reoviruses have received attention as candidate therapeutic agents for certain types of cancer (Chiocca, 2002; Everts et al., 2005). Specifically, certain human reoviruses exhibit oncolytic activity, or the ability to preferentially and productively infect, and induce lysis of, cancer cells in which one or more of various altered oncogenic pathways are present. In one example, naturally occurring reoviruses are oncolytic when contacted with activated Ras oncogene-dependent tumor cells. Such oncolysis of activated oncogene-associated cancer cells proceeds through a mechanism that involves Ras pathway-mediated impairment of phosphorylation of double-stranded RNA-activated protein kinase (PKR), which is consequently unable to phosphorylate the translation initiation factor eIF-2$\alpha$, thereby creating permissive conditions for translation of reoviral gene transcripts. (Coffey et al., 1998; Chiocca, 2002; see also U.S. Pat. No. 6,261,555; U.S. Pat. Pub. US 2005/0063954). Reoviruses also exhibit oncolytic potential in myc-overexpressing lymphoid malignancies (Alain et al., 2002).

The reoviruses (Reoviridae) comprise a family of naturally occurring, non-enveloped viruses having a double-stranded RNA (dsRNA) genome that is divided into ten segments and enclosed by two concentric icosahedral protein capsids. Infectious mammalian reovirus virions of various tropisms occur as particles of approximately 85 nm in diameter. The virion outer capsid includes several distinct protein species, among them sigma-1 ($\sigma$1, 50 kDa) which mediates viral attachment to host cell surfaces (Lee et al., 1981; Duncan et al., 1991; Nagata et al., 1987; Turner et al., 1992) via discrete carbohydrate-binding (Chappell et al., 1997; Chappell et al., 2000; Connolly et al., 2001) and virion-anchoring (Mah et al., 1990; Fernandes et al., 1994; Lee et al., 1994) domains. ($\sigma$1 is a product of the bicistronic reoviral S1 gene, which also encodes a non-structural protein designated $\sigma$1s using a distinct but overlapping reading frame (Ernst et al, 1985; Jacobs et al., 1985; Sarkar et al., 1985). Reoviral particles that lack $\sigma$1 have been reported to be non-infectious (Larson et al., 1994). The reoviral S1 gene is believed to play a significant role in determining reoviral pathogenesis (Haller et al., 1995; Wilson et al., 1994; Kaye et al., 1986; Weiner et al., 1980).

The other major reovirus outer capsid proteins, $\sigma$3 (encoded by the reoviral S4 gene, e.g., Ahmed et al., 1982; Giantini et al., 1984) and 111 (encoded by the reoviral M2 gene, e.g., Wiener et al., 1988; Hooper et al., 1996), are present along with $\sigma$1 in intact reovirus virions, but following exposure of the virion to certain proteolytic conditions an altered structure known as an intermediate or infectious subvirion particle (ISVP) results, in which $\sigma$1 persists but $\sigma$3 is lost and two defined $\mu$1 cleavage products remain (Dryden et al., 1993; Jane-Valbuena et al., 1999; Chandran et al., 1999; Chandran et al., 2001). ISVPs may thus result from exposure of intact reovirus virions to proteolytic environments such as those found intracellularly within late endosomes or lysosomes following reoviral host cell infection (via cell surface binding and internalization), or as may be encountered via a natural enteric route, or by artificial means. Following ISVP penetration of the endosomal (or lysosomal) membrane to gain access to the infected host cell's cytoplasm, $\sigma$1 and $\mu$1 proteins are lost to yield a reovirus-derived particle known as a core particle, which is capable of transcribing its viral mRNA contents but which, unlike virions and ISVPs, is no longer infectious.

Initially identified as an apparently innocuous infectious pathogen in the human respiratory and gastrointestinal tracts, the human reovirus has long been recognized for its striking cytocidal activity upon infection of certain types of transformed cells (Duncan et al., 1978; Hashiro et al., 1977). More recently, the relationship between tumor cells containing an activated Ras oncogene and susceptibility of such cells to reoviral oncolysis has been established (Coffey et al., 1998; Strong et al., 1998). Subsequent demonstration of a reovirus role in inducing cancer cell apoptosis suggested at least one mechanism by which reoviral oncolysis proceeds (Clarke et al., 2001), and considerable efforts have been undertaken to develop cancer therapeutics using naturally occurring reoviruses (e.g., U.S. Pat. Nos. 6,565,831; 6,811,775; 6,455,038; 6,808,916; 6,528,305; 6,703,232; 6,136,307; 6,344,195; 6,110,461; 6,261,555; 6,576,234; U.S. Patent Pub. Nos. US2005/0063954; US2005/0026289; US2004/0146491; US2002/0168344; US2004/0126869; US2004/0265271; US2005/0019308).

However, despite reoviral tropism for, and lysis of, Ras-activated tumor cells, efforts to use reoviruses as therapeutic oncolytic agents have been hampered by a number of factors, including (i) as a dsRNA virus having a segmented genome, reovirus is not readily amenable to refinements by genetic engineering (Russell, 2002; Brown et al, 2001); (ii) among transformed cells, reovirus is believed to productively infect only those cells having an activated ras pathway, which accounts for about 30% of human cancers; (iii) many in vivo protocols for reoviral oncolysis employ immunosuppressed or immunocompromised hosts and as such fail to consider the effects of anti-reoviral immune responses or of a generally immunosuppressed state (Everts et al., 2005);

(iv) reoviral tropism is not strictly limited to cancer cells and naturally occurring reoviruses may not be clinically innocuous, with animal models revealing reoviral infection of cardiac myocytes and endothelial cells (Loken et al., 2004) and reoviral induction of undesirable phenomena such as hemorrhage, fibrosis, hepatitis, lymphoma, pancreatitis, necrotizing encephalitis and myocarditis (Loken et al., 2004, and references 23-27 therein); and (v) as with other oncolytic regimes, oncolytic reoviral treatments may also compromise the integrity of the host stem cell compartment. Wild-type reovirus is known, for instance, to adversely affect development of rat and murine embryos, retarding development and inhibiting blastocytst formation (Priscott, 1983; Heggie et al., 1979).

Clearly there is a need in the art for improved reovirus compositions and methods that more selectively and efficiently mediate oncolysis. The present invention addresses such needs and provides other related advantages.

SUMMARY OF THE INVENTION

According to certain embodiments of the invention, there is provided an attenuated reovirus, comprising a reovirus genome that lacks a wild-type reovirus S1 gene. In a further embodiment, the attenuated reovirus is derived from a human reovirus, and in a distinct further embodiment the human reovirus is selected from human reovirus Type 1, human reovirus Type 2 and human reovirus Type 3. In a further embodiment, the human reovirus is selected from human reovirus Type 1 strain Lang, human reovirus Type 2 strain Jones, human reovirus Type 3 strain Dearing and human reovirus Type 3 strain Abney.

In another embodiment, there is provided an attenuated reovirus, comprising a reovirus genome that lacks a wild-type reovirus S1 gene, wherein the attenuated reovirus is derived from a host cell culture that has been persistently infected with a reovirus. In a further embodiment, the attenuated reovirus is derived from a human reovirus, and in a further embodiment the human reovirus is selected from human reovirus Type 1, human reovirus Type 2 and human reovirus Type 3. In a still further embodiment, the human reovirus is selected from human reovirus Type 1 strain Lang, human reovirus Type 2 strain Jones, human reovirus Type 3 strain Dearing and human reovirus Type 3 strain Abney. In one further embodiment of the above described attenuated reovirus, the host cell is a mammalian host cell. In another embodiment, the mammalian host cell is a human host cell.

In another embodiment, there is provided an attenuated reovirus, comprising a reovirus genome that lacks a wild-type reovirus S1 gene, wherein said wild-type reovirus S1 gene comprises a polynucleotide sequence that is at least 90% identical to a sequence selected from SEQ ID NO:1 (T1L, M35963), SEQ ID NO:3 (T2J, M35964), SEQ ID NO:5 (T3D, X01161) and SEQ ID NO:7 (T3A, L37677). In another embodiment, there is provided an attenuated reovirus, comprising a reovirus genome that lacks a reovirus S1 gene which is capable of encoding a reovirus σ1 capsid protein having an amino acid sequence selected from (i) an amino acid sequence that is greater than 10% identical to the sequence set forth in SEQ ID NO:2, 4, 6 or 8, (ii) an amino acid sequence that is greater than 20% identical to the sequence set forth in SEQ ID NO: 2, 4, 6 or 8, (iii) an amino acid sequence that is greater than 40% identical to the sequence set forth in SEQ ID NO: 2, 4, 6 or 8, (iv) an amino acid sequence that is greater than 50% identical to the sequence set forth in SEQ ID NO: 2, 4, 6 or 8, (v) an amino acid sequence that is greater than 70% identical to the sequence set forth in SEQ ID NO: 2, 4, 6 or 8, (vi) an amino acid sequence that is greater than 90% identical to the sequence set forth in SEQ ID NO: 2, 4, 6 or 8, and (vii) an amino acid sequence that is greater than 95% identical to the sequence set forth in SEQ ID NO: 2, 4, 6 or 8.

In another embodiment, there is provided an attenuated reovirus comprising a mutated reovirus S1 gene that is incapable of encoding a reovirus σ1 capsid protein having an amino acid sequence selected from (i) an amino acid sequence that is greater than 10% identical to the sequence set forth in SEQ ID NO: 2, 4, 6 or 8, (ii) an amino acid sequence that is greater than 20% identical to the sequence set forth in SEQ ID NO: 2, 4, 6 or 8, (iii) an amino acid sequence that is greater than 40% identical to the sequence set forth in SEQ ID NO: 2, 4, 6 or 8, (iv) an amino acid sequence that is greater than 50% identical to the sequence set forth in SEQ ID NO: 2, 4, 6 or 8, (v) an amino acid sequence that is greater than 70% identical to the sequence set forth in SEQ ID NO: 2, 4, 6 or 8, (vi) an amino acid sequence that is greater than 90% identical to the sequence set forth in SEQ ID NO: 2, 4, 6 or 8, and (vii) an amino acid sequence that is greater than 95% identical to the sequence set forth in SEQ ID NO: 2, 4, 6 or 8.

In another embodiment, there is provided an attenuated reovirus, comprising a replication-competent reovirus virion that comprises a heritable mutant reovirus S1 gene, wherein said mutant reovirus S1 gene comprises one or a plurality of mutations in a polynucleotide sequence as set forth in SEQ ID NO:1, 3, 5 or 7, and wherein the mutant reovirus gene is incapable of encoding at least one reovirus σ1 capsid protein that comprises an amino acid sequence selected from (i) an amino acid sequence that is greater than 10% identical to the sequence set forth in SEQ ID NO: 2, 4, 6 or 8, (ii) an amino acid sequence that is greater than 20% identical to the sequence set forth in SEQ ID NO: 2, 4, 6 or 8, (iii) an amino acid sequence that is greater than 40% identical to the sequence set forth in SEQ ID NO: 2, 4, 6 or 8, (iv) an amino acid sequence that is greater than 50% identical to the sequence set forth in SEQ ID NO: 2, 4, 6 or 8, (v) an amino acid sequence that is greater than 70% identical to the sequence set forth in SEQ ID NO: 2, 4, 6 or 8, (vi) an amino acid sequence that is greater than 90% identical to the sequence set forth in SEQ ID NO: 2, 4, 6 or 8, and (vii) an amino acid sequence that is greater than 95% identical to the sequence set forth in SEQ ID NO: 2, 4, 6 or 8. In certain further embodiments, the one or a plurality of mutations comprises at least one mutation selected from a nucleotide substitution, a nucleotide deletion and a nucleotide insertion.

In another embodiment, there is provided an attenuated reovirus, comprising a replication-competent reovirus virion that lacks a detectable reovirus σ1 capsid protein. In another embodiment, there is provided an attenuated reovirus, comprising a replication-competent reovirus virion that lacks a detectable reovirus σ1 capsid protein having a polypeptide sequence as set forth in SEQ ID NO: 2, 4, 6 or 8. In another embodiment, there is provided an attenuated reovirus, comprising a replication-competent reovirus virion that lacks a detectable reovirus σ1 capsid protein having a polypeptide sequence that is selected from (i) a polypeptide sequence that is at least 50% identical to the sequence set forth in SEQ ID NO: 2, 4, 6 or 8, and (ii) a polypeptide sequence that is at least 20% identical to the sequence set forth in SEQ ID NO: 2, 4, 6 or 8. In certain further embodiments, the above described attenuated reovirus lacks a wild-type reovirus S4 gene.

Certain embodiments of the invention provide an attenuated reovirus, comprising a replication-competent reovirus virion that lacks a detectable reovirus σ1 capsid protein having a polypeptide sequence that is at least 10% identical to the sequence set forth in SEQ ID NO: 2, 4, 6 or 8. Certain further embodiments of the above described attenuated reovirus provide such an attenuated reovirus that exhibits a decreased level of at least one detectable cytopathic effect toward a non-malignant cell relative to the level of the detectable cytopathic effect that is exhibited toward the non-malignant cell by a non-attenuated reovirus. In certain further embodiments, the non-malignant cell is selected from (i) a differentiated normal cell that comprises at least one of a cardiac myocyte, a pancreatic cell and an endothelial cell, and (ii) an undifferentiated stem cell that comprises at least one of an embryonic stem cell and a neural stem/progenitor cell. In certain other further embodiments, the detectable cytopathic effect comprises at least one detectable cytopathic effect that is selected from apoptosis, necrosis, cytolytic viral replication, altered cell morphology, altered cell adhesion, altered cellular gene expression, altered cellular replication, and altered cellular metabolic activity.

Turning to another embodiment of the present invention, there is provided a method of treating an activated oncogene-associated malignant condition, comprising administering an effective amount of an attenuated reovirus to a subject having an activated oncogene-associated malignant condition, under conditions and for a time sufficient for the attenuated reovirus to mediate an oncolytic effect. In a further embodiment, the attenuated reovirus comprises at least one attenuated reovirus as described above.

In another embodiment, the invention provides a method of treating an activated oncogene-associated malignant condition, comprising contacting one or a plurality of malignant cells from a subject having an activated oncogene-associated malignant condition with an effective amount of an attenuated reovirus, under conditions and for a time sufficient for the attenuated reovirus to mediate an oncolytic effect. In related further embodiments, the attenuated reovirus comprises an attenuated reovirus as described above. In related embodiments, the attenuated reovirus comprises a reovirus that is selected from (a) a reovirus that lacks a reovirus σ1 capsid protein, (b) a reovirus that lacks a reovirus σ1 capsid protein having a polypeptide sequence as set forth in SEQ ID NO:2, 4, 6 or 8, (c) a reovirus that lacks a reovirus σ1 capsid protein having a polypeptide sequence that is at least 50% identical to the sequence set forth in SEQ ID NO: 2, 4, 6 or 8, (d) a reovirus that lacks a reovirus σ1 capsid protein having a polypeptide sequence that is at least 20% identical to the sequence set forth in SEQ ID NO: 2, 4, 6 or 8, (e) a reovirus that lacks a reovirus σ1 capsid protein having a polypeptide sequence that is at least 10% identical to the sequence set forth in SEQ ID NO: 2, 4, 6 or 8, (f) a reovirus genome that lacks a wild-type reovirus S1 gene, (g) a reovirus genome that lacks a wild-type reovirus S1 gene, wherein said gene comprises a polynucleotide sequence that is at least 90% identical to the sequence set forth in SEQ ID NO:1, 3, 5 or 7, (h) a reovirus genome that lacks a reovirus S1 gene which is capable of encoding a reovirus σ1 capsid protein having an amino acid sequence that is greater than 10% identical to the sequence set forth in SEQ ID NO: 2, 4, 6 or 8, and (i) a reovirus comprising a mutated reovirus S1 gene that is incapable of encoding a reovirus σ1 capsid protein having an amino acid sequence that is greater than 10% identical to the sequence set forth in SEQ ID NO: 2, 4, 6 or 8.

In certain related further embodiments, the attenuated reovirus exhibits a decreased level of at least one detectable cytopathic effect toward a non-malignant cell relative to the level of the detectable cytopathic effect that is exhibited toward the non-malignant cell by a non-attenuated reovirus. In certain other related embodiments, there is provided a method which comprises administering, simultaneously or sequentially and in any order, at least one of (i) an anticancer drug that comprises an agent selected from the group consisting of a chemotherapeutic agent, an antibody, a cytokine, a hormone, and an apoptogen, and (ii) radiation therapy. In certain other related embodiments, at least one activated oncogene in the activated oncogene-associated malignant condition comprises an activated ras oncogene. In certain other related embodiments, at least one activated oncogene in the activated oncogene-associated malignant condition comprises an activated oncogene selected from abl, akt, cbl, ets, mos, Bcl-2, crk, fos, fms, HER, hTERT, jun, kit, myb, myc, raf, rel, sos, src, and yes. In certain other related embodiments, the subject is immunosuppressed.

In certain other related embodiments to the above described invention embodiments, the attenuated reovirus is selected from (a) a reovirus that lacks a wild-type reovirus S1 gene, (b) a reovirus that lacks a wild-type reovirus S4 gene, (c) a reovirus that lacks a wild-type reovirus S1 gene and that lacks a wild-type reovirus S4 gene, (d) a reovirus that comprises a heritable mutant reovirus S1 gene, (e) a reovirus that comprises a heritable mutant reovirus S4 gene, and (f) a reovirus that comprises a heritable mutant reovirus S1 gene and a heritable mutant reovirus S4 gene. In certain related embodiments, reovirus S1 and/or S4 genes comprise nucleotide sequences as set forth in the Examples and Drawings, or portions thereof and/or complements thereto.

These and other aspects of the present invention will become apparent upon reference to the following detailed description. To this end, various references are set forth herein which describe in more detail certain background information, procedures, compounds and/or compositions, and are each hereby incorporated by reference as if set forth in their entirety.

BRIEF DESCRIPTION OF THE DRAWINGS

(FIG. 1A) HT1080 and HTR1 Cells grown to 70% confluency were either mock-infected or infected with reovirus (MOI=40 PFUs per cell). At 48 hrs post-infection, cell viability was measured by MTT assay. Viability is expressed as the percentage of surviving cells relative to the control uninfected cells. (FIG. 1B) HT1080 and HTR1 cells grown to 70% confluency were either mock-infected or infected with reovirus (MOI=40 PFUs per cell). At 48 hrs post-infection, cell lysates were prepared and analyzed by western blotting using anti-reovirus antibody. First lane is loaded with reovirus viron lysates showing reovirus structural proteins.

(FIG. 3A) Sequence analysis of N-ras surrounding codon 61 in HT1080 and HTR1 genome. Genomic DNAs were extracted and the N-ras region surrounding codon 61 was amplified and sequenced. (FIG. 3B) Ras activity assay for Hs68 (primary foreskin fibroblast), HT1080 and HTR1 cells. Cells were either serum starved or serum stimulated, then cell lysates were prepared and probed with the active form (GTP bound) of Ras protein. The primary cells (Hs68) demonstrated Ras activation upon serum stimulation, whereas HT1080 and HTR1 cells showed high Ras activation in a serum independent manner.

(FIG. 4A) MTT assay (left panel): HT1080 and 293 cells grown to 70% confluency were either infected with wild-type reovirus or infected with adapted reovirus (MOI=10 PFUs per cell). At 30 hrs post-infection, cell viability was measured by MTT assay. Viability is expressed as the percentage of surviving cells relative to the control uninfected cells. Apoptotic nucleosome detection assay (right panel): Apoptotic nucleosomes in lyastes prepared from cells infected as described above were detected by ELISA. Samples were assayed in triplicate. Error bars indicate standard deviations. (FIG. 4B) HT1080 and L929 cells grown to 70% confluency were either mock-infected or infected with adapted reovirus (MOI=10 PFUs per cell). At 48 hrs post-infection, cells were microphotographed. The bar represents 50 µm. (FIG. 4C) Cell lysates were also prepared at indicated time points following the AV virus infection and examined by western blot analysis using anti-reovirus antibody.

(FIG. 5A) HT1080 and HTR1 cells were either mock-infected or infected with reovirus (MOI=40 PFUs per cell). At 24 hrs post-infection, cells were analyzed by flow cytometric analysis to detect DNA fragmentation and PS (phosphatidyl serine) externalization. (FIG. 5B) Cell lysates from virus infected HeLa, HT1080, and HTR1 cells were prepared at indicated time points (hrs) following reovirus infection and examined by western blot analysis using antibodies against caspase 3, PARP and XIAP. (FIG. 5C) HT1080 and HTR1 cells grown to 70% confluency were subjected to treatment with either camptothecin (2 µM) or Fas ligand (100 ng/ml) and microphotographs were taken at 24 hrs post-treatment. The bar represents 50 m. (FIG. 5D) HT1080, HTR1 and Cured cells were subjected to camptothecin treatment at various concentrations, then cell lysates were prepared and examined by western blot analysis using anti-PARP antibody. (FIG. 5E) HT1080, HTR1 and Cured cells grown to 70% confluency were subjected to adenoviruses challenge (human adenovirus type5 and its variant (E1B deleted adenovirus type5): MOI=20 PFU per cell). Microphotographs were taken at 48 hrs post-infection. The bar represents 50 µm. (FIG. 5F) Cells subjected to the adeonviral infection were labeled with [$^{35}$S]-methionine and viral protein synthesis was monitored by incorporation of [$^{35}$S] methionine from 24 to 48 hrs post-infection. The adenoviral structural proteins are shown in the blot. Mock: mock infection, Wt Ad: wild-type adenovirus type 5 infection, E1B-Ad: E1B deleted adenovirus infection.

(FIG. 6A) HT1080 cells, reovirus-infected HT1080 cells, HTR1 and Cured cells (generated by growth in the presence of reovirus antibody for 3 weeks in the HTR1 culture) were fixed, permeabilized and incubated with FITC conjugated anti-reovirus antibody. Reoviral antigens were detected by FACS scan. (FIG. 6B) Reovirus s1 mRNA levels of HT1080, reovirus-infected HT1080, HTR1 and Cured cells were examined by RT-PCR analysis. Total RNAs for the cells were extracted. Equal amounts of RNA from each sample were then subjected to RT-PCR, followed by selective amplification of reovirus s1 cDNA and the constitutively expressed GAPDH, which served as a PCR and gel loading control. The PCR products were separated on a 2% agarose gel and visualized with ethidium bromide under UV light.

(FIG. 7A) Representative SCID mice bearing tumors were photographed at 5 weeks post xenograft implantation of HT1080, HTR1, Cured, or a mixture of HTR1 and Cured cells subcutaneously at the hind flank of the mice (each group; n=5). H&E staining of injected sites shows highly proliferating tumor cells in HT1080- and Cured cells-injected group of mice, but not in the HTR1-injected and co-injected group. The bar represents 100 µm. (FIG. 7B) Tumor volumes of the SCID mice were monitored by measuring the sizes of the tumors using an engineering caliper. Both the HTR1-injected and the (HTR1+Cured) co-injected groups of mice had no tumors but had blacktails at 3-7 months post injection, possibly due to AV virus-mediated disease in SCID mice (Loken et al., 2004).

FIGS. 8A-B show reovirus Type 3 S1 gene sequences. (FIG. 8A) Type 3 (Dearing strain) wild-type S1 encoding nucleotide sequence for S1 (SEQ ID NO:9, Genbank Accession number X01161) aligned with a laboratory variant S1 encoding sequence (SEQ ID NO:10) and also aligned with a mutated S1 nucleotide sequence (SEQ ID NO:11, Genbank Accession number AY860061) containing a premature stop codon. (FIG. 8B) Deduced translation of mutated S1 nucleotide sequence (SEQ ID NO:12, Genbank Accession number AY860061) showing multiple in-frame stop codons.

(FIG. 10A) Time-course of tumor volume measurements; (FIG. 10B) histology and immunohistology.

(FIG. 11A) Time-course of tumor volume measurements; (FIG. 11B) histology and immunohistology.

FIG. 12 shows reovirus Type 3 S4 gene sequences. Type 3 (Dearing strain) wild-type S4 encoding nucleotide sequence for S1 (SEQ ID NO:13, Genbank Accession number K02739) aligned with a laboratory variant S4 encoding sequence (SEQ ID NO: 14) and also aligned with a mutated S4 nucleotide sequence (SEQ ID NO:15) from an attenuated reovirus (AV).

DETAILED DESCRIPTION OF THE INVENTION

Figure 1A:
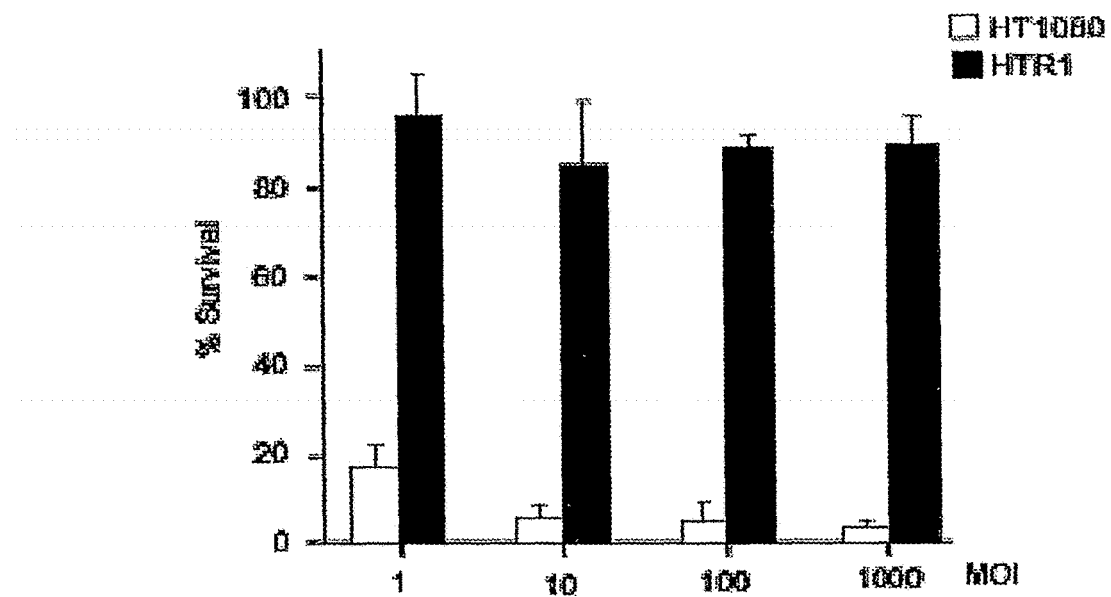
FIGS. 1A-B show properties of persistently infected reovirus resistant cells.

The present invention relates, in certain embodiments, to an attenuated reovirus having desirable properties for use as an oncolytic agent, thereby providing unexpected advantages over naturally occurring wild-type reoviruses. The attenuated reovirus disclosed herein comprises an infectious, replication-competent reovirus virion that lacks a detectable reovirus σ1 capsid protein by virtue of the genome of such reovirus lacking a wild-type reovirus S1 gene. As such, the attenuated reovirus derives from the surprising observation that a mutated reovirus which lacks a detectable reovirus σ1 capsid protein unexpectedly retains the ability to productively infect a target tumor cell while desirably avoiding cytopathic effects on non-malignant cells. As noted above, prior to the instant disclosure, reoviral particles that lacked σ1 had been understood to be non-infectious (Larson et al., 1994). Additionally and in certain embodiments as described herein, a presently disclosed attenuated reovirus may comprise a mutated reoviral S4 gene. The reovirus wild-type S4 gene encodes a reovirus capsid σ3 polypeptide involved in virion processing during reoviral replicative infection of a host cell (e.g., Ahmed et al, 1982; Giantini et al, 1984). As disclosed herein, according to certain embodiments an attenuated reovirus may comprise a mutated reovirus S4 gene that comprises one or a plurality of mutations in a reoviral σ3 polypeptide-encoding genomic sequence, relative to a wild-type S4 gene sequence.

The herein described attenuated reovirus lacks a detectable σ1 capsid protein yet is, unexpectedly, infectious. As noted above, σ1 has been implicated in reoviral binding and attachment to cells via cell surface sialic acid residues in an initial step of viral replicative infection (Lee et al., 1981; Duncan et al, 1991; Nagata et al., 1987; Turner et al, 1992; Chappell et al., 1997; Chappell et al., 2000; Connolly et al, 2001). Despite lacking detectable σ1, the attenuated reovirus described herein is capable of host cell entry and cytolytic viral replication. Additionally, the attenuated reovirus exhibits the surprising property of inducing a decreased (i.e., reduced with statistical significance) level of one or more cytopathic effects toward a non-malignant cell relative to the level of the cytopathic effect that is exhibited toward the non-malignant cell by a naturally occurring, non-attenuated reovirus. Accordingly and as described in greater detail below, the attenuated reovirus provided herein offers improvements over reoviruses of the prior art, including suitability for use as an oncolytic agent without undesirable side-effects such as tropism for, and cytolysis of, normal (e.g., non-malignant) cells.

According to certain embodiments as disclosed herein, the attenuated reovirus may be derived from any reovirus, which refers to a member of the Family Reoviridae and includes reoviruses having a variety of tropisms and which may be obtained from a variety of sources. (Tyler and Fields, 1996) In certain embodiments mammalian reoviruses are preferred, and in certain further embodiments human reoviruses are particularly preferred as the starting point for the derivation of an attenuated reovirus as described herein, although the invention is not intended to be so limited, and based on the present disclosure the skilled artisan will recognize situations where any particular reovirus may be desirable for such purposes. In certain particularly preferred embodiments, the attenuated reovirus may be derived from human reoviruses, for example, human Type 3 (Dearing), Type 1 (Lang), Type 2 (Jones), or Type 3 (Abney) reoviruses, while in certain other embodiments (e.g., for use in animal models having relevance to human diseases, or for veterinary applications) the attenuated reovirus may be derived from one or more reoviruses displaying tropisms toward cells of other mammalian species, including non-human primates (e.g., chimpanzee, gorilla, macaque, monkey, etc.), rodents (e.g., mice, rats, gerbils, hamsters, rabbits, guinea pigs, etc.), dogs, cats, common livestock (e.g., bovine, equine, porcine, caprine), etc., or alternatively, reoviruses having distinct tropisms (e.g., avian reoviruses) may be used.

As described herein, certain embodiments relate to attenuated reoviruses that are recovered following persistent infection regimens in vitro, but attenuated reoviruses are also contemplated that may be derived according to other methodologies, including generation and identification of σ1-deficient and/or σ1-defective mutants (and in certain embodiments also including, additionally or alternatively, generation and identification of σ3-deficient and/or σ3-defective mutants) by molecular biological approaches, and also including isolation of naturally occurring σ1-deficient and/or σ1-defective mutants and/or σ3 mutants, and/or artificial induction of such σ1 (and/or σ3) mutants by chemical, physical and/or genetic techniques (e.g., assortative recombination of reoviral genes in a productively infected host cell).

The attenuated reovirus disclosed herein comprises an infectious, replication-competent reovirus virion (i.e., virus particle including viral genome, core proteins and protein coat) that lacks a wild-type reovirus S1 gene and consequently lacks a detectable reovirus σ1 capsid protein. In certain embodiments the attenuated reovirus lacks a wild-type reovirus S4 gene and expresses a mutated reovirus σ3 capsid protein. As is known in the relevant art, an infectious, replication-competent reovirus is one that is capable, upon introduction to a suitable host cell under appropriate conditions and for a sufficient time, of binding to and being internalized by the host cell and thence directing replication of the reoviral genome and biosynthesis of reoviral structural proteins in a manner that permits assembly of complete progeny reoviruses that, upon release from the host cell, are capable of productively infecting other host cells to perpetuate the viral replication cycle.

The presence of a malignant condition in a subject refers to the presence of dysplastic, inappropriately proliferating, cancerous and/or transformed cells in the subject, including, for example neoplastic, tumor, non-contact inhibited or oncogenically transformed cells, or the like (e.g., melanoma, carcinomas such as adenocarcinoma, squamous cell carcinoma, small cell carcinoma, oat cell carcinoma, etc., sarcomas such as fibrosarcoma, chondrosarcoma, osteosarcoma, etc., hepatoma, neuroblastoma, melanoma, hematopoietic malignancies such as lymphoma, leukemia, myeloma, etc.); which are known to the art and for which criteria for diagnosis and classification are established. Oncolytic properties of reoviruses may derive from viral tropism for malignantly transformed cells in concert with a susceptible intracellular environment, for example, impaired PKR phosphorylation in Ras-activated cells as described above.

The presently described attenuated reoviruses are contemplated for use in a wide range of activated oncogene-associated malignant conditions, i.e., malignant conditions in which a mutation or other structural or functional alteration to an oncogene or an oncogene product renders the oncogene constitutively active with deleterious consequences (e.g., unregulated cell growth), including malignancies wherein the activated oncogene is Ras or an upstream or downstream component of the Ras pathway, and also including other oncogene-associated malignant conditions, for example, wherein the activated oncogene may be at least one of abl, akt, cbl, ets, mos, Bcl-2, crk, fos, fms, HER2, hTERT, jun, kit, myb, myc, raf, rel, sos, src, and yes. (For a review of viral oncogenes see Bishop, 1985; Vogelstein et al., 2004)

For instance, resistance to reoviral oncolysis has been observed by the present inventors in human cancer cells having an activated Ras gene and intact PKR phosphorylation, suggesting that reoviral oncolysis is not exclusively dependent on the Ras-status of cancer cells. Accordingly, certain embodiments relate to attenuated reoviruses that may be used in methods of treating an activated oncogene-associated malignant condition, which methods comprise administering an effective amount of an attenuated reovirus as described herein to a subject having such a malignant condition, under conditions and for a time sufficient for the attenuated reovirus to mediate an oncolytic effect.

Oncolytic activity of the attenuated reovirus described herein need not, however, be limited to activity directed against malignant conditions associated with a known oncogene. Without wishing to be bound by theory, attenuated reovirus oncolytic activity may proceed, for example, via host cell mechanisms of innate immunity (e.g., Martinon, 2005; Philpott et al, 2004) and/or via host cell mechanisms of intrinsic immunity (e.g., Bieniasz, 2004). Additionally according to non-limiting theory, a number of other genes and/or gene products that are not typically regarded as oncogenes or oncogene products per se have been implicated in tumorigenesis or in mechanisms underlying predisposition to cancer (Vogelstein et al., 2004; Futreal et al., 2004), such that certain invention embodiments disclosed herein contemplate attenuated reoviruses having oncolytic activity toward malignancies associated with mutations in oncogenes and/or in non-oncogenes, for instance, tumor-suppressor genes and stability genes. Determination of the suitability of the presently disclosed attenuated reoviruses for oncolytic application to a particular malignant condition may include may be achieved using in vitro or in vivo methodologies such as those described herein or known to the art, for example by obtaining a biological sample comprising tumor cells (e.g., Monks et al., 1991) and administering thereto the attenuated reovirus under conditions and for a time sufficient to detect an oncolytic effect.

"Attenuated" reoviruses described herein include reoviruses that exhibit altered (i.e., increased or decreased in a statistically significant manner) infective, replicative and/or lytic properties toward or in a host cell, relative to levels of one or more such properties that are exhibited by known, naturally occurring or wild-type reoviruses. In many preferred embodiments the attenuated reovirus will exhibit decreased infectivity, replicative ability and/or lytic potential, relative to a wild-type reovirus. Examples of such altered properties by which one may discern an attenuated reovirus as presently disclosed include various manifestations of viral cytopathic effects, for instance, the multiplicity of infection (MOI, the average number of virions that infect each cell) required for productive infection of a given host cell, the degree of host cell cytolysis induced by viral infection (further including apoptosis and/or necrosis), the titer of viruses released from a productively infected host cell following cytolytic viral replication, and other parameters by which those familiar with the art can determine viral activities toward host cells. Other indicia of cytopathic effects include altered host cell morphology, altered cell adhesion (to substrates such as extracellular matrix proteins or semisolid growth media, or to other cells), altered expression levels of one or more cellular genes, altered ability of host cells to replicate, and/or other alterations in cellular metabolic activity.

I. REOVIRUS NUCLEIC ACID AND PROTEIN SEQUENCES

As noted above, an attenuated reovirus as disclosed herein may comprise a replication-competent reovirus virion that lacks a detectable reovirus σ1 capsid protein, for example, by lacking a wild-type reoviral S1 gene. As also noted above, the reoviral S1 gene is bicistronic and encodes two products using distinct but overlapping reading frames, one of which is the outer capsid protein σ1. Among the three major reoviral serotypes, σ1 proteins exhibit a lower degree of amino acid sequence conservation than do other reoviral proteins, despite the fact that the σ1 proteins retain certain conserved structural and functional features (reviewed in Lee et al. (1994) and references cited therein; see also, e.g., Dermody et al. (1990)). Attenuated reoviruses are contemplated that may be genetically homogeneous or that may comprise a genetically heterogeneous reoviral population, such as may be the result of mutation and/or of assortative recombination within an infected host cell among reoviral genome segments derived from two or more distinct polymorphic reoviral strains with which the cell has been infected. Attenuated reoviruses described herein comprise a heritable mutant reovirus S1 gene, and as such the invention expressly does not include wild-type reovirus particles that comprise a wild-type S1 gene, even where such particles result from subjecting a wild-type reovirus to proteolytic conditions or otherwise artificially stripping a wild-type reovirus of σ1 capsid protein (e.g., Chandran et al., 1999; Chandran et al., 2001).

A reoviral gene refers to the segment of reoviral genomic RNA involved in producing a polypeptide chain; it includes the coding region for the polypeptide product (e.g., exon) as well as regions preceding and following the coding region "leader and trailer" segments. Wild-type S1 gene sequences include the S1 gene sequences identified in predominant forms of naturally occurring reoviruses isolated from respiratory or enteric tissues of infected subjects, or consensus sequences derived from such sequences. S1 gene sequences for a number of reoviruses, including the human reoviruses, have been determined (e.g., Genbank Accession numbers for human reovirus S1 gene sequences: human type 3 reovirus S1: X01161; human type 2 reovirus S1: M35964; human type 1 reovirus S1: M35963), including polynucleotide sequences encoding σ1 proteins as well as the amino acid sequences of the encoded σ1 proteins themselves. (e.g., Genbank Accession numbers for major human reovirus serotype S1 gene sequences: human type 1 reovirus strain Lang (T1L) Acc. No. M35963, SEQ ID NOS:1 (nucleotide, nt) and 2 (amino acid, aa); human type 2 reovirus strain Jones (T2J) Acc. No. M35964, SEQ ID NOS:3 (nt) and 4 (aa); human type 3 reovirus strain Dearing (T3D) Acc. No. X01161, SEQ ID NOS:5 (nt) and 6 (aa); human type 3 reovirus strain Abney (T3A) Acc. No. L37677, SEQ ID NOS:7 (nt) and 8 (aa)). Reoviral S1 and S4 gene sequences as disclosed herein are contemplated according to certain embodiments described herein, including sequences set forth in the Examples and Drawings.

Nucleic acids according to certain embodiments of the present invention, also referred to herein as polynucleotides, may be in the form of RNA including double-stranded RNA (dsRNA) as is found in reoviral genomes, or single-stranded RNA (ssRNA), or may in certain embodiments be in the form of DNA, which DNA includes cDNA, genomic DNA, and synthetic DNA. The RNA or DNA may be double-stranded or single-stranded, and if single stranded may be the coding strand or non-coding (anti-sense) strand. A coding sequence which encodes a σ1 polypeptide for use according to certain embodiments of the invention may be identical to a coding sequence known in the art for any given reovirus σ1, or may be a different coding sequence, which, as a result of the redundancy or degeneracy of the genetic code, encodes the same σ1 polypeptide.

Nucleic acids which encode σ1 polypeptides according to certain invention embodiments may therefore include, but are not limited to: only the coding sequence for the σ1 polypeptide; the coding sequence for the σ1 polypeptide and additional coding sequence; the coding sequence for the σ1 polypeptide (and optionally additional coding sequence) and non-coding sequence, such as non-coding sequences 5' and/or 3' of the coding sequence for the σ1 polypeptide, which for example may further include but need not be limited to one or more regulatory nucleic acid sequences that may be a regulated or regulatable promoter, enhancer, other transcription regulatory sequence, repressor binding sequence, translation regulatory sequence or any other regulatory nucleic acid sequence. Thus, the term "nucleic acid encoding" or "polynucleotide encoding" a σ1 protein encompasses a nucleic acid which includes only coding sequence for a σ1 polypeptide as well as a nucleic acid which includes additional coding and/or non-coding sequence(s).

According to certain preferred embodiments there is provided an attenuated reovirus comprising a reovirus genome that lacks a wild-type reovirus S1 gene, or that comprises a mutated reovirus S1 gene that is incapable of encoding a reovirus σ1 capsid protein that has an amino acid sequence that is greater than 10%, 20%, 40%, 50%, 70%, 90%, or 95% identical to the amino acid sequence set forth in SEQ ID NOS:2, 4, 6 or 8. Methodologies for determining whether a mutated S1 gene is present by sequencing a reovirus S1 gene will be apparent from the present disclosure and as known in the art, according to techniques described, for example, in Ausubel et al. (1989); Ausubel et al. (1993); Sambrook et al. (1989); Maniatis et al. (1982); Glover (1985); Hames and Higgins (1985) and elsewhere. A mutated S1 gene thus refers to an S1 gene having a polynucleotide sequence that differs at one or a plurality of nucleotide sequence positions from the nucleotide sequence of a corresponding S1 wild-type or consensus sequence by one or more of a nucleotide substitution, a nucleotide insertion, and a nucleotide deletion, as can be readily determined.

Additionally or alternatively, polynucleotide sequences of reoviral S1 genes, or amino acid sequences of reoviral 81 polypeptides, can be compared for purposes of determining whether a mutated S1 gene (or its product) may be present. As known in the art "similarity" between two polypeptides is determined by comparing the amino acid sequences and conserved amino acid substitutions thereto of a first polypeptide to the sequence of a second polypeptide. As used herein, "% identity" refers to the percentage of identical amino acids situated at corresponding amino acid residue positions when two or more polypeptide are aligned and their sequences analyzed using an appropriate sequence analysis tool, such as the gapped BLAST algorithm (e.g., Altschul et al., 1997) which weights sequence gaps and sequence mismatches according to the default weightings provided by the National Institutes of Health/NCBI database (Bethesda, Md.; see www.ncbi.nlm.nih.gov/cgi-bin/BLAST/nph-newblast), or with other similar tools (e.g., MEGALIGWM, GENEWORKS™, Align or the BLAST algorithm (Altschul, 1991; Henikoff et al., 1992), which is available at the NCBI website (see www/ncbi.nlm.nih.gov/cgi-bin/BLAST). Other sequence alignment algorithms, with which those having ordinary skill in the art will be familiar, may also be used.

The presence of nucleic acids which hybridize to σ1 encoding polynucleotide sequences, or their complements, can be determined, as will be readily apparent to those familiar with the art, if there is at least 70%, preferably 80-85%, more preferably at least 90%, and still more preferably at least 95%, 96%, 97%, 98% or 99% identity between the sequences. Certain embodiments particularly relate to nucleic acids which hybridize under stringent conditions to the σ1 encoding nucleic acids referred to herein. As used herein, the term "stringent conditions" means hybridization will occur only if there is at least 90-95% and preferably at least 97% identity between the sequences. The ability to detect presence or absence of nucleic acids which hybridize to σ1 encoding nucleic acids referred to herein may be used, in preferred embodiments, to determine whether a mutated reoviral S1 gene is incapable of encoding polypeptides which retain substantially the same biological function or activity as the wild-type reoviral σ1 polypeptides such as those described in the references cited herein.

As used herein, to "hybridize" under conditions of a specified stringency is used to describe the stability of hybrids formed between two single-stranded nucleic acid molecules. Stringency of hybridization is typically expressed in conditions of ionic strength and temperature at which such hybrids are annealed and washed. Typically "high", "medium" and "low" stringency encompass the following conditions or equivalent conditions thereto: high stringency: 0.1×SSPE or SSC, 0.1% SDS, 65° C.; medium stringency: 0.2×SSPE or SSC, 0.1% SDS, 50° C.; and low stringency: 1.0×SSPE or SSC, 0.1% SDS, 50° C. As known to those having ordinary skill in the art, variations in stringency of hybridization conditions may be achieved by altering the time, temperature and/or concentration of the solutions used for prehybridization, hybridization and wash steps, and suitable conditions may also depend in part on the particular nucleotide sequences of the probe used, and of the blotted, proband nucleic acid sample. Accordingly, it will be appreciated that suitably stringent conditions can be readily selected without undue experimentation where a desired selectivity of the probe is identified, based on its ability to hybridize to one or more certain proband sequences while not hybridizing to certain other proband sequences.

According to certain embodiments there is provided an attenuated reovirus, comprising a replication-competent reovirus virion that comprises a heritable mutant reovirus S1 gene, the mutant S1 gene comprising one or a plurality of mutations in a reoviral σ1 encoding genomic sequence (e.g., SEQ ID NOS:1, 3, 5 or 7). Determination of the presence or absence of such a mutant (e.g., one or a plurality of nucleotide substitutions, insertions and/or deletions) is within the routine practice of the art as described herein. Similarly, a heritable mutant reovirus S1 gene refers to a mutated S1 gene (relative to a wild-type sequence such SEQ ID NOS:1, 3, 5 or 7) that is passed on from an infectious reovirus to progeny which result from productive infection of a host cell, wherein the presence of the heritable mutation in progeny virus can be determined based on the herein described mutated S1 gene, using established molecular biology procedures. Several mutations in a murine reoviral S1 gene sequence encoding a σ1 protein are disclosed by Hoyt et al. (2005) and according to certain embodiments of the invention described herein the mutations of Hoyt et al. are expressly excluded.

Additionally and in certain embodiments as described herein, there is provided herein an attenuated reovirus that may comprise a replication-competent reovirus virion that comprises a heritable mutant reovirus S4 gene (which encodes a reovirus capsid σ3 polypeptide involved in virion processing during reoviral replicative infection of a host cell), which mutated S4 gene comprises one or a plurality of mutations in a reoviral σ3 encoding genomic sequence (e.g., a mutant S4 gene sequence disclosed herein such as SEQ ID NO:15) relative to a wild-type S4 gene sequence (e.g., SEQ ID NOS:13, 14, 15, see FIG. 12 and Genbank Acc. No. K02739). Detection and identification of such a mutant S4 gene and/or of a related mutant σ3 polypeptide may be determined based on S4-specific sequences and structures as provided herein, and otherwise according to principles and methodologies analogous to those disclosed herein for mutant S1 genes and σ1 polypeptides. Other alterations in the reoviral S4 gene, distinct from those disclosed herein, have been recognized in the maintenance of persistent reoviral infections in cell cultures (Ahmed et al., 1982; Wetzel et al., 1997; Baer et al., 1997) and are expressly excluded from certain presently contemplated embodiments.

The term "isolated" means that the material is removed from its original environment (e.g., the natural environment if it is naturally occurring). For example, a naturally occurring nucleic acid or polypeptide present in an intact virus or in a living animal is not isolated, but the same nucleic acid or polypeptide, separated from some or all of the co-existing materials in the natural system, is isolated. Such nucleic acids could be part of a vector and/or such nucleic acids or polypeptides could be part of a composition, and still be isolated in that such vector or composition is not part of its natural environment.

As described herein and known to the art, the reovirus outer capsid σ1 protein may be readily detected on the basis of its biochemical and/or immunochemical properties (e.g., Mah et al., 1990; Leone et al., 1991; Chappell et al., 1997), typically by employing one or more techniques including immunodetection (e.g., σ1-specific immunoprecipitation, western immunoblot analysis, immunoaffinity chromatography, immunofluorescent staining, immunocytofluorimetry, electrophoresis of radiolabeled reovirus polypeptides, etc.), hemagglutination, and/or related methodologies. Accordingly these and other means for detecting a reoviral σ1 protein have been established, and in view of the teachings herein, those familiar with the art will appreciate what are art-accepted criteria and state-of-the-art sensitivity for detecting σ1 protein, such that a replication-competent reovirus virion that lacks a "detectable" reovirus σ1 capsid protein will be understood to include such a reovirus for which σ1 protein cannot be detected when currently conventional practices for determining σ1 protein, if present, are employed.

Host cells for use in the herein provided compositions and methods may be any suitable cell that can be maintained in culture under conditions and for a time sufficient to support a productive reoviral replication cycle. The reoviral replication cycle includes viral binding to and internalization by the host cell, viral uncoating and entry into the cytoplasm, transcription of the viral genome and translation of the viral transcripts to produce viral proteins which are capable of encapsidating viral genetic material, to provide new progeny reovirus virions that are released from the infected host cell upon subsequent cell lysis.

As described in greater detail below, a preferred method for generating an attenuated reovirus according to the present disclosure relates to an attenuated reovirus that is derived from a host cell culture that has been persistently infected. Persistent infection regimens preferably involve a host cell line that is known to be susceptible to reovirus infection, which host cell line can be exposed to repeated rounds of reovirus infection in order to select for reovirus-resistant cells that are capable of surviving even while supporting an ongoing or persistent reoviral infection. To derive an attenuated reovirus, a susceptible cultured host cell is infected with a reovirus preparation, for example, one of the known reovirus laboratory stocks (e.g., T3D, T3A, T2J, T1L), at a suitable MOI such that the majority of cells are lysed while a small proportion (typically less than 20, 10, 5 or 1 percent of cells remains viable, and can be maintained and expanded in culture. Surviving cells are expanded in culture and then exposed to a second round of viral infection, and the process may be repeated one or several times, with periodic analysis of the surviving cells for evidence of a persistent reoviral infection. Alternatively, in some instances non-cytocidal persistent reoviral infection may be established. Reoviral infections may be detected, for example, by immunologically probing samples of surviving cells for the presence of reoviral proteins, or by molecularly probing samples of surviving cells for the presence of reoviral nucleic acid sequences.

Additionally, viral particles shed by persistently infected cells may be used to productively infect unselected (i.e., reovirus-sensitive) host cell cultures, for purposes of characterizing the progeny so obtained. Thus, there is provided by the present disclosure a method for identifying an attenuated reovirus comprising persistently infecting a suitable host cell with a candidate attenuated reovirus that is obtained as just described, and determining the presence of an attenuated reovirus by identifying in such candidate virus the lack of a detectable reovirus σ1 capsid protein, and/or by determining that the candidate virus comprises a heritable mutant reovirus S1 gene. The mutant S1 gene may comprise a polynucleotide sequence as set forth in SEQ ID NO:1, 3, 5 or 7 but having one or a plurality of mutations that prevent expression of a detectable reovirus σ1 capsid protein, and/or the mutant S1 gene may be incapable of encoding at least one reovirus σ1 capsid protein having an amino acid sequence that is greater than 10%, 20%, 40%, 50%, 70%, 90% or 95% identical to the amino acid sequence as set forth in SEQ ID NO:2, 4, 6, or 8.

Although the attenuated reovirus which comprises a heritable mutation in the reovirus S1 gene may be derived from a wild-type reovirus as the product of persistently infected host cells in vitro, the invention is not intended to be so limited and also contemplates other ways to make, select for, and identify the attenuated reovirus. For example, immunocompromised animal hosts such as genetically immunoincompetent animals (e.g., SCID mice, nude mice, etc.) or artificially immunosuppressed animals (e.g., following immunoablative radiation or pharmacological intervention with immunsuppressive agents such as cyclosporin, cortisone, cyclophosphamide, FK506, leflunomide see also, e.g., Gummert et al. (1999)) may be used for in vivo persistent infection regimens, according to which reovirus-resistant cells may be derived as sources of shed attenuated reovirus, including following serial passage in vivo of such cells during the course of repeated rounds of viral infection.

Additional methods for generating an infectious, replication-competent attenuated reovirus are provided in certain embodiments of the present invention, in view of the disclosure provided herein that useful attenuated reoviruses may be derived wherein the S1 gene comprises a heritable mutation, for example, where the attenuated reovirus lacks a detectable σ1 capsid protein. Thus, for instance, spontaneously arising mutant reoviruses, including genetic reassortants produced by multiply infected cells as discussed above, or mutant reoviruses that result from exposure to mutagenizing conditions such as chemical mutagens (e.g., ethylmethane sulfonate, methylmethane sulfonate, diethylsulfonate, 5-bromodeoxyuridine, nitrosoguanidines, or the like) or physical mutagenizing conditions (e.g., ultraviolet light, x-rays, other ionizing radiation) may be screened, based on the instant disclosure, for mutations in the S1 gene, and in particular for inability to express detectable σ1 protein, to identify an attenuated reovirus. As a pre-screen, for instance, candidate mutant reoviruses may be identified from among the progeny of a viral population that has been exposed to mutagenizing conditions concomitant with viral replication, by assaying for mutants that may be temperature-sensitive or resistant to other physicochemical agents (e.g., ethanol). Viruses evidencing such phenotypic alteration(s) (e.g., relative to wild-type control viruses, and in a statistically significant manner) may then be further examined for genetic alterations, such as loss of S1 gene expression according to the present application.

Still other approaches to generating an attenuated reovirus may usefully exploit the disclosure herein of the heritable S1 mutation that results in a lack of detectable σ1 protein expression, by applying nucleic acids-based gene regulation approaches to S1 gene expression. Hence, by way of non-limiting example, antisense polynucleotides (e.g., U.S. Pat. Nos. 5,168,053; 5,190,931; 5,135,917; 5,087,617; Clusel et al. (1993); Gee et al. (1994)), ribozymes (e.g., U.S. Pat. Nos. 5,272,262; 5,144,019; 5,168,053; 5,180,818; 5,116,742; 5,093,246), or small interfering RNA (siRNA, see, e.g., WO 99/32619; WO 01/75164; U.S. Pat. No. 6,506,559; Fire et al. (1998); Sharp, (1999); Elbashir et al. (2001); Harborth et al. (2001); Tuschl (2001); Sharp (2001); Bernstein et al. (2001); Zamore (2002); Plasterk (2002); Zamore (2001); Matzke et al. (2001); Scadden et al. (2001)) or other nucleotide sequences may be designed in view of available sequence information in a manner such that they are directed at impairing S1 gene expression for purposes of decreasing effective σ1 protein levels in a reovirus. Such approaches, given the present disclosure, will permit those skilled in the art to down-regulate S1 gene expression and to determine the presence of an attenuated reovirus that lacks detectable σ1 protein readily and through routine methodologies.

Another alternative approach to the generation of attenuated reoviruses having mutated S1 genes may employ genetically engineered artificial S1 gene constructs having specifically targeted nucleotide sequence mutations that are designed to preclude productive σ1 protein expression, for introduction into multiply infected host cells undergoing reassortative reoviral gene segment recombination. Without wishing to be bound by theory, low frequency reassortant or recombinant reoviruses that acquire such engineered S1 genes, and hence lack detectable σ1 protein, may be screened for and isolated from among the viral progeny of such lytically infected host cells.

A variety of biological assays may be combined with any of the foregoing methods for generating an attenuated reovirus, for purposes of selecting for an attenuated reovirus having a desirable phenotype. By way of non-limiting example, an attenuated reovirus that is deficient in σ1 protein expression may be further selected on the basis of its decreased (e.g., in a statistically significant manner relative to wild-type reovirus) adhesion to target host cell surfaces, or of decreased infectivity in normal tissues or decreased damage to cells (in vivo or ex vivo) while retaining oncolytic effects toward malignant cells.

It will be readily apparent that additional variations of such phenotypic selection are contemplated, and may depend on particular tumor cell types in which oncolysis is desired and/or particular non-malignant cell types in which oncolysis is desirably avoided or minimized, as well as on other factors including but not limited to viral titers, potency of infection (e.g., MOI), and other parameters. Oncolytic effects include any detectable parameter resulting from reoviral infection of and replication in a host tumor cell, leading to lysis of that cell. An attenuated reovirus thus may mediate an oncolytic effect by infecting a tumor cell and replicating within it, with accumulated progeny reoviruses eventually lysing it. Oncolytic mechanisms may include one or more of apoptosis, cell necrosis and cell lysis, which can be measured as described herein and in the cited publications, for purposes of determining whether a given candidate attenuated reovirus mediates an oncolytic effect (e.g., a statistically significant level of oncolysis has occurred).

A number of phenotypic characteristics of the attenuated reoviruses according to certain embodiments of the present invention relate to attenuated reoviruses that exhibit a decreased (e.g., with statistical significance relative to a wild-type reovirus) level of at least one detectable cytopathic effect toward a non-malignant cell relative to the level of the detectable cytopathic effect that is exhibited toward the non-malignant cell by a wild-type reovirus. Non-limiting examples of non-malignant cells for which the attenuated reoviruses have one or more decreased cytopathic effects include differentiated normal cells such as cardiac myocytes, pancreatic cells and endothelial cells, and undifferentiated stem cells such as embryonic stem cells and neural stem/progenitor cells.

A wide range of reoviral cytopathic effects can be detected, any one or more of which may be useful according to several of the herein disclosed embodiments, including identification, selection and/or characterization of the subject invention attenuated reovirus. These detectable cytopathic effects include apoptosis, necrosis, cytolytic viral replication, other altered cellular morphology, altered cell adhesion, altered cellular gene expression, altered cellular replication, and altered cellular metabolic activity.

Cells that are suspected of undergoing apoptosis or necrosis may be examined for morphological, permeability or other changes that are indicative of an apoptotic state or a necrotic state. For example by way of illustration and not limitation, apoptosis in many cell types may cause altered morphological appearance such as plasma membrane blebbing, cell shape change, loss of substrate adhesion properties or other morphological changes that can be readily detected by a person having ordinary skill in the art, for example by using light microscopy. As another example, cells undergoing apoptosis may exhibit fragmentation and disintegration of chromosomes, which may be apparent by microscopy and/or through the use of DNA-specific or chromatin-specific dyes that are known in the art, including fluorescent dyes. Apoptotic, necrotic and/or lysed cells may also exhibit altered plasma membrane permeability properties as may be readily detected through the use of vital dyes (e.g., propidium iodide, trypan blue) or by the detection of lactate dehydrogenase leakage into the extracellular milieu. These and other means for detecting apoptotic, necrotic and/or lysed cells by morphologic criteria, altered plasma membrane permeability and related changes will be apparent to those familiar with the art.

In another embodiment cells in a biological sample containing cells such as tumor cells suspected of undergoing apoptosis may be assayed for translocation of cell membrane phosphatidylserine (PS) from the inner to the outer leaflet of the plasma membrane, which may be detected, for example, by measuring outer leaflet binding by the PS-specific protein annexin. (Martin et al., 1995; Fadok et al, 1992). Alternatively, a cellular response to an apoptogen is determined by an assay for induction of specific protease activity in any member of a family of apoptosis-activated proteases known as the caspases (see, e.g., Green et al., 1998). Those having ordinary skill in the art will be readily familiar with methods for determining caspase activity, for example by determination of caspase-mediated cleavage of specifically recognized protein substrates. These substrates may include, for example, poly-(ADP-ribose) polymerase (PARP) or other naturally occurring or synthetic peptides and proteins cleaved by caspases that are known in the art (see, e.g., Ellerby et al., 1997). The synthetic peptide Z-Tyr-Val-Ala-Asp-AFC (SEQ ID NO:16), wherein "Z" indicates a benzoyl carbonyl moiety and AFC indicates 7-amino-4-trifluoromethylcoumarin (Kluck et al., 1997; Nicholson et al., 1995), is one such substrate. Other non-limiting examples of substrates include nuclear proteins such as U1-70 kDa and DNA-PKcs (Rosen and Casciola-Rosen, 1997; Cohen, 1997). Cellular apoptosis may also be detected by determination of cytochrome c that has escaped from mitochondria in apoptotic cells (e.g., Liu et al., 1996). Such detection of cytochrome c may be performed spectrophotometrically, immunochemically or by other well established methods for determining the presence of a specific protein. Persons having ordinary skill in the art will readily appreciate that there may be other suitable techniques for quantifying apoptosis or other detectable cytopathic effects.

II. METHODS OF TREATMENT

For use in methods of treating a malignant condition such as an activated oncogene-associated malignant condition, and in particular to achieve an oncolytic effect, in certain embodiments the present invention attenuated reovirus (as described above) may be formulated into pharmaceutical compositions for administration according to well known methodologies. Pharmaceutical compositions generally comprise one or more attenuated reoviruses as described herein, in combination with a pharmaceutically acceptable carrier, excipient or diluent. Such carriers will be nontoxic to recipients at the dosages and concentrations employed. Typically about 0.01 µg/kg to about 100 mg/kg body weight will be adminstered, typically by the intradermal, subcutaneous, intramuscular, intratumoral or intravenous route, or by other routes. A preferred dosage is about 1 µg/kg to about 1 mg/kg, with about 5 µg/kg to about 200 µg/kg particularly preferred. It will be evident to those skilled in the art that the number and frequency of administration will be dependent upon the response of the host, from which may be determined what is an effective amount. "Pharmaceutically acceptable carriers" for therapeutic use are well known in the pharmaceutical art, and are described, for example, in Remingtons Pharmaceutical Sciences, Mack Publishing Co., 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

The pharmaceutical compositions that contain one or more attenuated reoviruses may be in any form which allows for the composition to be administered to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal. The term parenteral as used herein includes subcutaneous injections, intravenous, intramuscular, intrasternal, intracavernous, intrathecal, intrameatal, intraurethral injection or infusion techniques. The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, preferred compositions contain, in addition to one or more attenuated reoviruses, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

It may also be desirable to include other components in the preparation, such as delivery vehicles including but not limited to aluminum salts, water-in-oil emulsions, biodegradable oil vehicles, oil-in-water emulsions, biodegradable microcapsules, and liposomes. Examples of immunostimulatory substances (adjuvants) for use in such vehicles include N-acetylmuramyl-L-alanine-D-isoglutamine (MDP), lipopolysaccharides (LPS), glucan, IL-12, GM-CSF, gamma interferon and IL-15. In other embodiments, methods of treating a malignant condition that comprise administering the subject invention attenuated reovirus further comprise administering, simultaneously or sequentially and in any order, at least one of (i) an anti-cancer drug, which may be a chemotherapeutic agent, an antibody, a cytokine, a hormone, or a growth factor, and (ii) radiation therapy.

In other embodiments it may desirable to include immunosuppressant agents in the preparation or in separate preparations to be administered simultaneously or sequentially and in either order. Examples of immunosuppressive agents include cyclosporin, cortisone, cyclophosphamide, FK506 (tacrolimus), leflunomide and others with which those skilled in the art will be familiar. Without wishing to be bound by theory, in the context of oncolytic therapy wherein the attenuated reovirus exhibits a decreased level of at least one cytopathic effect toward a malignant cell relative to the level of the detectable cytopathic effect that is exhibited toward the non-malignant cell by a non-attenuated reovirus, desirably lower levels of such immunosuppressive agents may be needed when the attenuated reovirus is used.

In certain other embodiments, methods disclosed herein for treating a malignant condition, for example, an activated oncogene-associated malignant condition or other type of malignant condition, comprise administering an effective amount of an attenuated reovirus to a subject under conditions and for a time sufficient for the attenuated reovirus to mediate (e.g., induce, cause, turn on or participate in mechanisms of, or otherwise result in) an oncolytic effect, and may further comprise comprising administering, simultaneously or sequentially and in any order, at least one of (i) an anti-cancer drug that comprises an agent selected from a chemotherapeutic agent, an antibody, a cytokine, a hormone, and an apoptogen (an agent capable of inducing apoptosis), and (ii) radiation therapy. Uses of anti-cancer drugs (e.g., doxorubicin, etoposide, teniposide, methotrexate, cytarabine, cisplatin, bleomycin, and 5-fluorouracil) and/or radiation in multi-modal or combination therapies are known in the art, as described, for example, in Guner et al., 2003; Lammering et al., 2003; Marini et al. 2003; and Jendrossek et al., 2003; and apoptogenic activity has been described for many such anti-cancer drugs as well as for other proteins (including certain antibodies, cytokines and hormones) and ligands (e.g., Fas ligand) of cell surface "death receptors" (e.g., Bras et al., 2005; Herr et al., 2001, and references cited therein).

While any suitable carrier known to those of ordinary skill in the art may be employed in the pharmaceutical compositions of this invention, the type of carrier will vary depending on the mode of administration and whether a sustained release is desired. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109. In this regard, it is preferable that the microsphere be larger than approximately 25 microns.

Pharmaceutical compositions may also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, product is formulated as a lyophilizate using appropriate excipient solutions (e.g., sucrose) as diluents.

In addition to direct in vivo procedures, ex vivo procedures may be used in which cells are removed from a host, modified, and placed into the same or another host organism (e.g., a human patient or animal subject). It will be evident that one can utilize any of the compositions noted above for introduction of attenuated reoviruses into tissue cells in an ex vivo context. Protocols for viral infection of cells, and physical and chemical methods of uptake are well known in the art.

Accordingly, the present invention is useful for treating a patient having a malignant condition, or for treating a cell culture derived from such a patient. As used herein, the term "patient" refers to any warm-blooded animal, preferably a human. A patient may be afflicted with cancer or a malignant condition, or may be normal (i.e., free of detectable disease and infection). A "cell culture" includes any preparation amenable to ex vivo treatment, for example, a preparation containing hematopoietic cells or immunocompetent cells or isolated cells of the immune system (including, but not limited to, T cells, macrophages, monocytes, B cells and dendritic cells) or transplant or graft (e.g., autologous graft) cells or any other preparation for which ex vivo treatment may precede reintroduction in vivo. Such cells may be isolated by any of a variety of techniques well known to those of ordinary skill in the art (e.g., Ficoll-hypaque density centrifugation). The cells may (but need not) have been isolated from a patient afflicted with a malignant condition, and may be reintroduced into a patient after treatment.

A liquid composition intended for either parenteral or oral administration should contain an amount of attenuated reovirus such that a suitable dosage will be obtained. Typically, this amount is at least 0.01 wt % of attenuated reovirus in the composition. When intended for oral administration, this amount may be varied to be between 0.1 and about 70% of the weight of the composition. Preferred oral compositions contain between about 4% and about 50% of attenuated reovirus. Preferred compositions and preparations are prepared so that a parenteral dosage unit contains between 0.01 to 1% by weight of active agent.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the attenuated reovirus of from about 0.1 to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol. In the methods of the invention, the attenuated reovirus may be administered through use of insert(s), bead(s), timed-release formulation(s), patch(es) or fast-release formulation(s).

III. EXAMPLES

The following Examples are offered by way of illustration and not by way of limitation.

Example 1—Generation of Attenuated Reovirus by Persistent Human Reovirus Infection of a Cell Line A. Materials & Methods Standard laboratory procedures were adopted from Ausubel et al. (1989); Ausubel et al. (1993); Sambrook et al. (1989); Maniatis et al. (1982); Glover, 1985); Hames and Higgins (1985). All reagents were from Sigma-Aldrich (St. Louis, Mo.) unless otherwise noted.

Cell Lines and Viruses.

Human fibrosarcoma (HT1080), normal primary human foreskin fibroblast (Hs68), HeLa, murine L929 and human 293 cell lines were purchased from the American Type Culture Collection (ATCC, Manassas, Va.). The cells were maintained according to ATCC protocols. The resistant cell line (HTR1) derived from HT1080 cells was maintained for more than 36 months. The Dearing strain of reovirus serotype 3 used in these studies was propagated in suspension cultures of L929 cells and purified according to Smith et al. (1969) with the exception that β-mercaptoethanol was omitted from the extraction buffer. The attenuated reovirus (AV) was propagated in HT1080 and purified by the same method as used for the wild-type reovirus. Human adenovirus type 5 and human adenovirus type 5 variant (E1B region deleted) were kindly provided by Dr. P. Branton (McGill University, Montreal) and were prepared as described (Teodoro et al., 1994).

Immunoblot Analysis.

Cell lysates were prepared by sonication in a buffer containing 10 mM Tris (pH 7.4), 2 mM EDTA, 1% NP-40, 50 mM mercaptoethanol, 100 ug/ml leupeptin and 2 ug/ml aprotinin. The lysates were then cleared by centrifugation at 16,000×g for 15 min, normalized for protein amount, mixed with SDS sample buffer, boiled for 5 min and stored at −70° C. After separation by SDS-PAGE, proteins were transferred to nitrocellulose membranes and then detected by immunoblot hybridization. The primary antibodies (Abs) were as follows: anti-reovirus polyclonal Ab (Lee et al., 1981), anti-caspase 3 Ab (Ingenex, San Diego, Calif.), anti-PARP Ab (BD Biosciences, San Jose, Calif.), anti-XIAP Ab (Imgenex), anti-actin Ab, anti-phospho-PKR Ab (Cell Signaling, Beverly, Mass.), and anti-PKR Ab (Upstate Biotech, Waltham, Mass.). The secondary Abs were horseradish peroxidase-conjugated anti-mouse Ab or horseradish peroxidase-conjugated anti-rabbit Ab (Pierce Biotech, Rockford, Ill.).

DNA Sequencing and Ras Activity Assays.

To sequence the N-Ras genes of HT1080 and HTR1 cells in the region encompassing the mutant codon 61, PCR was performed using two primers specific for the second exon of N-Ras. The 5'-primer was

[SEQ ID NO: 17]
GGTGAAACCTGTTTGTTGGA and the 3'-primer was

[SEQ ID NO: 18]
ATACACAGAGGAAGCCTTCG

The 119-bp PCR product was acrylamide gel-purified and sequenced using a 377XL ABI DNA Sequencing instrument (ABI, Foster City, Calif.) according to the manufacturer's instructions. To sequence the S1 gene of the AV virus, viral dsRNA genes were first converted to cDNA by reverse transcription and PCR amplification using the 5'-primer

[SEQ ID NO: 19]
CATGAATTCATG GATCCTCGCCTACGTTAAGAAG and the 3'-primer

[SEQ ID NO: 20]
CAGAAGCTTCTGATCCTCACGTGAAACTACGC, then cloned into pBK-CMV vector (Stratagene, La Jolla, Calif.) with EcoRI and HindIII insertions. Sequences of S1 genes were determined by standard automated sequencing methods as above using T7 and T3 primers.

Ras.

Ras activity assays were performed using Ras activation assay kits according to the supplier's instructions (Upstate Biotech, Waltham, Mass.). To determine the level of activated Ras (GTP bound form), cell lysates were incubated with agarose beads conjugated with the Ras-Raf binding domain at 4° C. for 1 hr. The beads were collected, washed, resuspended in 4× sample buffer, and boiled for 5 min. The samples were then subjected to SDS-PAGE and blotted with anti-N-Ras antibody (Oncogene Research, San Diego, Calif.). To detect total Ras protein, cell lysates were directly subjected to SDS-PAGE and blotted with anti-N-Ras antibody.

Virus Titration.

Six-well plates of cells were infected with human reovirus type 3 at an MOI of 40 PFU/cell. After 45 min at 4° C., virus-binding solution was removed, fresh medium was added, and cells were incubated at 37° C. until the designated time points. Plates were then subjected to three rounds of freeze-thawing and supernatants were used for plaque titration on 293 cell monolayers.

MTT and Apoptotic Nucleosome Assays.

Cell viability was assessed by MTT assay (Mosmann, 1983). Cells were plated in triplicate in 96-well plates. Following reoviral challenge, 3-(4,5-dimethylthiazol-2-yl)-2,5-diphenyl tetrazolium bromide (MTT) in PBS was added to each well. After 2 hr, lysis buffer (20% SDS in dimethylformamide/doubly distilled $H_2O$ [50:50, v/v]) was added and plates were incubated overnight at 37° C. before absorbance readings. Fragmented nucleosomal DNA in cells undergoing apoptosis was detected using anti-histone-biotin and peroxidase conjugated anti-DNA antibodies in streptavidin-coated microplates provided by the Cell Death Detection ELISA Plus kit (Roche Applied Science, Laval, Quebec).

Flow Cytometry and Apoptosis Inducers.

Cells were trypsinized and fixed in cytofix/cytoperm solution (PharMingen, San Diego, Calif.). Rabbit anti-reovirus polyclonal antibody was conjugated with FITC (FluoReporter FITC Protein Labeling Kit, Molecular Probes, Burlington, Ontario). The fixed and permeabilized cells were incubated with the FITC conjugated antibody and analyzed by flow cytometry. Detection of phosphatidylserine on the surfaces of apoptotic cells was performed using the Annexin-V-FITC detection kit (PharMingen, San Diego, Calif.). DNA fragmentation was assessed with the APO-BRDU kit (Sigma, Oakville, Ontario). FasL was purchased from Upstate Biotechnology (Waltham, Mass.) and camptothecin was from Biovision Research Products (Mountain View, Calif.).

RT-PCR Analysis.

RNA was extracted from cells using phenol:chloroform. Equal amounts of total cellular RNA from each sample were subjected to RT-PCR (Wong et al., 1994 Anal. Biochem. 223:251) using random hexanucleotide primers (Amersham, Piscataway, N.J.) and reverse transcriptase (Invitrogen, Burlington, Ontario). The cDNAs were then subjected to selective PCR of reovirus s1 using the primers

```
                                      [SEQ ID NO: 21]
    AATTCGATTTAGGTGACACTATAGCTATTGGTCGGATG
    and

[SEQ ID NO: 22]
    CCCTTTTGACAGTGATGCTCCGTTATCACTCG
``` that amplify a predicted 116 bp fragment. These primer sequences were derived from the S1 sequence determined previously (Nagata et al., 1984). The GAPDH primers (Wong et al., 1994)

```
                                      [SEQ ID NO: 23]
    CGGAGTCAACGGATTTGGTCGTAT
    and

[SEQ ID NO: 24]
    AGCCTTCTCCATGGTGGTGAAGAC
``` were used to amplify a predicted 306 bp GAPDH fragment which served as a PCR and gel loading control. Amplification of the s1 and GAPDH cDNAs was performed using Taq DNA polymerase (Invitrogen, Burlington, Ontario) using a Perkin Elmer Gene Amp PCR system 9600 (Perkin-Emer, Norwalk, Conn.). PCR was carried out for 28 cycles, with each cycle consisting of a denaturing step for 30 s at 97° C., an annealing step for 45 s at 55° C. and a polymerization step for 60 s at 72° C. PCR products were analyzed by electrophoresis through an ethidium bromide-impregnated TAE/2% agarose gel and photographed under UV illumination.

[$^{35}$S] Methionine Labelling and Immunoprecipitation.

70% confluent monolayers of HT1080, HTR1 and "cured" cells (HTR1 cells that were cured of persistent reoviral infection by growth in the presence of anti-reovirus antibody for three weeks according to procedures described in Dermody et al., 1995 and Ahmed et al., 1981) were infected with reovirus (MOI=40 PFU/cell). At 36 hrs post-infection, the medium was supplemented with 0.1 mCi/ml of [$^{35}$S] methionine. After further incubation for 12 hrs at 37° C., the cells were lysed in buffer containing 1% Triton X-100, 0.5% sodium deoxycholate and 1 mM EDTA. The nuclei were then removed by low-speed centrifugation and the supernatants were stored at −70° C. until use. Immunoprecipitation of $^{35}$S-labeled reovirus-infected cell lysates with anti-reovirus serotype 3 serum was carried out as previously described (Lee et al., 1981 Virology 108:134). In other experiments, 70% confluent monolayers of HT1080, HTR1 and Cured cells were infected with adenovirus type 5 and E1B deleted adenovirus type5 (MOI=20 PFU/cell). At 24 hr post-infection, the medium was supplemented with 0.1 mCi/ml of [$^{35}$S] methionine. After further incubation for 24 hrs at 37° C., the cells were lysed and subjected to SDS PAGE for autoradiography.

B. Results

Selection for Transformed Cells Resistant to Reovirus.

The HT1080 human fibrosarcoma cell line is heterozygous for an activating N-ras mutation (Gln to Lys at position 61) in its genome (Brown et al, 1984) and is exquisitely sensitive to reovirus (below). HT1080 cells were infected by human reovirus type 3 at multiplicities of infection (MOI) of 10-20. After 48-72 hr significant cytopathic effects were observed and MTT assays revealed that 80-95% of cells were dead; by one week fewer than $10^{-3}$ of the population was still alive; the remaining viable cells were allowed to grow over several weeks to 70-80% confluence, then infected again. Cells were serially infected 3 times to obtain highly resistant populations, from which 8 subclones were obtained by serial dilution.

Figure 1B:
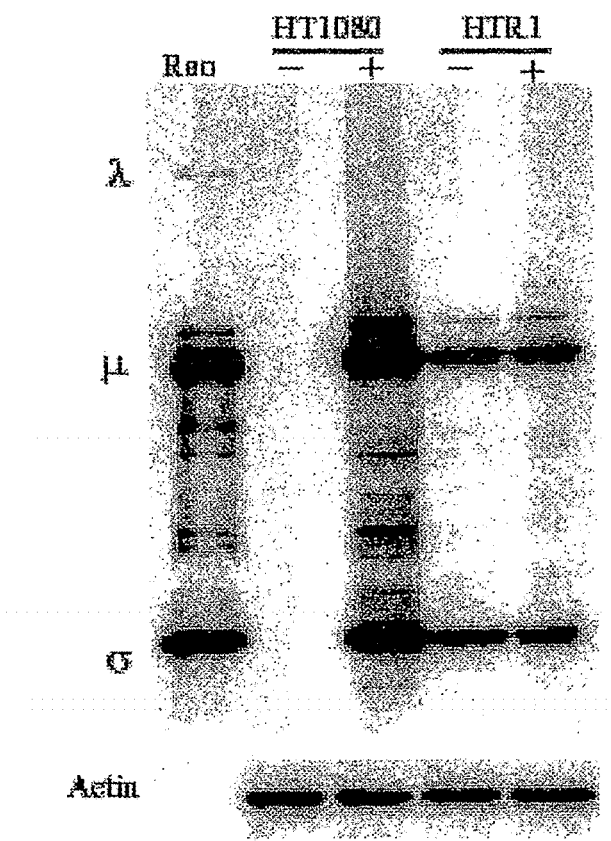

One clone designated HTR1 (other subclones were also tested and showed similar properties) was highly resistant to reovirus challenge even at high MOI of reovirus infection (FIG. 1A). Microsatellite DNA fingerprint analyses confirmed that the HTR1 cells were indeed derived from the HT1080 cells. The growth rate of the HTR1 cells was reduced; at first the cells grew very slowly but after several months they accelerated modestly, to approximately twice the doubling time compared to the parental cells. Consistent with their slowed growth, the HTR1 cells were persistently infected with reovirus as detected by Western blot analysis of cell lysates (FIG. 1B); the expression of viral proteins in the HTR1 cells was typically 10-20% of the level seen in HT1080 parental cells undergoing a lytic infection. Electron and deconvolution confocal microscopy of HTR1 cells was performed, with electron microscopy showing reoviral replicative factory activity near the nuclei of HTR1 cells and immunofluorescence staining with reoviral antigen-specific antibodies confirming the subcellular localization of such reoviral replicative factory activity in dividing HTR1 cells. From these results it was apparent that an adaptive response had arisen during the acquisition of viral resistance by the HTR1 cells.

Cellular Changes in the Resistant Cells.

Figure 2:
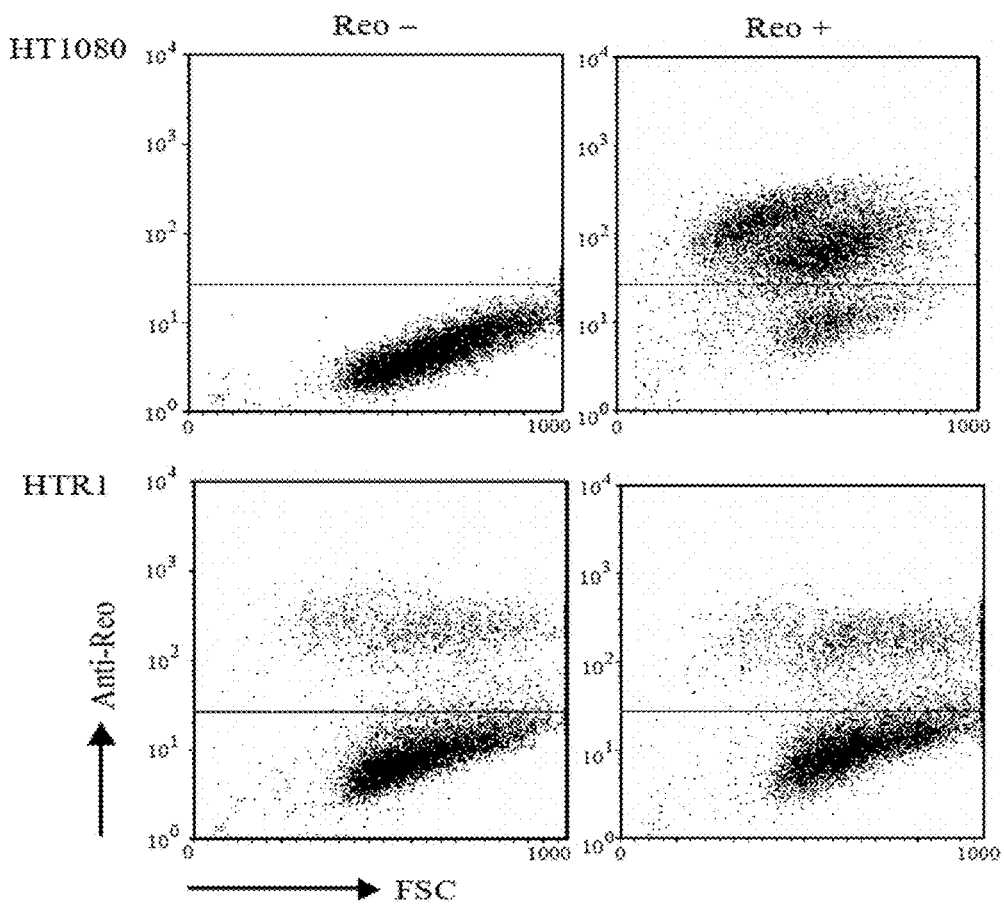
FIG. 2 shows impaired reovirus replication in selected reovirus-resistant cells with reduced cellular cathepsin B activity by flow cytometric analysis of HT1080 and HTR1 cells. HT1080 and HTR1 cells were either mock-infected (Reo −) or infected with reovirus (MOI=40 PFUs per cell) (Reo +), then, 48 hrs post-infection, cells were fixed, permeabilized and incubated with FITC conjugated anti-reovirus antibody. Reovirus antigens are detected by FACS scan.

Culture supernatants of the persistently infected clonal HTR1 cells were examined by plaque titration to determine how many viruses they produced. Functional reovirus was produced at up to $10^8$ plaque forming units per ml of culture supernatant, compared with $10^{10}$ PFUs per ml from parental HT1080 cells during a lytic infection. The HTR1 cells were then examined by flow cytometry using FITC conjugated anti-reovirus antibody to detect viral antigens. FIG. 2A shows that the subcloned HTR1 cell population was mixed in phenotype, with most cells showing minimal viral antigen expression and only a small portion expressing abundant antigens. Together with the observed reduction in viral protein synthesis in the HTR1 cell population (FIG. 1B), these results indicated that the HTR1 cells were capable of reovirus replication, albeit with a limited capacity.

Figure 3A:
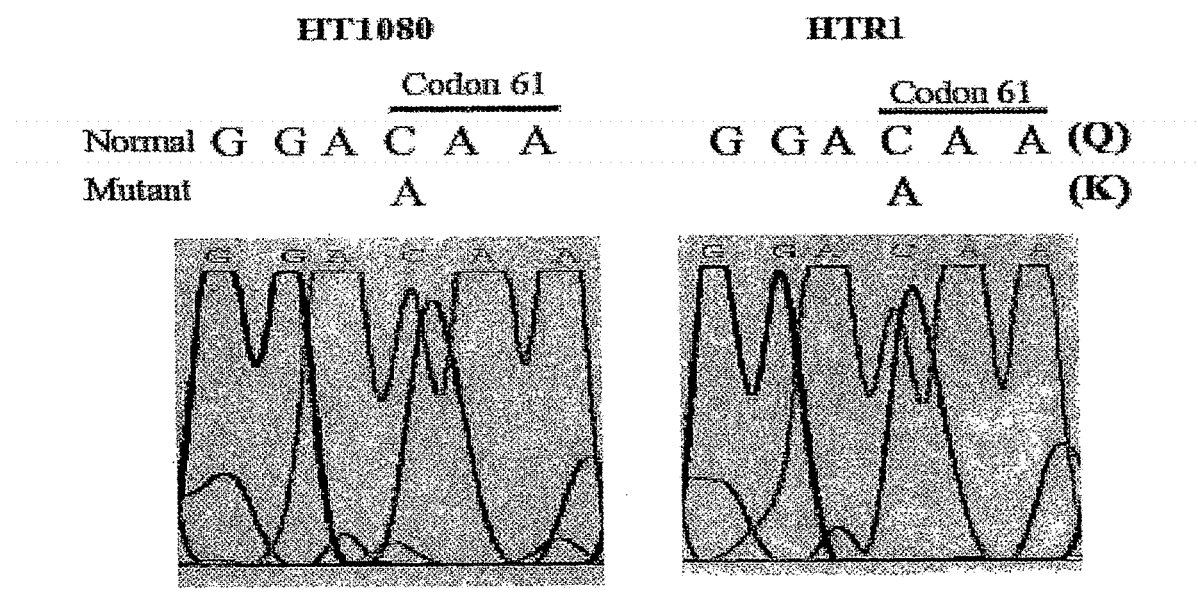
FIGS. 3A-B show analysis of HTR1 cells for Ras mutation and Ras activity.
Figure 3B:
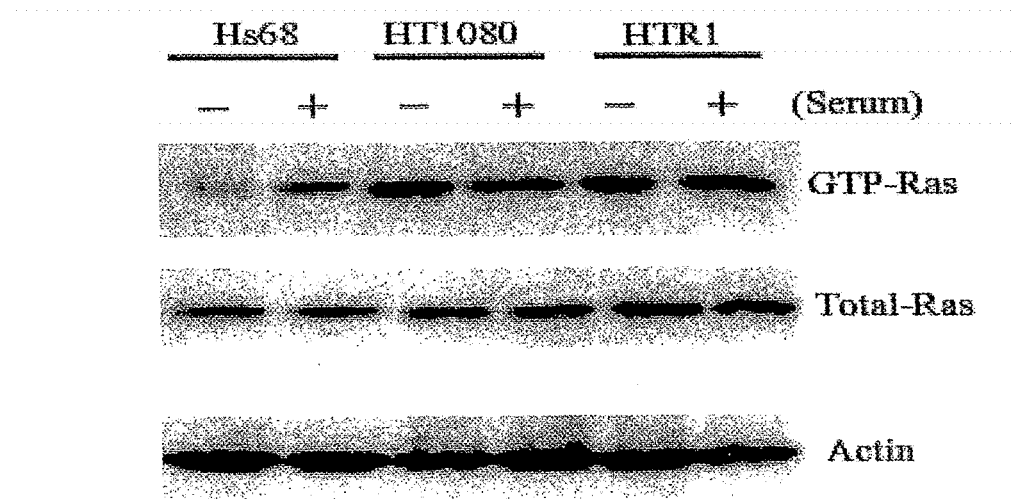

As discussed above, elevated activity in Ras or Ras-dependent pathways has previously been shown to be important in reoviral oncolysis (Strong et al., 1998). The possibility was considered that HTR1 cells might revert from high to low levels of Ras activity, thereby permitting the observed acquisition of the viral resistant phenotype. HT1080 cells, the parental cell line from which HTR1 cells were derived as described above, were earlier shown to contain an N-ras allele having a point mutation at codon 61 (Brown et al., 1984). Sequence analysis surrounding N-ras codon 61 was performed to determine whether HTR1 cells retained the N-ras mutation, and showed that both the HT1080 and the HTR1 genomes were heterozygous at that site (FIG. 3A). Therefore, N-ras reversion did not occur in HTR1 cells during the acquisition of viral resistance by HTR1. Ras activity was also assessed in parental and resistant cells using GST-Raf RBD (Ras Binding Domain) fusion protein conjugated to agarose beads; where Raf RBD has previously been shown to bind active Ras protein but not inactive isoforms (Vallee-Belisle et al., 2004). FIG. 3B shows that lysates from both the parental HT1080 and HTR1 cells had high constitutive Ras activity as evidenced by GST-Raf RBD binding. Thus, viral resistance by HTR1 cells was not the result of reduced Ras activity, nor of mutant-Ras reversions.

Apoptotic Responses of the Resistant Cells.

Figure 5A:
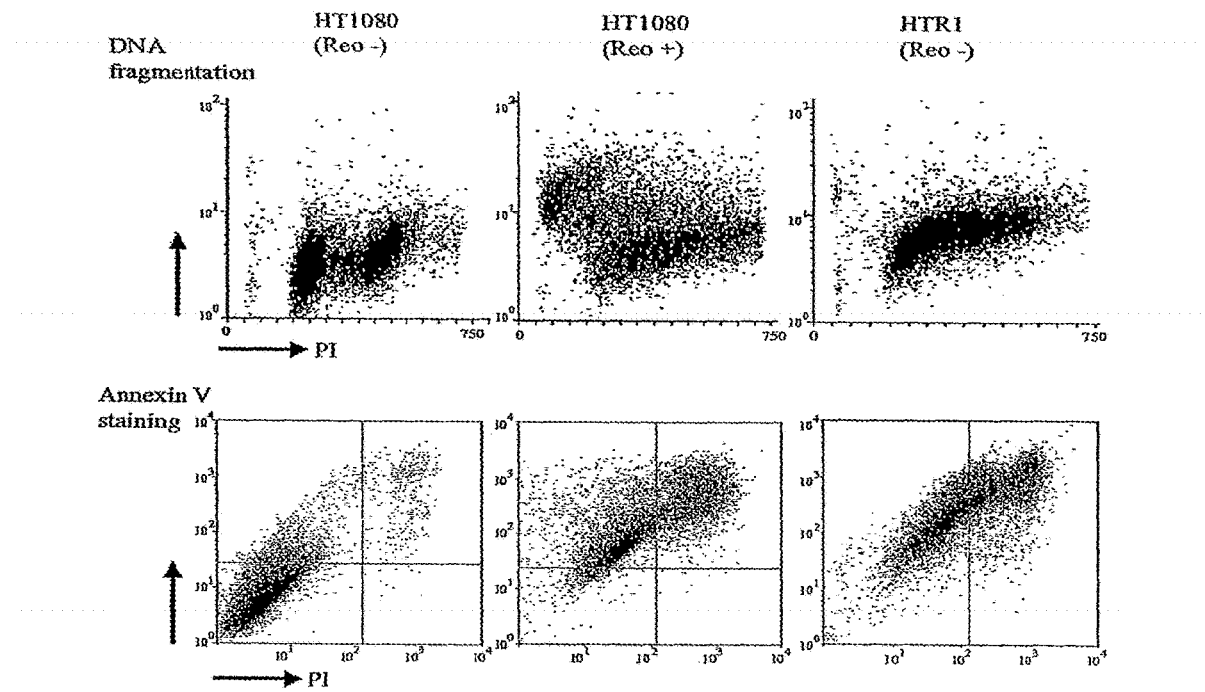
FIGS. 5A-F show that HTR1 cells were resistant to reovirus-induced apoptosis but susceptible to apoptotic inducers and adenovirus infection.
Figure 5B:
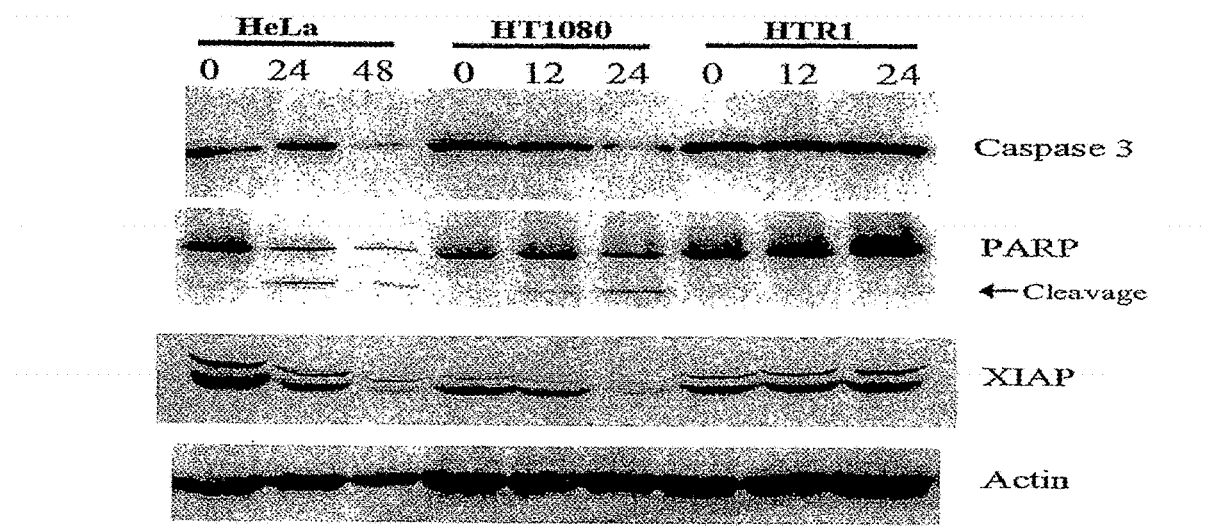

Reovirus has previously been shown to induce apoptosis in various cancer cells (Clarke et al., 2001). Hence, the capacity of HTR1 cells to undergo reovirus-induced apoptosis was examined as a possible mechanism of HTR1 resistance to virus. The apoptotic responses of the HTR1 cells upon reovirus infection were determined by several methods, including flow cytometric measures of Annexin V staining, DNA fragmentation assays and immunoblot analyses of proteins in apoptotic pathways. HTR1 cells showed significantly reduced indicia of apoptosis compared to the parental HT1080 cells upon reovirus challenge. As shown in FIG. 5A and FIG. 5B, the parental cells underwent DNA fragmentation, phosphatidyl serine (PS) externalization and caspase 3, PARP and XIAP cleavage upon reovirus infection, whereas the HTR1 cells did not exhibit significant apoptotic responses except for PS externalization (FIG. 5A, right panel).

Figure 5C:
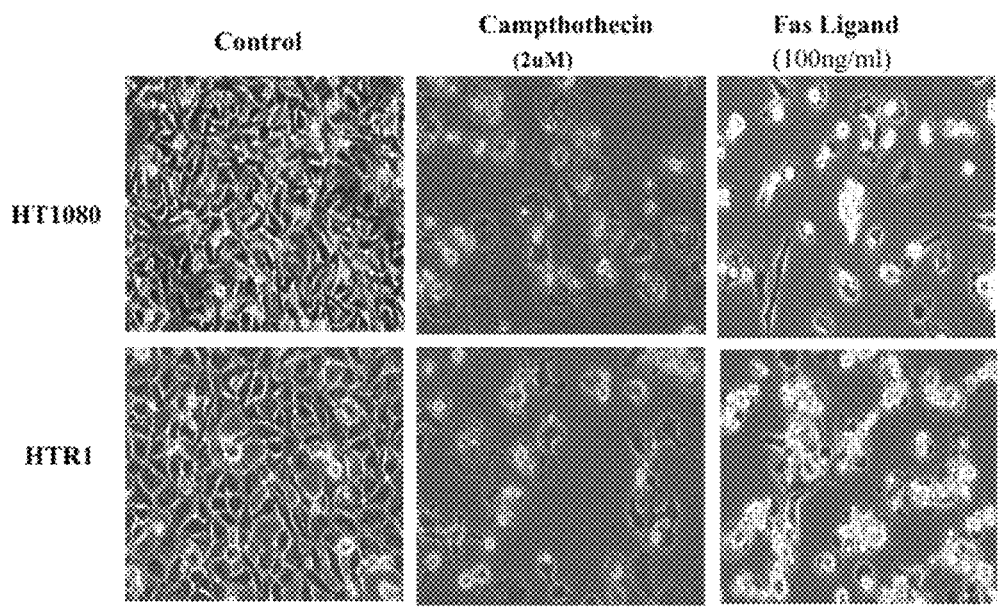
Figure 5D:
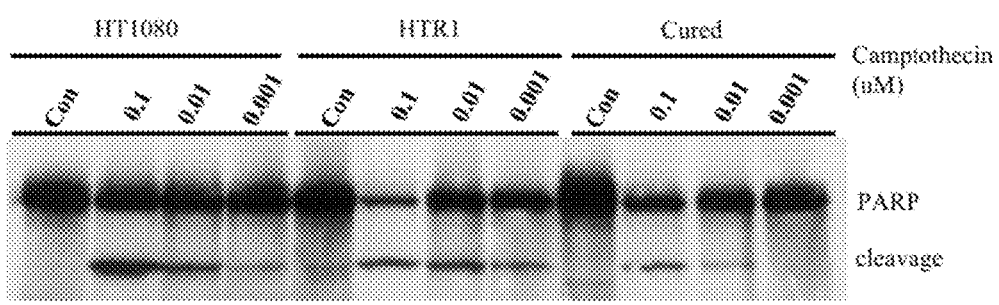
Figure 5E:
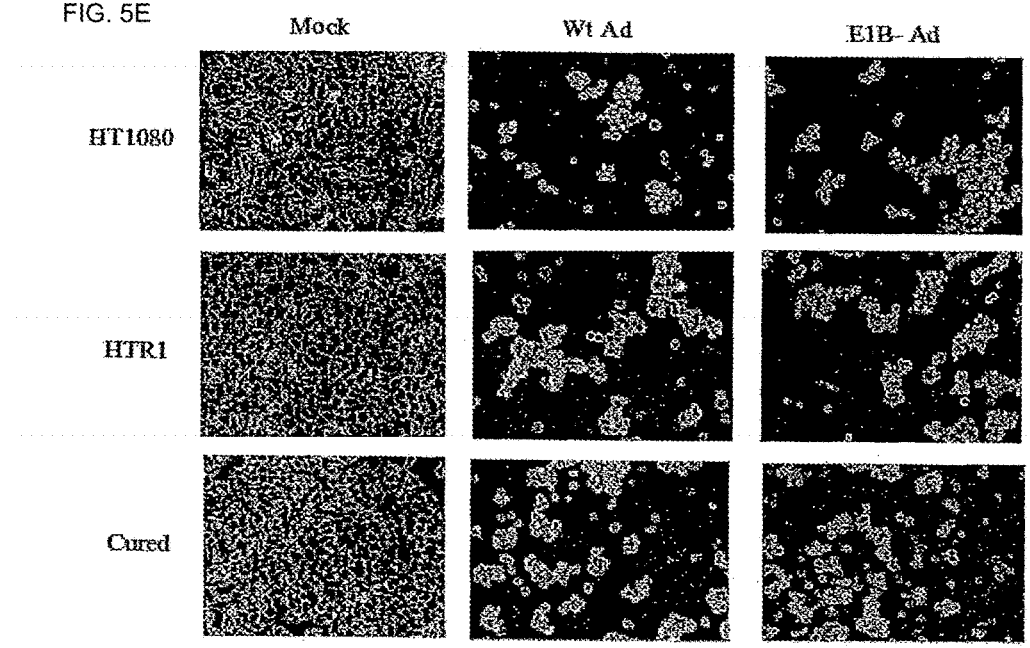
Figure 5F:
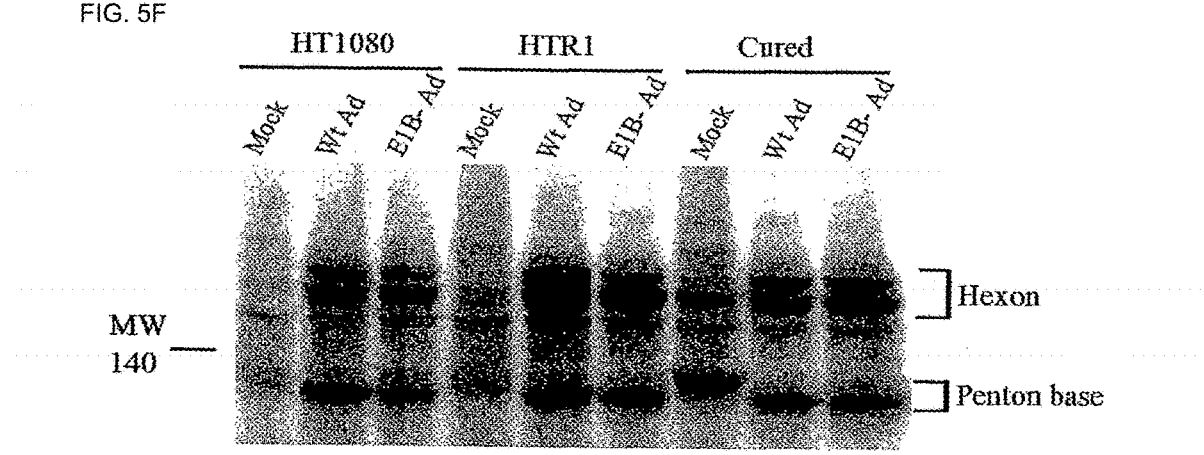

Other apoptotic inducers (apoptogens) were also tested for their ability to trigger apoptosis in the HTR1 cells. HTR1 and HT1080 cells displayed similar apoptotic responses to camptothecin and Fas ligand treatment (FIGS. 5C and 5D). In addition, HTR1 and HT1080 cells were similarly sensitive to challenge with wild-type or E1B compromised adenovirus, resulting in significant cell death and adenoviral protein synthesis (FIG. 5E and FIG. 5F). HTR1 cells thus apparently retained functional apoptotic pathways that can be triggered by chemical or adenoviral apotogenic agents.

Example 2—Characterization of Attenuated Reovirus

Figure 4A:
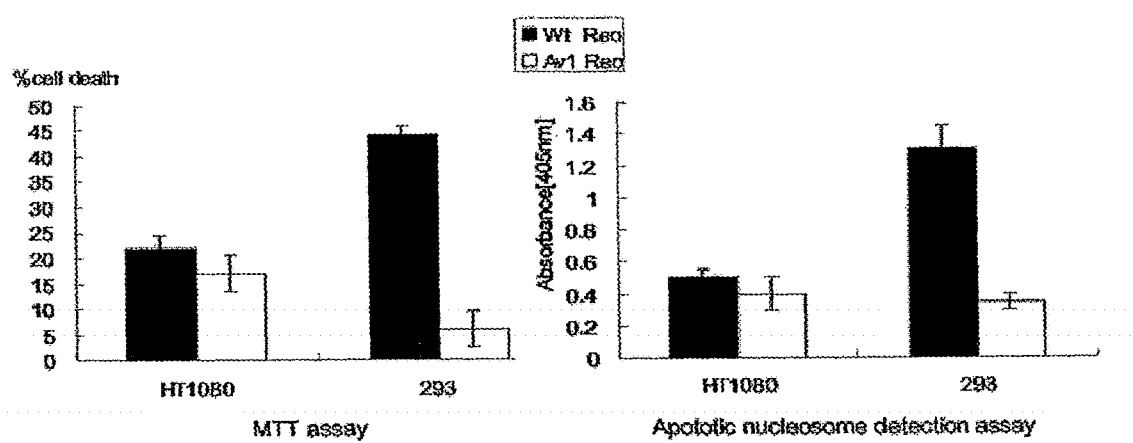
FIGS. 4A-C show differential cytopathic/apoptotic activity of attenuated reovirus.
Figure 4B:
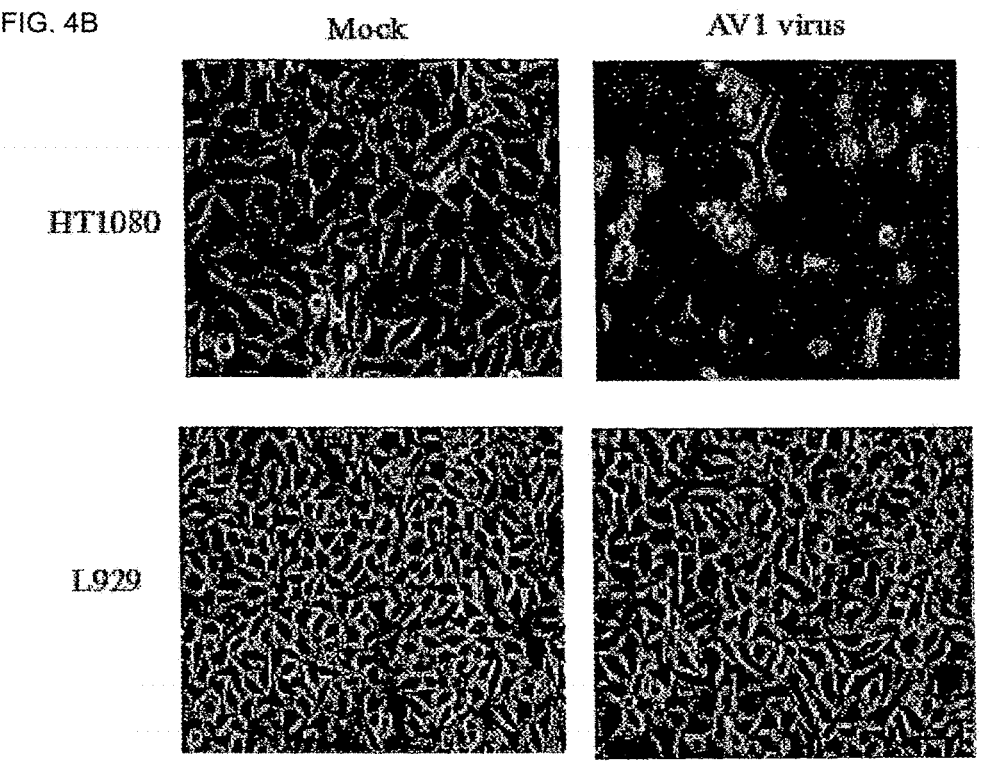
Figure 4C:
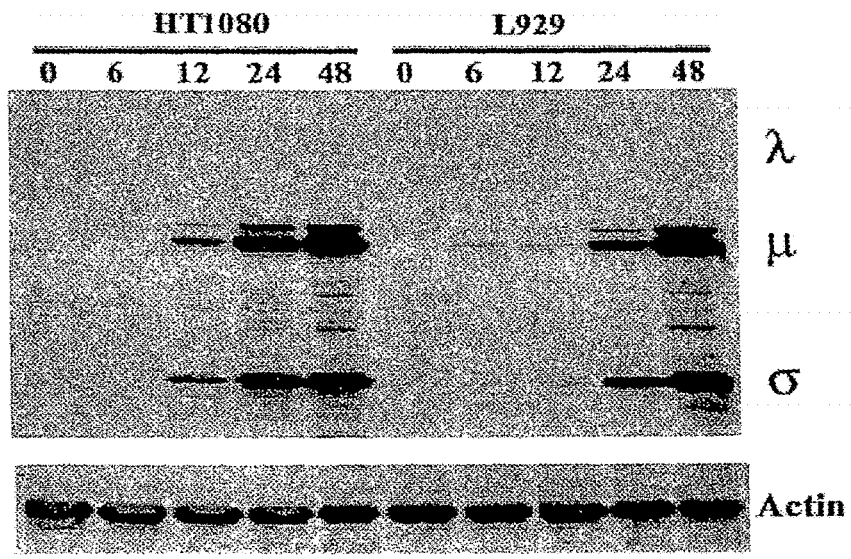
Figure 13:
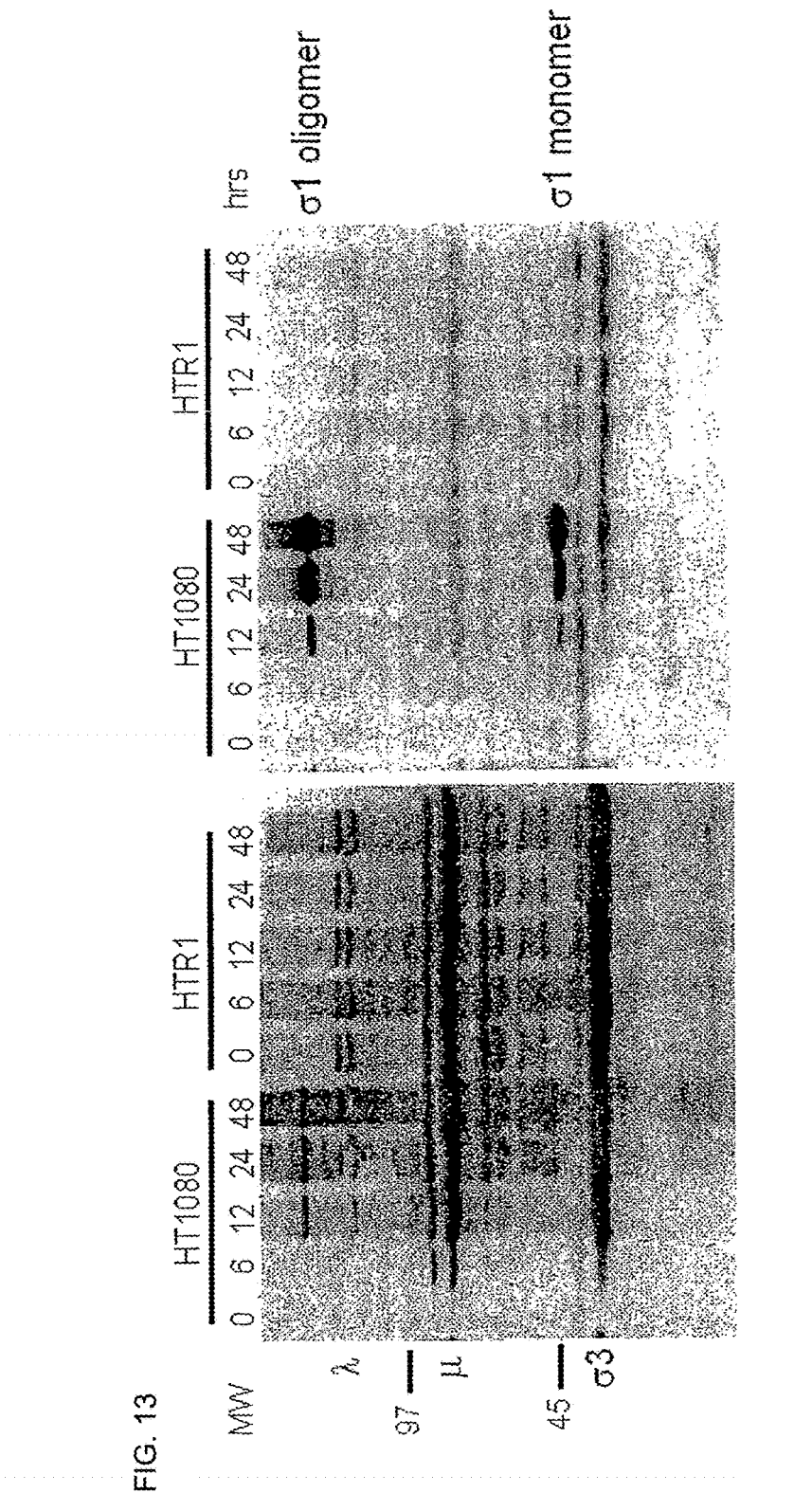
FIG. 13 shows comparison of detectable polypeptides from wild-type and attenuated reovirus. HT1080 and AV-expressing HTR1 cells grown to 70% confluency were either mock-infected or infected with reovirus (MOI=40 PFUs per cell). At each time point (hrs) following viral infection, cell lysates were prepared and examined by western blotting using anti-reovirus antibody (left panel). Then, the membrane was stripped and reblotted with anti-sigma1 antibody (right panel). In the attenuated reovirus (AV) expression of Sigma3 and other viral genes was not impaired (left panel), whereas Sigma1 expression by AV was significantly inhibited compared to the wild-type (WT) reovirus infected HT1080 cells (right panel).

Reovirus generated from the HTR1 cells as described in Example 1 was assessed for cytopathic activity toward parental HT1080 cells by exposing parental cells to supernatant medium prepared from cultured HTR1 cells. Significant cell death and viral protein synthesis were observed (FIGS. 4B, 4C), indicating that the reovirus generated from the resistant culture (HTR1) was still functional. Reovirus prepared from the resistant culture, designated as AV (Adapted Virus), showed differential apoptosis-inducing activity compared to the original laboratory strain wild-type reovirus. The AV virus showed significant cytopathic and apoptotic activity only with the parental HT1080 cells, but not with 293 cells or L929 cells (FIGS. 4A, 4B). Because the sigma 1 (σ1) protein of reovirus had demonstrated importance in reovirus-mediated apoptosis (Connolly et al., 2001), the S1 gene segment of the AV virus was sequenced and found to contain several mutations, including a deletion causing a reading frame shift and a premature stop codon in the N-terminus (Table 1). Biochemical analysis of AV polypeptides, including immunochemical analysis by western blotting (FIG. 13) revealed no detectable σ1 protein.

TABLE 1

Mutations in S1 gene nucleotide sequence of AV virus and corresponding mutations in deduced amino acid sequences of their σ1 protein and σ1s protein compared with wild-type (WT) reovirus lab variant shown in FIG. 8 [SEQ ID NOS: 9, 10, 11, 12]

| Location of mutations | | | |
|---|---|---|---|
| S1 gene | Sigma1 protein | Sigma1s protein | GenBank assession no. |
| 26, deletion | 5, Frame shift | — | AY860061 |
| 359, T→ C | 116, L→ P | — | |
| 392, T→ C | 127, V→ A | — | |
| 763, C→ T | 251, Q→ Stop | — | |
| 912, A→ G | 300, I→ M | — | |

In Table 1, mutation location numbers in the S1 gene refer to nucleotide sequence position; mutation location numbers in the sigma1 or sigma1s protein or refer to amino acid sequence position.

Similarly, because the S4 gene has been implicated in the maintenance of persistent reoviral infections in cell cultures (Ahmed et al., 1982; Wetzel et al., 1997; Baer et al., 1997) the S4 gene coding region of the attenuated reovirus (AV) was sequenced. As shown in Table 2, mutations in the σ3 protein region of S4 were also identified in the attenuated reovirus.

TABLE 2

Mutations in S4 gene nucleotide sequence of AV virus and corresponding mutations in deduced amino acid sequences of their σ3 protein, relative to the sequence of the wild-type (WT) reovirus lab variant shown in FIG. 12 [SEQ ID NOS: 13, 14, 15]

| Location of mutations | | GenBank |
|---|---|---|
| S4 gene | Sigma3 protein | assession no. |
| 562, C→ T | 45, S → F | |
| 784, A→ T | 119, H → L | |

In Table 2, mutation location numbers in the S4 gene refer to nucleotide sequence position; mutation location numbers in the sigma3 protein or refer to amino acid sequence position.

Example 3—In Vivo Tumorigenicity of HTR1 Cells Persistently Infected with an Attenuated Reovirus Materials and Methods were as described above in Example 1, with the addition of the following protocol for determining in vivo tumorigenicity of HTR1 cells, which produce AV, an exemplary attenuated reovirus: $5 \times 10^6$ cells of HT1080, HTR1, Cured (Dermody et al., 1995; Ahmed et al., 1981) and a mixture of HTR1 and Cured cells were suspended in 100 μl of PBS and injected into the left flanks of 6 to 8 week-old severe combined immunodeficient (SCID) mice (Charles River, Wilmington, Mass.). Mice were treated according to protocols approved by the University of Calgary Animal Care Committee. Tumor growth was monitored by weekly measurement. Mice were sacrificed when they had black tails caused by unconstrained reovirus-mediated pathology (Loken et al., 2004), or difficulty due to tumor burden. Tumors were fixed in 4% paraformaldehyde at room temperature, and tumor specimens were sent to the University of Calgary Histopathology Laboratory Research Service for routine histological analysis (H/E staining).

Figure 6A:
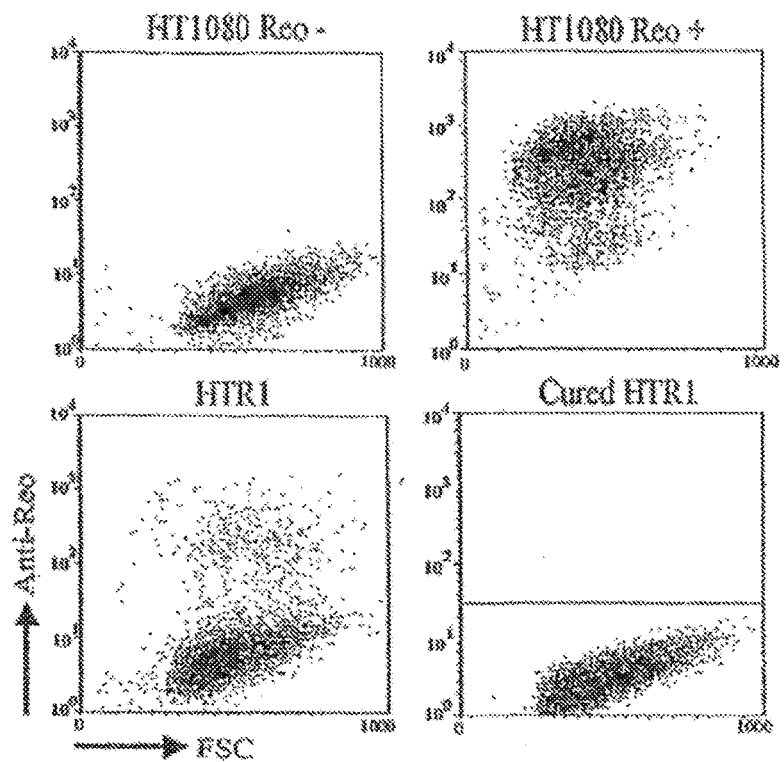
FIGS. 6A-B show in vitro curing of HTR1 cells.
Figure 6B:
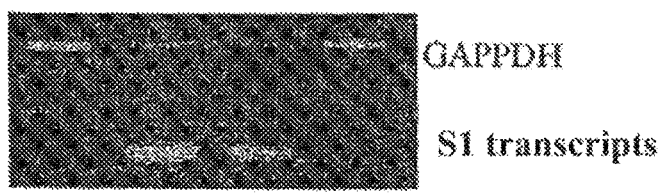
Figure 7A:
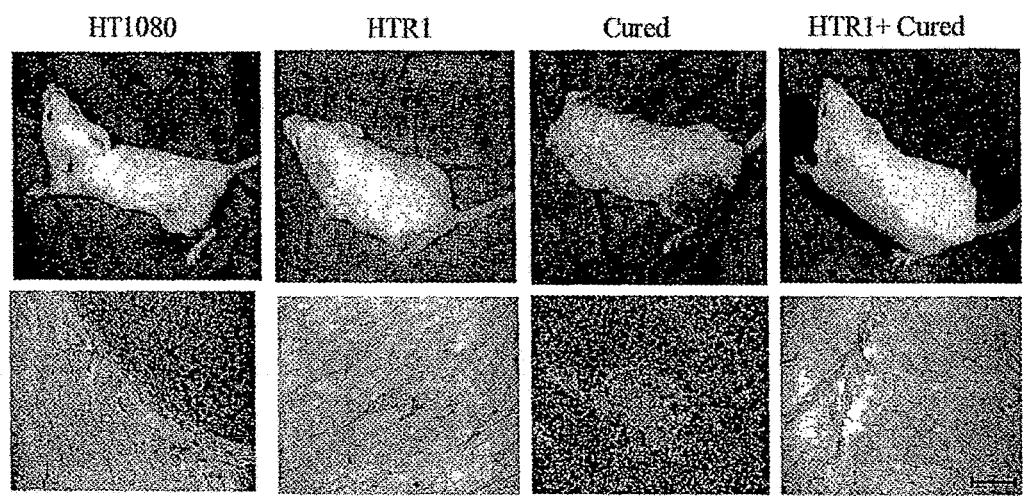
FIGS. 7A-B show tumorigenicity in vivo of HT1080, HTR1 and Cured cells.
Figure 7B:
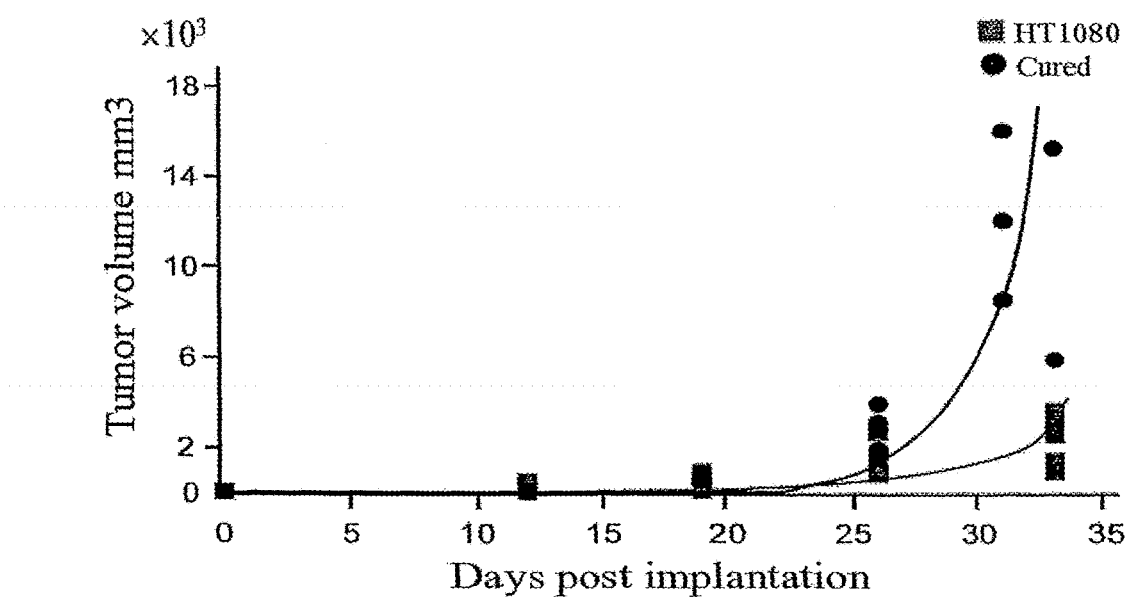

Both persistently infected (HTR1) and 'cured' HTR1 cells were tested for tumor formation in SCID mice by xenograft subcutaneous injection of cell suspensions. HTR1 cells that were 'cured' of the persistent reoviral infection by growth in the presence of reovirus antibody for 3 weeks in vitro, as previously demonstrated by others (Dermody et al., 1995; Ahmed et al., 1981) yielded virus-free cells, as shown by the absence of viral antigen, viral protein synthesis and viral transcripts (FIGS. 6A-C). In sharp contrast to the highly tumorigenic parental (HT1080) and cured cells, the persistently infected (HTR1) cells were not tumorigenic in vivo (FIGS. 7A and 7B). Furthermore, the persistently infected cells were able to suppress the cured cells' tumorigenic activity when co-injected (FIG. 7A, right panel), suggesting that reoviral persistence can have an ongoing role in tumor suppression. In fact, both the HTR1-implanted and the (HTR1-plus-cured) co-implanted SCID mice formed black tails after 3-7 months implantation without any tumor formation. Black tail formation was regarded as a manifestation of reovirus-mediated pathology in SCID mice (but not immunocompetent mice) and appeared within several weeks following wild-type reovirus infection (Loken et al., 2004). In a manner consistent with the suppression of tumor growth, the AV (an attenuated reovirus) thus persisted in mice for an extended period with reduced cytopathicity.

Example 4—Cytopathogenicity and Oncolysis Mediated by Attenuated Reovirus

This example describes cytopathogenic and oncolytic activities of an attenuated reovirus, and comparison of such activities to those of a wild-type reovirus.

Figure 9:
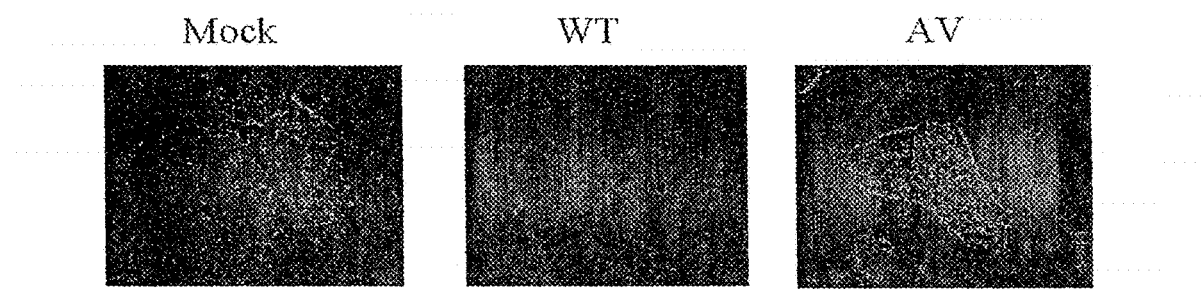
FIG. 9 shows a comparison of cytopathogenicity in murine embryonic stem cells induced by wild-type reovirus and by an attenuated reovirus.

Murine embryonic stem cells (MES2) were infected in vitro with either wild-type or AV (attenuated) reovirus obtained as described in Example 1, at a MOI of 40. Five days following infection, cytopathic effects of the cultures were observed via microscopy and representative fields photographed, as shown in FIG. 9. (Mock: Mock infection, WT: wild-type reovirus, AV: Attenuated reovirus) Wild-type reoviral infection resulted in pronounced cytopathic effects as evidenced by altered host cell morphology, while such effects were not apparent in cells infected with the attenuated reovirus.

Figure 10A:
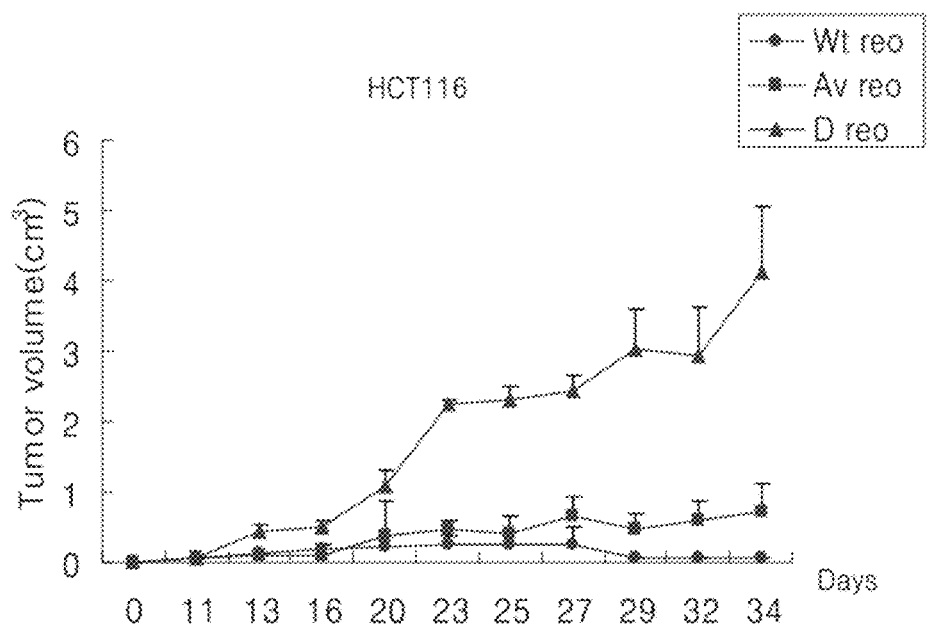
FIGS. 10A-B show a comparison of reoviral oncolysis and morbidity induced by wild-type reovirus and by an attenuated reovirus in an HT1080 human fibrosarcoma xenograft model.
Figure 10B:
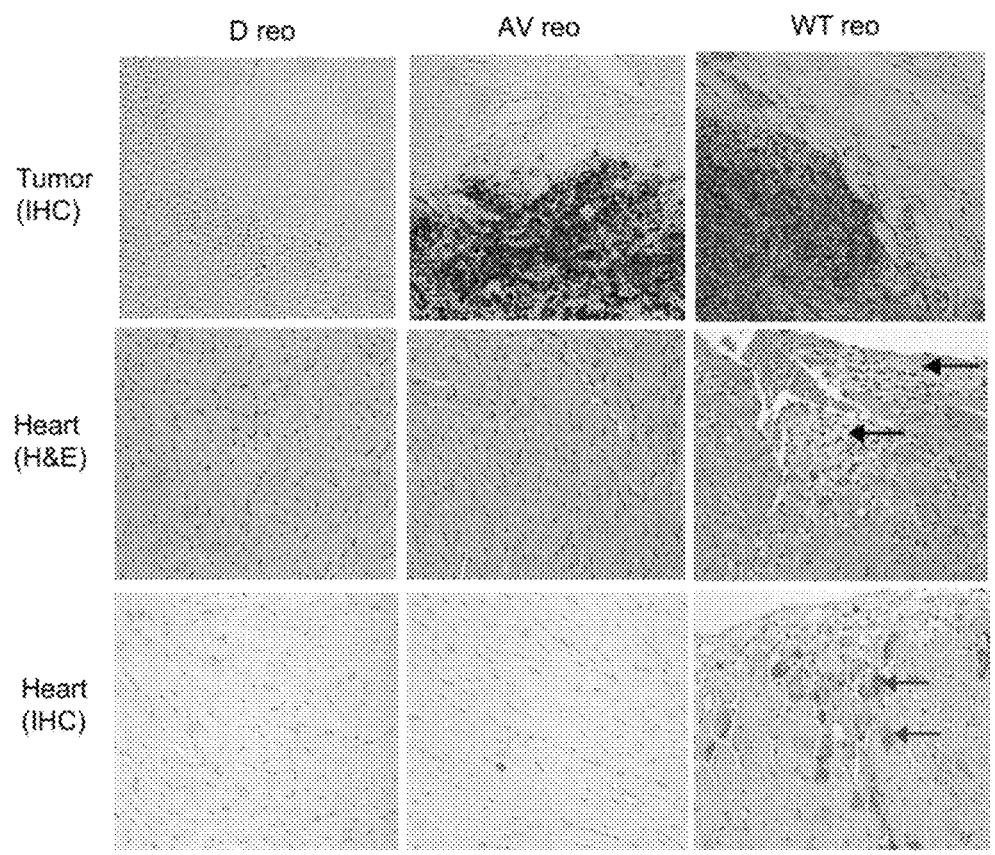

Reoviral oncolysis and morbidity were compared in an HT1080 xenograft model in SCID mice essentially according to procedures described in the preceding example. Attenuated reovirus (AV) exhibited viral replication, cytopathic effects in vitro, and oncolytic effects in vivo in HT1080 cells. As shown in FIGS. 10A-B, SCID mice received a single implantation of HT1080 human fibrosarcoma cells. Eleven days after implantation, tumors were injected with reoviruses (FIG. 10A; WT reo (wild-type reovirus), circle; n=6 tumor, AV reo (attenuated reovirus), rectangle: n=6 tumor, D reo (Dead, UV-inactivated reovirus), triangle: n=5 tumor) and tumor growth was followed up to 34 days post implantation. WT reovirus was injected additionally after 23 days post implantation. AV reovirus was injected additionally after 23 and 27 days post implantation.

FIG. 10B shows histological comparison of tumors treated with reoviruses (WT reo, AV reo, and D reo as described above). The paraffin sections of reovirus-treated tumors were analyzed by immune-staining with anti-reovirus antibody. Brown staining appeared as dark staining in black-and-white reproductions of photomicrographs and indicated reoviral protein positive areas in tumor sections, and the sections were counter-stained with hematoxylin (upper panel). The paraffin sections of hearts from reovirus-injected mice were also analyzed by H&E staining. Extensive necrotic lesions (arrows) are shown in cardiac myocytes of the wild-type reovirus-injected mice (lower panel) but were absent from attenuated reovirus-injected animals (lower panel, Av reo).

Figure 11A:
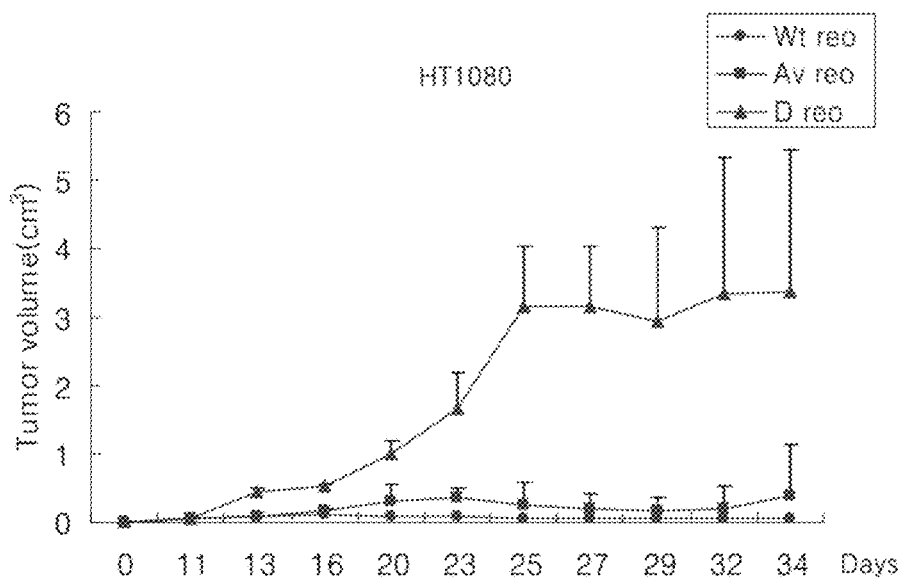
FIGS. 11A-B show a comparison of reoviral oncolysis and morbidity induced by wild-type reovirus and by an attenuated reovirus in an HCT116 human colon carcinoma xenograft model.
Figure 11B:
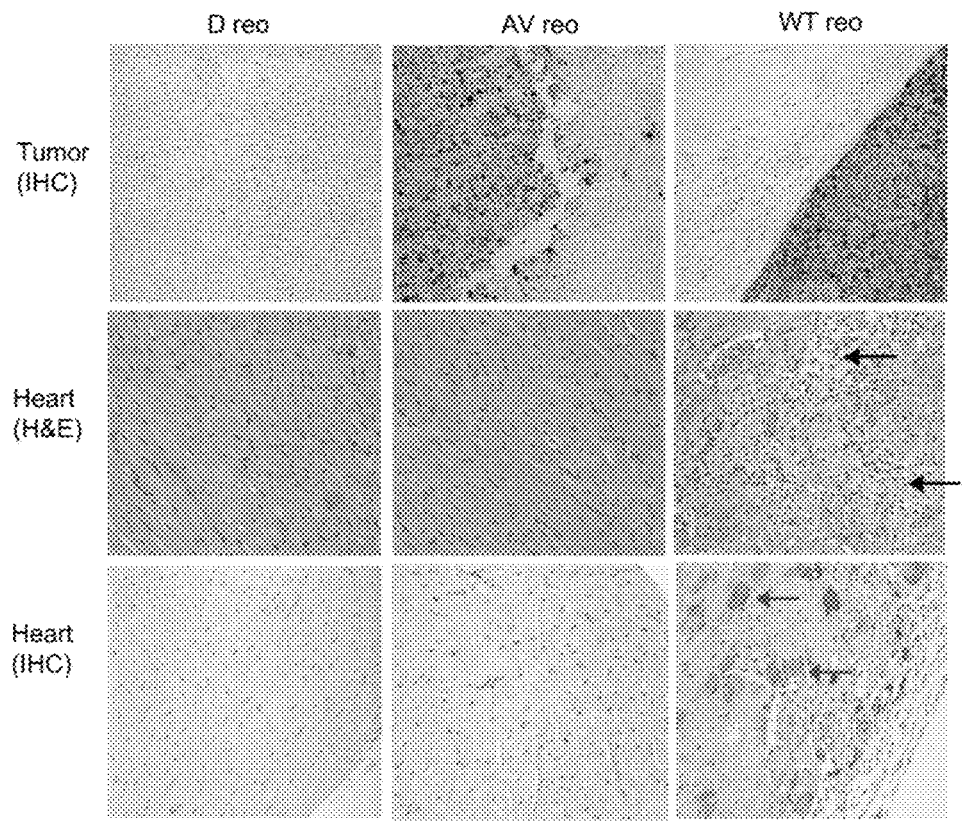

Reoviral oncolysis and morbidity were also compared in an HCT116 human colon carcinoma xenograft model in SCID mice essentially according to procedures described in the preceding example except using HCT116 cells (ATCC). Attenuated reovirus (AV) exhibited viral replication and oncolytic effects in vivo in HCT116 cells, but did not induce cytopathic effects in vitro. As shown in FIGS. 11A-B, SCID mouse received a single implantation of HCT116 cells. Eleven days after implantation, tumors were injected with reoviruses (FIG. 11A, WT reo, wild-type reovirus, circle; n=4 tumor, AV reo (attenuated reovirus), rectangle: n=4 tumor, D reo (Dead, UV-inactivated reovirus), triangle: n=4 tumor) and tumor growth was followed up to 34 days post implantation. WT reovirus was injected additionally after 23 days post implantation. AV reovirus was injected additionally after 23 and 27 days post implantation.

FIG. 11B shows histological comparison of tumors treated with reoviruses (WT reo, AV reo, and D reo as described above). The paraffin sections of reovirus-treated tumors were analyzed by immune-staining with anti-reovirus antibody. Brown staining appeared as dark staining in black-and-white reproductions of photomicrographs and indicated reoviral protein positive areas in tumor sections, and the sections were counter-stained with hematoxylin (upper panel). The paraffin sections of hearts from reovirus-injected mice were analyzed by H&E staining. Extensive necrotic lesions (arrows) are shown in cardiac myocytes of the wild-type reovirus-injected mice (lower panel) but were absent from attenuated reovirus-injected animals (lower panel, Av reo).

Example 5—Sequence Information

Genbank Accession numbers of Mammalian Reovirus type 1, 2, 3 S1 genes: AY860061 (Our AV Virus), AY862134, AY302467, NC_004264, NC_004267, XO1161, U74293, U74292, U74291, NC_004277, L37682, L37683, L37684, L37681, L37680, L37679, L37678, L37677, L37676, L37675, M14779, M10262, AH002408, J02326, J02325, M35964, AH002407, J02310, J02309, M35963, AH002406, J02302, J02301, U53415, U53414, U53413, U53412, U53411, U53410, U53409, M10261, All of the U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

REFERENCES

The references listed below are incorporated herein by reference to the extent that they supplement, explain, provide a background for, or teach methodology, techniques, and/or compositions employed herein.

U.S. Pat. No. 4,897,268
U.S. Pat. No. 5,075,109
U.S. Pat. No. 5,087,617
U.S. Pat. No. 5,093,246
U.S. Pat. No. 5,116,742
U.S. Pat. No. 5,135,917
U.S. Pat. No. 5,144,019
U.S. Pat. No. 5,168,053
U.S. Pat. No. 5,180,818
U.S. Pat. No. 5,190,931
U.S. Pat. No. 5,272,262
U.S. Pat. No. 6,110,461
U.S. Pat. No. 6,136,307
U.S. Pat. No. 6,261,555
U.S. Pat. No. 6,344,195
U.S. Pat. No. 6,455,038
U.S. Pat. No. 6,506,559
U.S. Pat. No. 6,528,305
U.S. Pat. No. 6,565,831
U.S. Pat. No. 6,576,234
U.S. Pat. No. 6,703,232
U.S. Pat. No. 6,808,916
U.S. Pat. No. 6,811,775
U.S. Publn. 2002/0168344
U.S. Publn. 2004/0126869
U.S. Publn. 2004/0146491
U.S. Publn. 2004/0265271
U.S. Publn. 2005/0019308
U.S. Publn. 2005/0026289
U.S. Publn. 2005/0063954
Ahmed et al., *Cell* 28:605, 1982.
Alain et al., *Blood*, 100:4146, 2002.
Altschul et al., *Nucl. Ac. Res.*, 25:3389, 1997.
Altschul, *J. Mol. Biol.*, 219:555, 1991.
Ausubel et al. In: *Current Protocols in Molecular Biology*, Greene Publ. Assoc. Inc. & John Wiley & Sons, Inc., MA, 1993.
Ausubel et al., In: *Current Protocols in Molecular Biology*, John Wiley & Sons, NY, 1989.
Baer et al., *J. Virol.*, 71:4921, 1997.
Bennefte et al., *Br. J. Expl Pathol.*, 48:267; 251, 1967.
Bernstein et al., *RNA*, 7:1509, 2001.
Bieniasz, *Nature Immunol.*, 5:1109, 2004.
Bishop, *Cell*, 42(1):23, 1985.
Bras et al., *Biochem. (Mosc.)*, 70:231, 2005.
Brown et al., *EMBO J.*, 3:1321, 1984.
Brown et al., *Gene Therapy*, 8:57, 2001.
Chandran et al., *J. Virol.* 73:3941, 1999.
Chandran et al., *J. Virol.* 75:5335, 2001.
Chappell et al., *J. Virol.*, 71:1834, 1997.
Chappell et al., *J. Virol.*, 74:8472, 2000.
Chiocca, *Nature Rev. Cancer*, 2:938, 2002.
Clarke et al., *Oncogene*, 20:6910, 2001.
Clusel et al., *Nucl. Acids Res.*, 21; 3405, 1993.
Coffey et al., *Science*, 282:1332, 1998.
Cohen, *Biochem. J.*, 326:1, 1997.
Connolly et al., *J. Virol.*, 75:4029, 2001.
Dermody et al., *J. Virol.*, 64:4842, 1990.
Dermody et al., *Virol.*, 212:272, 1995.
Dryden et al., *J. Cell Biol.* 1212:1023, 1993.
Duncan et al., *J. Virol.*, 28:444, 1978.
Duncan et al., *Virology*, 182:810, 1991.
Elbashir et al., *Nature*, 411:494, 2001.
Ellerby et al., *J. Neurosci.*, 17:6165, 1997.
Ernst et al., *Proc. Nat. Acad. Sci. USA*, 82:48, 1985.
Everts et al, *Cancer Gene Therap.*, 12:141, 2005.
Fadok et al., *J. Immunol.*, 148:2207, 1992.
Fernandes et al., *J. Biol. Chem.*, 269:17043, 1994.
Fire et al., *Nature*, 391:806-11, 1998.
Futreal et al., *Nat. Rev. Cancer*, 4:177, 2004.
Gee et al., In *Molecular and Immunologic Approaches*, Huber and Carr (Eds.), Futura Publishing Co., NY; 1994
Giantini et al., *J. Virol.*, 52:984, 1984.
Glover, In: *DNA Cloning*, Vol. I and II, IRL Press, Oxford, UK, 1985.
Green et al., *Science*, 281:1309, 1998.
Gummert et al., *J Am Soc. Nephrol.*, 10:1366, 1999.
Guner et al., *Curr. Med. Chem. Anticanc. Agents*, 3:319, 2003.
Hailer et al., *J. Virol.*, 69:357, 1995.
Hames and Higgins, In: *Nucleic Acid Hybridization*, IRL Press, Oxford, UK, 1985.
Harborth et al., *J. Cell Sci.*, 114:4557, 2001.
Hashiro et al., *Arch. Virol.*, 54:307, 1977.
Heggie et al., *Pediatr. Res.*, 13:937, 1979.
Henikoff et al., *Proc. Natl. Acad. Sci. USA*, 89:10915, 1992.
Herr et al., *Blood*, 98:260, 2001.
Hooper et al., *J. Virol.*, 70:459, 1996.
Hoyt et al., *J. Virol.*, 79:2743, 2005.
Jacobs et al., *Virology*, 147:9, 1985.
Jane-Valbuena et al., *J. Virol.* 73:2963, 1999.
Jendrossek et al., *Curr. Med. Chem. Anticanc. Agents*, 3:343, 2003.
Kaye et al., *J. Virol.*, 59:90, 1986.
Kluck et al., *Science*, 275:1132, 1997.
Lammering et al., *Curr. Med. Chem. Anticanc. Agents*, 3:327, 2003.
Larson et al., *Virology*, 201:303, 1994.
Lee et al., *BioEssays*, 16:199, 1994.
Lee et al., *Virology* 108:156
Lee et al., *Virology*, 108:134; 156, 1981.
Leone et al., *J. Biol. Chem.*, 271:8466, 1991.
Liu et al., *Cell*, 86:147, 1996.
Loken et al., *Cancer Biology & Therapy*, 3:734, 2004.
Mah et al., *Virology*, 179:95, 1990.
Maniatis et al., In: *Molecular Cloning*, Cold Spring Harbor Laboratory, NY, 1982.
Marini et al., *Curr. Med. Chem. Anticanc. Agents*, 3:334, 2003.
Martin et al., *J. Exp. Med.*, 182:1545, 1995.
Martinon, *Trends Immunol.*, 26:447, 2005.
Matzke et al., *Science*, 293:1080, 2001.
Monks et al., *J. Nat. Canc. Inst.* 83(11):757, 1991.
Mosmann, *J. Immunol. Meth.*, 65:55, 1983.
Nagata et al., *Nucl. Ac. Res.*, 12:8699, 1984.
Nagata et al., *Virology*, 160:162, 1987.
Nicholson et al., *Nature*, 376:37, 1995.
PCT Appln. WO 01/75164
PCT Appln. WO 99/32619
Philpott et al., *Mol. Immunol.*, 41:1099, 2004.
Plasterk, *Science*, 296:1263, 2002.
Priscott, *Br. J. Exp. Pathol.*, 64:467, 1983.
Remingtons Pharmaceutical Sciences, Mack Publishing Co., Gennaro (Ed.), 1985.
Rosen and Casciola-Rosen, *J. Cell. Biochem.*, 64:50, 1997.
Russell, *Cancer Gene Therapy*, 9:961, 2002.
Sambrook et al., In: *Molecular Cloning*, $2^{nd}$ Ed., Cold Spring Harbor Laboratory, NY, 1989.
Sarkar et al., *J. Virol.*, 54:720, 1985.
Scadden et al., *EMBO Rep.*, 2:1107, 2001.
Sharp, *Genes Dev.*, 13:139-41, 1999.
Sharp, *Genes Dev.*, 15:485, 2001.
Smith et al., *Virology*, 39:791, 1969.
Strong et al., *EMBO J.*, 17:3351, 1998.

Strong et al., *EMBO J.*, 17:3351, 1998.
Teodoro et al., *J. Virol.*, 68:776, 1994.
Turner et al., *Virology*, 186:219, 1992.
Tuschl, *Chembiochem.*, 2:239-245, 2001.
Tyler and Fields, In: *Fields' Virology*, Fields et al. (Eds.), Lippincott-Raven, Philadelphia, 1597-1623, 1996.
Vallee-Belisle et al., *Biochem.*, 43:8447, 2004.
Vogelstein et al., *Nat. Medicine*, 10:789, 2004.
Weiner et al., *J. Infect Dis.*, 141:609, 1980.
Wetzel et al., *J. Virol.* 71:1362, 1997.
Wiener et al., *Virol.*, 163:603, 1988.
Wilson et al., *J. Virol.*, 68:6458, 1994.
Wong et al., *Anal. Biochem.*, 223:251, 1994.
Zamore Nat. *Struct. Biol.*, 8:746, 2001.
Zamore, Science, 296:1265, 2002.

The invention claimed is:

1. An attenuated reovirus, comprising a reovirus genome that comprises a modification in the wild-type S1 gene, wherein the modification is selected from
   (a) a deletion of a nucleotide at nucleotide sequence position 26 of SEQ ID NO:1, SEQ ID NO:3, SEQ ID NO:9 or SEQ ID NO:10;
   (b) a mutation at nucleotide sequence position 359 of SEQ ID NO: 9 or SEQ ID NO:10;
   (c) a mutation at nucleotide sequence position 392 of SEQ ID NO: 9 or SEQ ID NO:10;
   (d) a mutation at nucleotide sequence position 763 of SEQ ID NO: 9 or SEQ ID NO:10; and
   (e) a mutation at nucleotide sequence position 912 of SEQ ID NO: 9 or SEQ ID NO:10, wherein the mutation at nucleotide sequence position 912 causes a substitution of isoleucine to methionine in the corresponding amino acid sequence.

2. The attenuated reovirus of claim 1, wherein the modification is the deletion of a nucleotide at nucleotide sequence position 26 of SEQ ID NO: 9 or SEQ ID NO:10.

3. The attenuated reovirus of claim 1, wherein the modification is the mutation at nucleotide sequence position 359 of SEQ ID NO: 9 or SEQ ID NO:10.

4. The attenuated reovirus of claim 3, wherein the mutation at nucleotide sequence position 359 causes a substitution of lysine to proline in the corresponding amino acid sequence.

5. The attenuated reovirus of claim 1, wherein the modification is the mutation at nucleotide sequence position 392 of SEQ ID NO:9 or SEQ ID NO:10.

6. The attenuated reovirus of claim 5, wherein the mutation at nucleotide sequence position 392 causes a substitution of valine to alanine in the corresponding amino acid sequence.

7. The attenuated reovirus of claim 1, wherein the modification is the mutation at nucleotide sequence position 763 of SEQ ID NO: 9 or SEQ ID NO:10.

8. The attenuated reovirus of claim 7, wherein the mutation at nucleotide sequence position 763 causes a substitution of glutamine to a stop codon in the corresponding amino acid sequence.

* * * * *

SEQUENCE LISTING

```
<160> NUMBER OF SEQ ID NOS: 24

<210> SEQ ID NO 1
<211> LENGTH: 1463
<212> TYPE: DNA
<213> ORGANISM: Mammalian orthoreovirus 1
<220> FEATURE:
<221> NAME/KEY: CDS
<222> LOCATION: (14)..(1426)

<400> SEQUENCE: 1
gctattcgcg cct atg gat gca tct ctc att aca gag ata cgg aaa ata        49
            Met Asp Ala Ser Leu Ile Thr Glu Ile Arg Lys Ile
            1               5                   10 gta ctc caa cta tct gta tca agc aat ggc tcc cag tca aaa gaa atc       97
Val Leu Gln Leu Ser Val Ser Ser Asn Gly Ser Gln Ser Lys Glu Ile
    15                  20                  25 gag gaa atc aag aaa caa gtc cag gtc aac gtt gat gat atc agg gct      145
Glu Glu Ile Lys Lys Gln Val Gln Val Asn Val Asp Asp Ile Arg Ala
30                  35                  40 gcc aat att aaa ctc gac gga ctt gga aga cag att gct gac atc agc      193
Ala Asn Ile Lys Leu Asp Gly Leu Gly Arg Gln Ile Ala Asp Ile Ser
45                  50                  55                  60 aat agc atc tca acc att gag tca aga ttg ggt gag atg gat aat cga      241
Asn Ser Ile Ser Thr Ile Glu Ser Arg Leu Gly Glu Met Asp Asn Arg
                65                  70                  75 ctt gtg ggt atc tcg agt cag gtc acg caa tta tct aac tca gtt agc      289
Leu Val Gly Ile Ser Ser Gln Val Thr Gln Leu Ser Asn Ser Val Ser
            80                  85                  90 cag aac act cag agc ata tcc tca ttg ggt gac aga atc aat gct gtc      337
Gln Asn Thr Gln Ser Ile Ser Ser Leu Gly Asp Arg Ile Asn Ala Val
        95                  100                 105 gaa cca cga gtt gac agt ctg gat acg gtc acg tct aat ctc act gga      385
Glu Pro Arg Val Asp Ser Leu Asp Thr Val Thr Ser Asn Leu Thr Gly
    110                 115                 120 cga aca tcc act ttg gag gca gat gtt gga agc tta cgg aca gaa cta      433
Arg Thr Ser Thr Leu Glu Ala Asp Val Gly Ser Leu Arg Thr Glu Leu
125                 130                 135                 140 gca gcg cta aca aca cgg gtg aca act gag gtt aca agg tta gat ggt      481
Ala Ala Leu Thr Thr Arg Val Thr Thr Glu Val Thr Arg Leu Asp Gly
                145                 150                 155 cta atc aat agt ggc cag aat tcg att ggt gag cta tcc aca aga cta      529
Leu Ile Asn Ser Gly Gln Asn Ser Ile Gly Glu Leu Ser Thr Arg Leu
            160                 165                 170 tcc aat gtg gag acg tct atg gtg acg acg gct gga cgg gga ctg cag      577
Ser Asn Val Glu Thr Ser Met Val Thr Thr Ala Gly Arg Gly Leu Gln
        175                 180                 185 aaa aac gga aac acc ttg aac gtc att gta ggt aat gga atg tgg ttt      625
Lys Asn Gly Asn Thr Leu Asn Val Ile Val Gly Asn Gly Met Trp Phe
    190                 195                 200 aat agt tct aat caa ttg cag ctc gac ctt tcg ggg caa tca aaa ggg      673
Asn Ser Ser Asn Gln Leu Gln Leu Asp Leu Ser Gly Gln Ser Lys Gly
205                 210                 215                 220
```

```
gtg gga ttt gtc ggc aca gga atg gtg gtt aag att gat act aat tat        721
Val Gly Phe Val Gly Thr Gly Met Val Val Lys Ile Asp Thr Asn Tyr
                225                 230                 235 ttt gct tac aat agt aat gga gag att aca ttg gtg agt caa atc aat        769
Phe Ala Tyr Asn Ser Asn Gly Glu Ile Thr Leu Val Ser Gln Ile Asn
            240                 245                 250 gaa ttg cca tcg cgc gta tca aca ctg gaa tca gcg aaa atc gat tca        817
Glu Leu Pro Ser Arg Val Ser Thr Leu Glu Ser Ala Lys Ile Asp Ser
        255                 260                 265 gtt tta cct cca tta acc gta cgc gaa gcg agc ggc gta cgt acc ctg        865
Val Leu Pro Pro Leu Thr Val Arg Glu Ala Ser Gly Val Arg Thr Leu
    270                 275                 280 agc ttt ggt tat gat acg agc gat ttt aca atc atc aac tcc gta ctg        913
Ser Phe Gly Tyr Asp Thr Ser Asp Phe Thr Ile Ile Asn Ser Val Leu
285                 290                 295                 300 tcg tta cgg tca cgt ttg act ctt ccg aca tac agg tac cct ctg gag        961
Ser Leu Arg Ser Arg Leu Thr Leu Pro Thr Tyr Arg Tyr Pro Leu Glu
                305                 310                 315 ctc gac aca gca aat aat aga gtg cag gtg gca gat cgt ttt ggc atg       1009
Leu Asp Thr Ala Asn Asn Arg Val Gln Val Ala Asp Arg Phe Gly Met
            320                 325                 330 cgc acg ggt act tgg acg gga caa ttg caa tat cag cac cca caa ttg       1057
Arg Thr Gly Thr Trp Thr Gly Gln Leu Gln Tyr Gln His Pro Gln Leu
        335                 340                 345 agt tgg aga gca aat gtc act ttg aat ttg atg aag gtg gat gat tgg       1105
Ser Trp Arg Ala Asn Val Thr Leu Asn Leu Met Lys Val Asp Asp Trp
    350                 355                 360 ttg gtg ttg agc ttt tct cag atg acg act aac tca ata atg gca gat       1153
Leu Val Leu Ser Phe Ser Gln Met Thr Thr Asn Ser Ile Met Ala Asp
365                 370                 375                 380 ggg aaa ttt gtg att aat ttt gtg tct ggg tta tct tct gga tgg cag       1201
Gly Lys Phe Val Ile Asn Phe Val Ser Gly Leu Ser Ser Gly Trp Gln
                385                 390                 395 acg ggg gat act gaa cca tcg tca act att gat cca tgg tct acg aca       1249
Thr Gly Asp Thr Glu Pro Ser Ser Thr Ile Asp Pro Trp Ser Thr Thr
            400                 405                 410 ttt gcc gcg gtc caa ttt cta aat aac ggt caa cgc att gat gcg ttt       1297
Phe Ala Ala Val Gln Phe Leu Asn Asn Gly Gln Arg Ile Asp Ala Phe
        415                 420                 425 agg atc atg gga gta tcg gaa tgg acg gat gga gaa tta gag att aag       1345
Arg Ile Met Gly Val Ser Glu Trp Thr Asp Gly Glu Leu Glu Ile Lys
    430                 435                 440 aat tat ggt ggc aca tac acc ggt cat act caa gta tat tgg gct ccg       1393
Asn Tyr Gly Gly Thr Tyr Thr Gly His Thr Gln Val Tyr Trp Ala Pro
445                 450                 455                 460 tgg acg atc atg tat cca tgc aat gtg agg tga atctagcgcg aaccctcggc    1446
Trp Thr Ile Met Tyr Pro Cys Asn Val Arg
                465                 470 acaaggggtc aatcatc                                                    1463

<210> SEQ ID NO 2
<211> LENGTH: 470
<212> TYPE: PRT
<213> ORGANISM: Mammalian orthoreovirus 1

<400> SEQUENCE: 2

Met Asp Ala Ser Leu Ile Thr Glu Ile Arg Lys Ile Val Leu Gln Leu
1               5                   10                  15

Ser Val Ser Ser Asn Gly Ser Gln Ser Lys Glu Ile Glu Glu Ile Lys
            20                  25                  30
```

```
Lys Gln Val Gln Val Asn Val Asp Asp Ile Arg Ala Ala Asn Ile Lys
         35                  40                  45
Leu Asp Gly Leu Gly Arg Gln Ile Ala Asp Ile Ser Asn Ser Ile Ser
 50                  55                  60
Thr Ile Glu Ser Arg Leu Gly Glu Met Asp Asn Arg Leu Val Gly Ile
 65                  70                  75                  80
Ser Ser Gln Val Thr Gln Leu Ser Asn Ser Val Ser Gln Asn Thr Gln
             85                  90                  95
Ser Ile Ser Ser Leu Gly Asp Arg Ile Asn Ala Val Glu Pro Arg Val
            100                 105                 110
Asp Ser Leu Asp Thr Val Thr Ser Asn Leu Thr Gly Arg Thr Ser Thr
            115                 120                 125
Leu Glu Ala Asp Val Gly Ser Leu Arg Thr Glu Leu Ala Ala Leu Thr
130                 135                 140
Thr Arg Val Thr Thr Glu Val Thr Arg Leu Asp Gly Leu Ile Asn Ser
145                 150                 155                 160
Gly Gln Asn Ser Ile Gly Glu Leu Ser Thr Arg Leu Ser Asn Val Glu
                165                 170                 175
Thr Ser Met Val Thr Ala Gly Arg Gly Leu Gln Lys Asn Gly Asn
            180                 185                 190
Thr Leu Asn Val Ile Val Gly Asn Gly Met Trp Phe Asn Ser Ser Asn
            195                 200                 205
Gln Leu Gln Leu Asp Leu Ser Gly Gln Ser Lys Gly Val Gly Phe Val
            210                 215                 220
Gly Thr Gly Met Val Val Lys Ile Asp Thr Asn Tyr Phe Ala Tyr Asn
225                 230                 235                 240
Ser Asn Gly Glu Ile Thr Leu Val Ser Gln Ile Asn Glu Leu Pro Ser
                245                 250                 255
Arg Val Ser Thr Leu Glu Ser Ala Lys Ile Asp Ser Val Leu Pro Pro
            260                 265                 270
Leu Thr Val Arg Glu Ala Ser Gly Val Arg Thr Leu Ser Phe Gly Tyr
            275                 280                 285
Asp Thr Ser Asp Phe Thr Ile Ile Asn Ser Val Leu Ser Leu Arg Ser
            290                 295                 300
Arg Leu Thr Leu Pro Thr Tyr Arg Tyr Pro Leu Glu Leu Asp Thr Ala
305                 310                 315                 320
Asn Asn Arg Val Gln Val Ala Asp Arg Phe Gly Met Arg Thr Gly Thr
                325                 330                 335
Trp Thr Gly Gln Leu Gln Tyr Gln His Pro Gln Leu Ser Trp Arg Ala
            340                 345                 350
Asn Val Thr Leu Asn Leu Met Lys Val Asp Asp Trp Leu Val Leu Ser
            355                 360                 365
Phe Ser Gln Met Thr Thr Asn Ser Ile Met Ala Asp Gly Lys Phe Val
370                 375                 380
Ile Asn Phe Val Ser Gly Leu Ser Ser Gly Trp Gln Thr Gly Asp Thr
385                 390                 395                 400
Glu Pro Ser Ser Thr Ile Asp Pro Trp Ser Thr Thr Phe Ala Ala Val
            405                 410                 415
Gln Phe Leu Asn Asn Gly Gln Arg Ile Asp Ala Phe Arg Ile Met Gly
            420                 425                 430
Val Ser Glu Trp Thr Asp Gly Glu Leu Glu Ile Lys Asn Tyr Gly Gly
            435                 440                 445
```

```
Thr Tyr Thr Gly His Thr Gln Val Tyr Trp Ala Pro Trp Thr Ile Met
    450                 455                 460
Tyr Pro Cys Asn Val Arg
465                 470

<210> SEQ ID NO 3
<211> LENGTH: 1440
<212> TYPE: DNA
<213> ORGANISM: Mammalian orthoreovirus 2
<220> FEATURE:
<221> NAME/KEY: CDS
<222> LOCATION: (14)..(1402)

<400> SEQUENCE: 3
gctattcgca ctc atg tcg gat cta gtg cag ctc ata aga agg gag atc        49
           Met Ser Asp Leu Val Gln Leu Ile Arg Arg Glu Ile
           1               5                   10 tta ctg tta act ggg aat gga gaa tca gcc aac tcg aaa cac gag atc       97
Leu Leu Leu Thr Gly Asn Gly Glu Ser Ala Asn Ser Lys His Glu Ile
        15                  20                  25 gag gaa att aag aaa caa att aaa gac atc tct gct gat gtc aac agg      145
Glu Glu Ile Lys Lys Gln Ile Lys Asp Ile Ser Ala Asp Val Asn Arg
    30                  35                  40 atc agt aac atc gtt gat tca atc caa gga caa ctg ggt gga tta tct      193
Ile Ser Asn Ile Val Asp Ser Ile Gln Gly Gln Leu Gly Gly Leu Ser
45                  50                  55                  60 gta cgc gtg tca gcc att gaa tcg gga gtt agt gag aac ggc aat cga      241
Val Arg Val Ser Ala Ile Glu Ser Gly Val Ser Glu Asn Gly Asn Arg
            65                  70                  75 att gat aga ctc gag cga gat gtc tcc ggc ata tcg gct agc gtt agc      289
Ile Asp Arg Leu Glu Arg Asp Val Ser Gly Ile Ser Ala Ser Val Ser
        80                  85                  90 gga atc gat tcg cgt tta tcc gag ctg ggt gac cga gtc aat gtt gca      337
Gly Ile Asp Ser Arg Leu Ser Glu Leu Gly Asp Arg Val Asn Val Ala
    95                  100                 105 gaa cag cga att ggc cag ttg gat aca gtc acg gat aat ctc ctt gag      385
Glu Gln Arg Ile Gly Gln Leu Asp Thr Val Thr Asp Asn Leu Leu Glu
110                 115                 120 cga gca tca aga ctg gaa act gaa gta tca gcc att act aat gac ctt      433
Arg Ala Ser Arg Leu Glu Thr Glu Val Ser Ala Ile Thr Asn Asp Leu
125                 130                 135                 140 gga tca ttg aat acg agg gtg acg act gaa ttg aac gat gtc cgc caa      481
Gly Ser Leu Asn Thr Arg Val Thr Thr Glu Leu Asn Asp Val Arg Gln
            145                 150                 155 act att gct gcg ata gac acg cgt ctc acg aca ctg gag acc gat gcc      529
Thr Ile Ala Ala Ile Asp Thr Arg Leu Thr Thr Leu Glu Thr Asp Ala
        160                 165                 170 gtg acg tcg gtt ggt caa ggg ctt cag aag act ggg aac tcg att aag      577
Val Thr Ser Val Gly Gln Gly Leu Gln Lys Thr Gly Asn Ser Ile Lys
    175                 180                 185 gtt att gtg ggt acg ggg atg tgg ttc gac cgc aat aat gtt ctg cag      625
Val Ile Val Gly Thr Gly Met Trp Phe Asp Arg Asn Asn Val Leu Gln
190                 195                 200 tta ttc gta tcg aac cag cag aaa ggg ttg gga ttc ata gac aat gga      673
Leu Phe Val Ser Asn Gln Gln Lys Gly Leu Gly Phe Ile Asp Asn Gly
205                 210                 215                 220 atg gta gtg aaa ata gat acc cag tat ttc agc ttc gat agc aat ggc      721
Met Val Val Lys Ile Asp Thr Gln Tyr Phe Ser Phe Asp Ser Asn Gly
            225                 230                 235 aac ata act ctg aac aac aac ata agt ggt ctg ccg gcg cga aca ggt      769
Asn Ile Thr Leu Asn Asn Asn Ile Ser Gly Leu Pro Ala Arg Thr Gly
```

```
                  240                 245                 250
tcc ctc gag gca tct cgt atc gat gtg gta gcg cca ccg ctt gtg ata    817
Ser Leu Glu Ala Ser Arg Ile Asp Val Val Ala Pro Pro Leu Val Ile
        255                 260                 265 cag tct act ggt agc act cgg cta ctg cgt ctc atg tac gag gct gtg    865
Gln Ser Thr Gly Ser Thr Arg Leu Leu Arg Leu Met Tyr Glu Ala Val
    270                 275                 280 gac ttc gtg gtt act aac aac gtt ctc aca ctg aga aat cga tcg gtc    913
Asp Phe Val Val Thr Asn Asn Val Leu Thr Leu Arg Asn Arg Ser Val
285                 290                 295                 300 acg cca aca ttc aag ttt cct ctg gag ttg aat agt gct gat aac tca    961
Thr Pro Thr Phe Lys Phe Pro Leu Glu Leu Asn Ser Ala Asp Asn Ser
            305                 310                 315 gtg agc att cat aga aat tac cgc att aga ctt ggg caa tgg tca ggt   1009
Val Ser Ile His Arg Asn Tyr Arg Ile Arg Leu Gly Gln Trp Ser Gly
        320                 325                 330 caa ttg gaa tat cac acg ccg agt ttg cgt tgg aat gct ccc gtc acg   1057
Gln Leu Glu Tyr His Thr Pro Ser Leu Arg Trp Asn Ala Pro Val Thr
    335                 340                 345 gtt aat ttg atg cga gta gac gat tgg ctc att ttg agt ttt act cgg   1105
Val Asn Leu Met Arg Val Asp Asp Trp Leu Ile Leu Ser Phe Thr Arg
350                 355                 360 ttt tcg acg agc ggc atc tta gcg tca gga aag ttt gta ttg aac ttc   1153
Phe Ser Thr Ser Gly Ile Leu Ala Ser Gly Lys Phe Val Leu Asn Phe
365                 370                 375                 380 gta act ggt ttg tct cca ggg tgg gcg act ggg agt acc gag ccc tcg   1201
Val Thr Gly Leu Ser Pro Gly Trp Ala Thr Gly Ser Thr Glu Pro Ser
        385                 390                 395 aca act act aac cca ctg tca acg acg ttt gct gca att cag ttc atc   1249
Thr Thr Thr Asn Pro Leu Ser Thr Thr Phe Ala Ala Ile Gln Phe Ile
    400                 405                 410 aat ggg tca tct cgc gta gac gcc ttt aga atc ttg gga gtc gca gag   1297
Asn Gly Ser Ser Arg Val Asp Ala Phe Arg Ile Leu Gly Val Ala Glu
            415                 420                 425 tgg aat gcc ggg gaa cta gag atc acg aat tat ggc gga aca tat aca   1345
Trp Asn Ala Gly Glu Leu Glu Ile Thr Asn Tyr Gly Gly Thr Tyr Thr
        430                 435                 440 gcg cat acc aat gtc gac tgg gcg ccg atg acc att atg tac cca tgt   1393
Ala His Thr Asn Val Asp Trp Ala Pro Met Thr Ile Met Tyr Pro Cys
445                 450                 455                 460 ctg ggc tga ggatccgggt gctccactcg gcacagtggc gactcatc              1440
Leu Gly

<210> SEQ ID NO 4
<211> LENGTH: 462
<212> TYPE: PRT
<213> ORGANISM: Mammalian orthoreovirus 2

<400> SEQUENCE: 4

Met Ser Asp Leu Val Gln Leu Ile Arg Arg Glu Ile Leu Leu Leu Thr
1               5                   10                  15

Gly Asn Gly Glu Ser Ala Asn Ser Lys His Glu Ile Glu Glu Ile Lys
            20                  25                  30

Lys Gln Ile Lys Asp Ile Ser Ala Asp Val Asn Arg Ile Ser Asn Ile
        35                  40                  45

Val Asp Ser Ile Gln Gly Gln Leu Gly Gly Leu Ser Val Arg Val Ser
    50                  55                  60

Ala Ile Glu Ser Gly Val Ser Glu Asn Gly Asn Arg Ile Asp Arg Leu
65                  70                  75                  80
```

Glu Arg Asp Val Ser Gly Ile Ser Ala Ser Val Ser Gly Ile Asp Ser
                85                  90                  95

Arg Leu Ser Glu Leu Gly Asp Arg Val Asn Val Ala Glu Gln Arg Ile
            100                 105                 110

Gly Gln Leu Asp Thr Val Thr Asp Asn Leu Leu Glu Arg Ala Ser Arg
        115                 120                 125

Leu Glu Thr Glu Val Ser Ala Ile Thr Asn Asp Leu Gly Ser Leu Asn
130                 135                 140

Thr Arg Val Thr Thr Glu Leu Asn Asp Val Arg Gln Thr Ile Ala Ala
145                 150                 155                 160

Ile Asp Thr Arg Leu Thr Thr Leu Glu Thr Asp Ala Val Thr Ser Val
                165                 170                 175

Gly Gln Gly Leu Gln Lys Thr Gly Asn Ser Ile Lys Val Ile Val Gly
            180                 185                 190

Thr Gly Met Trp Phe Asp Arg Asn Asn Val Leu Gln Leu Phe Val Ser
        195                 200                 205

Asn Gln Gln Lys Gly Leu Gly Phe Ile Asp Asn Gly Met Val Val Lys
210                 215                 220

Ile Asp Thr Gln Tyr Phe Ser Phe Asp Ser Asn Gly Asn Ile Thr Leu
225                 230                 235                 240

Asn Asn Asn Ile Ser Gly Leu Pro Ala Arg Thr Gly Ser Leu Glu Ala
                245                 250                 255

Ser Arg Ile Asp Val Val Ala Pro Pro Leu Val Ile Gln Ser Thr Gly
            260                 265                 270

Ser Thr Arg Leu Leu Arg Leu Met Tyr Glu Ala Val Asp Phe Val Val
        275                 280                 285

Thr Asn Asn Val Leu Thr Leu Arg Asn Arg Ser Val Thr Pro Thr Phe
290                 295                 300

Lys Phe Pro Leu Glu Leu Asn Ser Ala Asp Asn Ser Val Ser Ile His
305                 310                 315                 320

Arg Asn Tyr Arg Ile Arg Leu Gly Gln Trp Ser Gly Gln Leu Glu Tyr
                325                 330                 335

His Thr Pro Ser Leu Arg Trp Asn Ala Pro Val Thr Val Asn Leu Met
            340                 345                 350

Arg Val Asp Asp Trp Leu Ile Leu Ser Phe Thr Arg Phe Ser Thr Ser
        355                 360                 365

Gly Ile Leu Ala Ser Gly Lys Phe Val Leu Asn Phe Val Thr Gly Leu
370                 375                 380

Ser Pro Gly Trp Ala Thr Gly Ser Thr Glu Pro Ser Thr Thr Thr Asn
385                 390                 395                 400

Pro Leu Ser Thr Thr Phe Ala Ala Ile Gln Phe Ile Asn Gly Ser Ser
                405                 410                 415

Arg Val Asp Ala Phe Arg Ile Leu Gly Val Ala Glu Trp Asn Ala Gly
            420                 425                 430

Glu Leu Glu Ile Thr Asn Tyr Gly Gly Thr Tyr Thr Ala His Thr Asn
        435                 440                 445

Val Asp Trp Ala Pro Met Thr Ile Met Tyr Pro Cys Leu Gly
    450                 455                 460

<210> SEQ ID NO 5
<211> LENGTH: 1416
<212> TYPE: DNA
<213> ORGANISM: Mammalian orthoreovirus 3
<220> FEATURE:
<221> NAME/KEY: CDS

<222> LOCATION: (13)..(1380)

<400> SEQUENCE: 5

| | | | | | | | | | | | | | |
|---|---|---|---|---|---|---|---|---|---|---|---|---|---|
| gctattggtc gg | atg | gat | cct | cgc | cta | cgt | gaa | gaa | gta | gta | cgg | ctg | ata | 51 |
| | Met | Asp | Pro | Arg | Leu | Arg | Glu | Glu | Val | Val | Arg | Leu | Ile | |
| | 1 | | | | 5 | | | | | 10 | | | | |

| atc | gca | tta | acg | agt | gat | aat | gga | gca | tca | ctg | tca | aaa | ggg | ctt | gaa | 99 |
|---|---|---|---|---|---|---|---|---|---|---|---|---|---|---|---|---|
| Ile | Ala | Leu | Thr | Ser | Asp | Asn | Gly | Ala | Ser | Leu | Ser | Lys | Gly | Leu | Glu | |
| 15 | | | | | 20 | | | | | 25 | | | | | | |

| tca | agg | gtc | tcg | gcg | ctc | gag | aag | acg | tct | caa | ata | cac | tct | gat | act | 147 |
|---|---|---|---|---|---|---|---|---|---|---|---|---|---|---|---|---|
| Ser | Arg | Val | Ser | Ala | Leu | Glu | Lys | Thr | Ser | Gln | Ile | His | Ser | Asp | Thr | |
| 30 | | | | | 35 | | | | | 40 | | | | | 45 | |

| atc | ctc | cgg | atc | acc | cag | gga | ctc | gat | gat | gca | aac | aaa | cga | atc | atc | 195 |
|---|---|---|---|---|---|---|---|---|---|---|---|---|---|---|---|---|
| Ile | Leu | Arg | Ile | Thr | Gln | Gly | Leu | Asp | Asp | Ala | Asn | Lys | Arg | Ile | Ile | |
| | | | | 50 | | | | | 55 | | | | | 60 | | |

| gct | ctt | gag | caa | agt | cgg | gat | gac | ttg | gtt | gca | tca | gtc | agt | gat | gct | 243 |
|---|---|---|---|---|---|---|---|---|---|---|---|---|---|---|---|---|
| Ala | Leu | Glu | Gln | Ser | Arg | Asp | Asp | Leu | Val | Ala | Ser | Val | Ser | Asp | Ala | |
| | | 65 | | | | | 70 | | | | | 75 | | | | |

| caa | ctt | gca | atc | tcc | aga | ttg | gaa | agc | tct | atc | gga | gcc | ctc | caa | aca | 291 |
|---|---|---|---|---|---|---|---|---|---|---|---|---|---|---|---|---|
| Gln | Leu | Ala | Ile | Ser | Arg | Leu | Glu | Ser | Ser | Ile | Gly | Ala | Leu | Gln | Thr | |
| | 80 | | | | | 85 | | | | | 90 | | | | | |

| gtt | gtc | aat | gga | ctt | gat | tcg | agt | gtt | acc | cag | ttg | ggt | gct | cga | gtg | 339 |
|---|---|---|---|---|---|---|---|---|---|---|---|---|---|---|---|---|
| Val | Val | Asn | Gly | Leu | Asp | Ser | Ser | Val | Thr | Gln | Leu | Gly | Ala | Arg | Val | |
| 95 | | | | | 100 | | | | | 105 | | | | | | |

| gga | caa | ctt | gag | aca | gga | ctt | gca | gac | gta | cgc | gtt | gat | cac | gac | aat | 387 |
|---|---|---|---|---|---|---|---|---|---|---|---|---|---|---|---|---|
| Gly | Gln | Leu | Glu | Thr | Gly | Leu | Ala | Asp | Val | Arg | Val | Asp | His | Asp | Asn | |
| 110 | | | | | 115 | | | | | 120 | | | | | 125 | |

| ctc | gtt | gcg | aga | gtg | gat | act | gca | gaa | cgt | aac | att | gga | tca | ttg | acc | 435 |
|---|---|---|---|---|---|---|---|---|---|---|---|---|---|---|---|---|
| Leu | Val | Ala | Arg | Val | Asp | Thr | Ala | Glu | Arg | Asn | Ile | Gly | Ser | Leu | Thr | |
| | | | 130 | | | | | 135 | | | | | 140 | | | |

| act | gag | cta | tca | act | ctg | acg | tta | cga | gta | aca | tcc | ata | caa | gcg | gat | 483 |
|---|---|---|---|---|---|---|---|---|---|---|---|---|---|---|---|---|
| Thr | Glu | Leu | Ser | Thr | Leu | Thr | Leu | Arg | Val | Thr | Ser | Ile | Gln | Ala | Asp | |
| | | | 145 | | | | | 150 | | | | | 155 | | | |

| ttc | gaa | tct | agg | ata | tcc | acg | tta | gag | cgc | acg | gcg | gtc | act | agc | gcg | 531 |
|---|---|---|---|---|---|---|---|---|---|---|---|---|---|---|---|---|
| Phe | Glu | Ser | Arg | Ile | Ser | Thr | Leu | Glu | Arg | Thr | Ala | Val | Thr | Ser | Ala | |
| | 160 | | | | | 165 | | | | | 170 | | | | | |

| gga | gct | ccc | ctc | tca | atc | cgt | aat | aac | cgt | atg | acc | atg | gga | tta | aat | 579 |
|---|---|---|---|---|---|---|---|---|---|---|---|---|---|---|---|---|
| Gly | Ala | Pro | Leu | Ser | Ile | Arg | Asn | Asn | Arg | Met | Thr | Met | Gly | Leu | Asn | |
| 175 | | | | | 180 | | | | | 185 | | | | | | |

| gat | gga | ctc | acg | ttg | tca | ggg | aat | aat | ctc | gcc | atc | cga | ttg | cca | gga | 627 |
|---|---|---|---|---|---|---|---|---|---|---|---|---|---|---|---|---|
| Asp | Gly | Leu | Thr | Leu | Ser | Gly | Asn | Asn | Leu | Ala | Ile | Arg | Leu | Pro | Gly | |
| 190 | | | | | 195 | | | | | 200 | | | | | 205 | |

| aat | acg | ggt | ctg | aat | att | caa | aat | ggt | gga | ctt | cag | ttt | cga | ttt | aat | 675 |
|---|---|---|---|---|---|---|---|---|---|---|---|---|---|---|---|---|
| Asn | Thr | Gly | Leu | Asn | Ile | Gln | Asn | Gly | Gly | Leu | Gln | Phe | Arg | Phe | Asn | |
| | | | 210 | | | | | 215 | | | | | 220 | | | |

| act | gat | caa | ttc | cag | ata | gtt | aat | aat | aac | ttg | act | ctc | aag | acg | act | 723 |
|---|---|---|---|---|---|---|---|---|---|---|---|---|---|---|---|---|
| Thr | Asp | Gln | Phe | Gln | Ile | Val | Asn | Asn | Asn | Leu | Thr | Leu | Lys | Thr | Thr | |
| | | | 225 | | | | | 230 | | | | | 235 | | | |

| gtg | ttt | gat | tct | atc | aac | tca | agg | ata | ggc | gca | act | gag | caa | agt | tac | 771 |
|---|---|---|---|---|---|---|---|---|---|---|---|---|---|---|---|---|
| Val | Phe | Asp | Ser | Ile | Asn | Ser | Arg | Ile | Gly | Ala | Thr | Glu | Gln | Ser | Tyr | |
| | | 240 | | | | | 245 | | | | | 250 | | | | |

| gtg | gcg | tcg | gca | gtg | act | ccc | ttg | aga | tta | aac | agt | agc | acg | aag | gtg | 819 |
|---|---|---|---|---|---|---|---|---|---|---|---|---|---|---|---|---|
| Val | Ala | Ser | Ala | Val | Thr | Pro | Leu | Arg | Leu | Asn | Ser | Ser | Thr | Lys | Val | |
| | 255 | | | | | 260 | | | | | 265 | | | | | |

| ctg | gat | atg | cta | ata | gac | agt | tca | aca | ctt | gaa | att | aat | tct | agt | gga | 867 |
|---|---|---|---|---|---|---|---|---|---|---|---|---|---|---|---|---|
| Leu | Asp | Met | Leu | Ile | Asp | Ser | Ser | Thr | Leu | Glu | Ile | Asn | Ser | Ser | Gly | |
| 270 | | | | | 275 | | | | | 280 | | | | | 285 | |

| cag | cta | act | gtt | aga | tcg | aca | tcc | ccg | aat | ttg | agg | tat | ccg | ata | gct | 915 |
|---|---|---|---|---|---|---|---|---|---|---|---|---|---|---|---|---|
| Gln | Leu | Thr | Val | Arg | Ser | Thr | Ser | Pro | Asn | Leu | Arg | Tyr | Pro | Ile | Ala | |
| | | | 290 | | | | | 295 | | | | | 300 | | | |

```
gat gtt agc ggc ggt atc gga atg agt cca aat tat agg ttt agg cag       963
Asp Val Ser Gly Gly Ile Gly Met Ser Pro Asn Tyr Arg Phe Arg Gln
            305                 310                 315 agc atg tgg ata gga att gtc tcc tat tct ggt agt ggg ctg aat tgg      1011
Ser Met Trp Ile Gly Ile Val Ser Tyr Ser Gly Ser Gly Leu Asn Trp
        320                 325                 330 agg gta cag gtg aac tcc gac att ttt att gta gat gat tac ata cat      1059
Arg Val Gln Val Asn Ser Asp Ile Phe Ile Val Asp Asp Tyr Ile His
    335                 340                 345 ata tgt ctt cca gct ttt gac ggt ttc tct ata gct gac ggt gga gat      1107
Ile Cys Leu Pro Ala Phe Asp Gly Phe Ser Ile Ala Asp Gly Gly Asp
350                 355                 360                 365 cta tcg ttg aac ttt gtt acc gga ttg tta cca ccg tta ctt aca gga      1155
Leu Ser Leu Asn Phe Val Thr Gly Leu Leu Pro Pro Leu Leu Thr Gly
                370                 375                 380 gac act gag ccc gct ttt cat aat gac gtg gtc aca tat gga gca cag      1203
Asp Thr Glu Pro Ala Phe His Asn Asp Val Val Thr Tyr Gly Ala Gln
            385                 390                 395 act gta gct ata ggg ttg tcg tcg ggt ggt gcg cct cag tat atg agt      1251
Thr Val Ala Ile Gly Leu Ser Ser Gly Gly Ala Pro Gln Tyr Met Ser
        400                 405                 410 aag aat ctg tgg gtg gag cag tgg cag gat gga gta ctt cgg tta cgt      1299
Lys Asn Leu Trp Val Glu Gln Trp Gln Asp Gly Val Leu Arg Leu Arg
    415                 420                 425 gtt gag ggg ggt ggc tca att acg cac tca aac agt aag tgg cct gcc      1347
Val Glu Gly Gly Gly Ser Ile Thr His Ser Asn Ser Lys Trp Pro Ala
430                 435                 440                 445 atg acc gtt tcg tac ccg cgt agt ttc acg tga ggatcagacc accccgcggc    1400
Met Thr Val Ser Tyr Pro Arg Ser Phe Thr
            450                 455 actggggcat ttcatc                                                    1416

<210> SEQ ID NO 6
<211> LENGTH: 455
<212> TYPE: PRT
<213> ORGANISM: Mammalian orthoreovirus 3

<400> SEQUENCE: 6

Met Asp Pro Arg Leu Arg Glu Glu Val Val Arg Leu Ile Ile Ala Leu
1               5                   10                  15

Thr Ser Asp Asn Gly Ala Ser Leu Ser Lys Gly Leu Glu Ser Arg Val
            20                  25                  30

Ser Ala Leu Glu Lys Thr Ser Gln Ile His Ser Asp Thr Ile Leu Arg
        35                  40                  45

Ile Thr Gln Gly Leu Asp Asp Ala Asn Lys Arg Ile Ile Ala Leu Glu
    50                  55                  60

Gln Ser Arg Asp Asp Leu Val Ala Ser Val Ser Asp Ala Gln Leu Ala
65                  70                  75                  80

Ile Ser Arg Leu Glu Ser Ser Ile Gly Ala Leu Gln Thr Val Val Asn
                85                  90                  95

Gly Leu Asp Ser Ser Val Thr Gln Leu Gly Ala Arg Val Gly Gln Leu
            100                 105                 110

Glu Thr Gly Leu Ala Asp Val Arg Val Asp His Asp Asn Leu Val Ala
        115                 120                 125

Arg Val Asp Thr Ala Glu Arg Asn Ile Gly Ser Leu Thr Thr Glu Leu
    130                 135                 140

Ser Thr Leu Thr Leu Arg Val Thr Ser Ile Gln Ala Asp Phe Glu Ser
145                 150                 155                 160
```

```
Arg Ile Ser Thr Leu Glu Arg Thr Ala Val Thr Ser Ala Gly Ala Pro
                165                 170                 175

Leu Ser Ile Arg Asn Asn Arg Met Thr Met Gly Leu Asn Asp Gly Leu
            180                 185                 190

Thr Leu Ser Gly Asn Asn Leu Ala Ile Arg Leu Pro Gly Asn Thr Gly
        195                 200                 205

Leu Asn Ile Gln Asn Gly Gly Leu Gln Phe Arg Phe Asn Thr Asp Gln
    210                 215                 220

Phe Gln Ile Val Asn Asn Asn Leu Thr Leu Lys Thr Thr Val Phe Asp
225                 230                 235                 240

Ser Ile Asn Ser Arg Ile Gly Ala Thr Glu Gln Ser Tyr Val Ala Ser
                245                 250                 255

Ala Val Thr Pro Leu Arg Leu Asn Ser Ser Thr Lys Val Leu Asp Met
            260                 265                 270

Leu Ile Asp Ser Ser Thr Leu Glu Ile Asn Ser Ser Gly Gln Leu Thr
        275                 280                 285

Val Arg Ser Thr Ser Pro Asn Leu Arg Tyr Pro Ile Ala Asp Val Ser
    290                 295                 300

Gly Gly Ile Gly Met Ser Pro Asn Tyr Arg Phe Arg Gln Ser Met Trp
305                 310                 315                 320

Ile Gly Ile Val Ser Tyr Ser Gly Ser Gly Leu Asn Trp Arg Val Gln
                325                 330                 335

Val Asn Ser Asp Ile Phe Ile Val Asp Asp Tyr Ile His Ile Cys Leu
            340                 345                 350

Pro Ala Phe Asp Gly Phe Ser Ile Ala Asp Gly Asp Leu Ser Leu
        355                 360                 365

Asn Phe Val Thr Gly Leu Leu Pro Pro Leu Leu Thr Gly Asp Thr Glu
    370                 375                 380

Pro Ala Phe His Asn Asp Val Val Thr Tyr Gly Ala Gln Thr Val Ala
385                 390                 395                 400

Ile Gly Leu Ser Ser Gly Gly Ala Pro Gln Tyr Met Ser Lys Asn Leu
                405                 410                 415

Trp Val Glu Gln Trp Gln Asp Gly Val Leu Arg Leu Arg Val Glu Gly
            420                 425                 430

Gly Gly Ser Ile Thr His Ser Asn Ser Lys Trp Pro Ala Met Thr Val
        435                 440                 445

Ser Tyr Pro Arg Ser Phe Thr
    450                 455

<210> SEQ ID NO 7
<211> LENGTH: 1368
<212> TYPE: DNA
<213> ORGANISM: Reovirus sp.
<220> FEATURE:
<221> NAME/KEY: CDS
<222> LOCATION: (1)..(1368)

<400> SEQUENCE: 7 atg gat cct cgc cta cgt gaa gaa gta gta cgg ctg att atc gca tta      48
Met Asp Pro Arg Leu Arg Glu Glu Val Val Arg Leu Ile Ile Ala Leu
1               5                   10                  15 acg agt gat aat gga ata tca ctg tca aaa ggg ctt gaa tca agg gtc      96
Thr Ser Asp Asn Gly Ile Ser Leu Ser Lys Gly Leu Glu Ser Arg Val
            20                  25                  30 tcg gcg ctc gag aag acg tct caa ata cac tct gat act atc ctc cgg     144
Ser Ala Leu Glu Lys Thr Ser Gln Ile His Ser Asp Thr Ile Leu Arg
```

```
                       35                  40                  45
atc acc cag gga ctc gat gat gca aac aaa cga atc atc gct ctt gag        192
Ile Thr Gln Gly Leu Asp Asp Ala Asn Lys Arg Ile Ile Ala Leu Glu
 50                  55                  60 caa agt cgg gat gac ttg gtt gca tca gtc agt gat gct caa ctt gca        240
Gln Ser Arg Asp Asp Leu Val Ala Ser Val Ser Asp Ala Gln Leu Ala
 65                  70                  75                  80 atc tcc aga ttg gaa agc tct acc gga gcc ctc caa aca gtt gtc aat        288
Ile Ser Arg Leu Glu Ser Ser Thr Gly Ala Leu Gln Thr Val Val Asn
                 85                  90                  95 gga ctt gat tcg agt gtt acc cag ttg ggt gct cga gtg gga caa ctt        336
Gly Leu Asp Ser Ser Val Thr Gln Leu Gly Ala Arg Val Gly Gln Leu
            100                 105                 110 gag aca gga ctt gca gag cta cgc gtt gat cac gac aat ctc gtt gcg        384
Glu Thr Gly Leu Ala Glu Leu Arg Val Asp His Asp Asn Leu Val Ala
        115                 120                 125 aga gtg gat act gcg gaa cgt aac att gga tca ttg acc act gag cta        432
Arg Val Asp Thr Ala Glu Arg Asn Ile Gly Ser Leu Thr Thr Glu Leu
    130                 135                 140 tca act ctg acg tta cga gta aca tct ata caa gcg gat ttc gaa tct        480
Ser Thr Leu Thr Leu Arg Val Thr Ser Ile Gln Ala Asp Phe Glu Ser
145                 150                 155                 160 agg ata tcc aca tta gag cgc acg gcg gtc act agc gct gga gct ccc        528
Arg Ile Ser Thr Leu Glu Arg Thr Ala Val Thr Ser Ala Gly Ala Pro
                165                 170                 175 ctc tca atc cgt aat aac cgt atg acc atg gga tta aat gat gga ctt        576
Leu Ser Ile Arg Asn Asn Arg Met Thr Met Gly Leu Asn Asp Gly Leu
            180                 185                 190 acg ttg tca ggg aat aat ctc gcc att cgg ttg cca ggc aat acg ggt        624
Thr Leu Ser Gly Asn Asn Leu Ala Ile Arg Leu Pro Gly Asn Thr Gly
        195                 200                 205 ctg aat att caa aat ggt gga ctt cag ttt cga ttt aat act gat cag        672
Leu Asn Ile Gln Asn Gly Gly Leu Gln Phe Arg Phe Asn Thr Asp Gln
    210                 215                 220 ttc cag ata gtt aat aat aac ttg act ctc aag acg act gtg ttt gat        720
Phe Gln Ile Val Asn Asn Asn Leu Thr Leu Lys Thr Thr Val Phe Asp
225                 230                 235                 240 tct atc aac tca ggg ata ggc gca att gag caa agt tac gtg gcg tca        768
Ser Ile Asn Ser Gly Ile Gly Ala Ile Glu Gln Ser Tyr Val Ala Ser
                245                 250                 255 gca gtg act ccc ttg aga tta aac agt agc acg aag gtg ttg gat atg        816
Ala Val Thr Pro Leu Arg Leu Asn Ser Ser Thr Lys Val Leu Asp Met
            260                 265                 270 cta ata gac agt tca aca ctt gaa att aat tct agt gga cag cta act        864
Leu Ile Asp Ser Ser Thr Leu Glu Ile Asn Ser Ser Gly Gln Leu Thr
        275                 280                 285 gtt aga tcg aca tcc ccg aat ttg agg tat ccg ata gct gat gtt agc        912
Val Arg Ser Thr Ser Pro Asn Leu Arg Tyr Pro Ile Ala Asp Val Ser
    290                 295                 300 ggc ggt att gga atg agt cca aat tat agg ttt agg cag agc atg tgg        960
Gly Gly Ile Gly Met Ser Pro Asn Tyr Arg Phe Arg Gln Ser Met Trp
305                 310                 315                 320 ata gga att gtc tcc tat tct ggc agt ggg ctg aat tgg agg gta cag       1008
Ile Gly Ile Val Ser Tyr Ser Gly Ser Gly Leu Asn Trp Arg Val Gln
                325                 330                 335 gtg aac tcc gac att ttt att gta gat gat tac ata cat ata tgt ctt       1056
Val Asn Ser Asp Ile Phe Ile Val Asp Asp Tyr Ile His Ile Cys Leu
            340                 345                 350 cca gct ttt aac ggt ttc tct ata gct gac ggt gga gat cta tcg ttg       1104
Pro Ala Phe Asn Gly Phe Ser Ile Ala Asp Gly Gly Asp Leu Ser Leu
```

```
Pro Ala Phe Asn Gly Phe Ser Ile Ala Asp Gly Asp Leu Ser Leu
            355                 360                 365 aac ttt gtt acc gga tta tta cca ccg tta ctt acc gga gac act gag      1152
Asn Phe Val Thr Gly Leu Leu Pro Pro Leu Leu Thr Gly Asp Thr Glu
        370                 375                 380 ccc gct ttt cat aat gac gtg gtc aca tat gga gca cag act gta gct      1200
Pro Ala Phe His Asn Asp Val Val Thr Tyr Gly Ala Gln Thr Val Ala
385                 390                 395                 400 ata ggg ttg tcg tcg ggt ggt gcg cct cag tat atg agc aag aat ctg      1248
Ile Gly Leu Ser Ser Gly Gly Ala Pro Gln Tyr Met Ser Lys Asn Leu
                405                 410                 415 tgg gtg gag cag tgg cag gat gga gta ctt cgg tta cgt gtt gag ggg      1296
Trp Val Glu Gln Trp Gln Asp Gly Val Leu Arg Leu Arg Val Glu Gly
            420                 425                 430 ggt ggc tca att acg cac tca aac agt aag tgg cct gcc atg acc gtt      1344
Gly Gly Ser Ile Thr His Ser Asn Ser Lys Trp Pro Ala Met Thr Val
        435                 440                 445 tcg tac ccg cgt agt ttc acg tga                                      1368
Ser Tyr Pro Arg Ser Phe Thr
        450                 455

<210> SEQ ID NO 8
<211> LENGTH: 455
<212> TYPE: PRT
<213> ORGANISM: Reovirus sp.

<400> SEQUENCE: 8

Met Asp Pro Arg Leu Arg Glu Glu Val Val Arg Leu Ile Ile Ala Leu
1               5                   10                  15

Thr Ser Asp Asn Gly Ile Ser Leu Ser Lys Gly Leu Glu Ser Arg Val
            20                  25                  30

Ser Ala Leu Glu Lys Thr Ser Gln Ile His Ser Asp Thr Ile Leu Arg
        35                  40                  45

Ile Thr Gln Gly Leu Asp Asp Ala Asn Lys Arg Ile Ile Ala Leu Glu
    50                  55                  60

Gln Ser Arg Asp Asp Leu Val Ala Ser Val Ser Asp Ala Gln Leu Ala
65                  70                  75                  80

Ile Ser Arg Leu Glu Ser Ser Thr Gly Ala Leu Gln Thr Val Val Asn
                85                  90                  95

Gly Leu Asp Ser Ser Val Thr Gln Leu Gly Ala Arg Val Gly Gln Leu
            100                 105                 110

Glu Thr Gly Leu Ala Glu Leu Arg Val Asp His Asp Asn Leu Val Ala
        115                 120                 125

Arg Val Asp Thr Ala Glu Arg Asn Ile Gly Ser Leu Thr Thr Glu Leu
    130                 135                 140

Ser Thr Leu Thr Leu Arg Val Thr Ser Ile Gln Ala Asp Phe Glu Ser
145                 150                 155                 160

Arg Ile Ser Thr Leu Glu Arg Thr Ala Val Thr Ser Ala Gly Ala Pro
                165                 170                 175

Leu Ser Ile Arg Asn Asn Arg Met Thr Met Gly Leu Asn Asp Gly Leu
            180                 185                 190

Thr Leu Ser Gly Asn Asn Leu Ala Ile Arg Leu Pro Gly Asn Thr Gly
        195                 200                 205

Leu Asn Ile Gln Asn Gly Gly Leu Gln Phe Arg Phe Asn Thr Asp Gln
    210                 215                 220

Phe Gln Ile Val Asn Asn Asn Leu Thr Leu Lys Thr Thr Val Phe Asp
225                 230                 235                 240
```

```
Ser Ile Asn Ser Gly Ile Gly Ala Ile Glu Gln Ser Tyr Val Ala Ser
            245                 250                 255

Ala Val Thr Pro Leu Arg Leu Asn Ser Ser Thr Lys Val Leu Asp Met
        260                 265                 270

Leu Ile Asp Ser Ser Thr Leu Glu Ile Asn Ser Ser Gly Gln Leu Thr
            275                 280                 285

Val Arg Ser Thr Ser Pro Asn Leu Arg Tyr Pro Ile Ala Asp Val Ser
        290                 295                 300

Gly Gly Ile Gly Met Ser Pro Asn Tyr Arg Phe Arg Gln Ser Met Trp
305                 310                 315                 320

Ile Gly Ile Val Ser Tyr Ser Gly Ser Gly Leu Asn Trp Arg Val Gln
            325                 330                 335

Val Asn Ser Asp Ile Phe Ile Val Asp Asp Tyr Ile His Ile Cys Leu
        340                 345                 350

Pro Ala Phe Asn Gly Phe Ser Ile Ala Asp Gly Gly Asp Leu Ser Leu
            355                 360                 365

Asn Phe Val Thr Gly Leu Leu Pro Pro Leu Leu Thr Gly Asp Thr Glu
        370                 375                 380

Pro Ala Phe His Asn Asp Val Val Thr Tyr Gly Ala Gln Thr Val Ala
385                 390                 395                 400

Ile Gly Leu Ser Ser Gly Gly Ala Pro Gln Tyr Met Ser Lys Asn Leu
            405                 410                 415

Trp Val Glu Gln Trp Gln Asp Gly Val Leu Arg Leu Arg Val Glu Gly
        420                 425                 430

Gly Gly Ser Ile Thr His Ser Asn Ser Lys Trp Pro Ala Met Thr Val
            435                 440                 445

Ser Tyr Pro Arg Ser Phe Thr
        450                 455

<210> SEQ ID NO 9
<211> LENGTH: 1416
<212> TYPE: DNA
<213> ORGANISM: Reovirus 1

<400> SEQUENCE: 9
gctattggtc ggatggatcc tcgcctacgt gaagaagtag tacggctgat aatcgcatta      60
acgagtgata atgagcatc actgtcaaaa gggcttgaat caagggtctc ggcgctcgag      120
aagacgtctc aaatacactc tgatactatc ctccggatca cccagggact cgatgatgca     180
aacaaacgaa tcatcgctct tgagcaaagt cgggatgact tggttgcatc agtcagtgat     240
gctcaacttg caatctccag attggaaagc tctatcggag ccctccaaac agttgtcaat     300
ggacttgatt cgagtgttac ccagttgggt gctcgagtgg acaacttga dacaggactt     360 gcagacgtac gcgttgatca cgacaatctc gttgcgagag tggatactgc agaacgtaac     420
attggatcat tgaccactga gctatcaact ctgacgttac gagtaacatc catacaagcg     480
gatttcgaat ctaggatatc cacgttagag cgcacggcgg tcactagcgc gggagctccc     540
ctctcaatcc gtaataaccg tatgaccatg ggattaaatg atggactcac gttgtcaggg     600
aataatctcg ccatccgatt gccaggaaat acgggtctga atattcaaaa tggtggactt     660
cagtttcgat ttaatactga tcaattccag atagttaata taacttgac tctcaagacg      720 actgtgtttg attctatcaa ctcaaggata ggcgcaactg agcaaagtta cgtggcgtcg     780
gcagtgactc ccttgagatt aaacagtagc acgaaggtgc tggatatgct aatagacagt     840
```

-continued

```
tcaacacttg aaattaattc tagtggacag ctaactgtta gatcgacatc cccgaatttg    900
aggtatccga tagctgatgt tagcggcggt atcggaatga gtccaaatta taggtttagg    960
cagagcatgt ggataggaat tgtctcctat tctggtagtg ggctgaattg gagggtacag   1020
gtgaactccg acatttttat tgtagatgat tacatacata tatgtcttcc agcttttgac   1080
ggtttctcta tagctgacgg tggagatcta tcgttgaact ttgttaccgg attgttacca   1140
ccgttactta caggagacac tgagcccgct tttcataatg acgtggtcac atatggagca   1200
cagactgtag ctataggggtt gtcgtcgggt ggtgcgcctc agtatatgag taagaatctg   1260
tgggtggagc agtggcagga tggagtactt cggttacgtg ttgagggggg tggctcaatt   1320
acgcactcaa acagtaagtg gcctgccatg accgtttcgt acccgcgtag tttcacgtga   1380
ggatcagacc accccgcggc actggggcat ttcatc                             1416
```

<210> SEQ ID NO 10
<211> LENGTH: 1416
<212> TYPE: DNA
<213> ORGANISM: Reovirus 1

<400> SEQUENCE: 10

```
gctattggtc ggatggatcc tcgcctacgt gaagaagtag tacggctgat aatcgcatta     60
acgagtgata atggagcatc actgtcaaaa gggcttgaat caagggtctc ggcgctcgag    120
aagacgtctc aaatacactc tgatactatc ctccggatca cccagggact cgatgatgca    180
aacaaacgaa tcatcgctct tgagcaaagt cgggatgact tggttgcatc agtcagtgat    240
gctcaacttg caatctccag attggaaagc tctatcggag ccctccaaac agttgtcaat    300
ggacttgatt cgagtgttac ccagttgggt gctcgagtgg acaacttgga gacaggactt    360
gcagaggtac gcgttgatca cgacaatctc gttgcgagag tggatactgc agaacgtaac    420
attggatcat tgaccactga gctatcaact ctgacgttac gagtaacatc catacaagcg    480
gatttcgaat ctaggatatc cacgttagag cgcacggcgg tcactagcgc gggagctccc    540
ctctcaatcc gtaataaccg tatgaccatg ggattaaatg atggactcac gttgtcaggg    600
aataatctcg ccatccgatt gccaggaaat acgggtctga atattcaaaa tggtggactt    660
cagtttcgat ttaatactga tcaattccag atagttaata ataacttgac tctcaagacg    720
actgtgtttg attctatcaa ctcaaggata ggcgcaactg agcaaagtta cgtgcgtcg    780
gcagtgactc ccttgagatt aaacagtagc acgaaggtgc tggatatgct aatagacagt    840
tcaacacttg aaattaattc tagtggacag ctaactgtta gatcgacatc cccgaatttg    900
aggtatccga tagctgatgt tagcggcggt atcggaatga gtccaaatta taggtttagg    960
cagagcatgt ggataggaat tgtctcctat tctggtagtg ggctgaattg gagggtacag   1020
gtgaactccg acatttttat tgtagatgat tacatacata tatgtcttcc agcttttgac   1080
ggtttctcta tagctgacgg tggagatcta tcgttgaact ttgttaccgg attgttacca   1140
ccgttactta caggagacac tgagcccgct tttcataatg acgtggtcac atatggagca   1200
cagactgtag ctataggggtt gtcgtcgggt ggtgcgcctc agtatatgag taagaatctg   1260
tgggtggagc agtggcagga tggagtactt cggttacgtg ttgagggggg tggctcaatt   1320
acgcactcaa acagtaagtg gcctgccatg accgtttcgt acccgcgtag tttcacgtga   1380
ggatcagacc accccgcggc actggggcat ttcatc                             1416
```

<210> SEQ ID NO 11
<211> LENGTH: 1416

<212> TYPE: DNA
<213> ORGANISM: Reovirus 1

<400> SEQUENCE: 11

```
gctattggtc ggatggatcc tcgcctacgt gaagaagtag tacggctgat aatcgcatta      60
acgagtgata atggagcatc actgtcaaaa gggcttgaat caagggtctc ggcgctcgag     120
aagacgtctc aaatacactc tgatactatc ctccggatca cccagggact cgatgatgca     180
aacaaacgaa tcatcgctct tgagcaaagt cgggatgact tggttgcatc agtcagtgat     240
gctcaacttg caatctccag attggaaagc tctatcggag ccctccaaac agttgtcaat     300
ggacttgatt cgagtgttac ccagttgggt gctcgagtgg acaacttgga cacaggactt     360
gcagaggtac gcgttgatca cgacaatctc gctgcgagag tggatactgc agaacgtaac     420
attggatcat tgaccactga gctatcaact ctgacgttac gagtaacatc catacaagcg     480
gatttcgaat ctaggatatc cacgttagag cgcacggcgg tcactagcgc gggagctccc     540
ctctcaatcc gtaataaccg tatgaccatg ggattaaatg atggactcac gttgtcaggg     600
aataatctcg ccatccgatt gccaggaaat acgggtctga atattcaaaa tggtggactt     660
cagtttcgat ttaatactga tcaattccag atagttaata ataacttgac tctcaagacg     720
actgtgtttg attctatcaa ctcaaggata ggcgcaactg agtaaagtta cgtggcgtcg     780
gcagtgactc ccttgagatt aaacagtagc acgaaggtgc tggatatgct aatagacagt     840
tcaacacttg aaattaattc tagtggacag ctaactgtta gatcgacatc cccgaatttg     900
aggtatccga tggctgatgt tagcggcggt atcggaatga gtccaaatta taggtttagg     960
cagagcatgt ggataggaat tgtctcctat tctggtagtg ggctgaattg gagggtacag    1020
gtgaactccg acatttttat tgtagatgat tacatacata tatgtcttcc agcttttgac    1080
ggtttctcta tagctgacgg tggagatcta tcgttgaact ttgttaccgg attgttacca    1140
ccgttactta caggagacac tgagcccgct tttcataatg acgtggtcac atatggagca    1200
cagactgtag ctataggggtt gtcgtcgggt ggtgcgcctc agtatatgag taagaatctg    1260
tgggtggagc agtggcagga tggagtactt cggttacgtg ttgaggggggg tggctcaatt    1320
acgcactcaa acagtaagtg gcctgccatg accgtttcgt acccgcgtag tttcacgtga    1380
ggatcagacc accccgcggc actggggcat ttcatc                              1416
```

<210> SEQ ID NO 12
<211> LENGTH: 1340
<212> TYPE: DNA
<213> ORGANISM: Mammalian orthoreovirus 3

<400> SEQUENCE: 12

```
atggatcctc gccacgttaa gaagtagtac ggctgataat cgcattaacg agtgataatg      60
gagcatcact gtcaaaaggg cttgaatcaa gggtctcggc gctcgagaag acgtctcaaa     120
tacactctga tactatcctc cggatcaccc agggactcga tgatgcaaac aaacgaatca     180
tcgctcttga gcaaagtcgg gatgacttgg ttgcatcagt cagtgatgct caacttgcaa     240
tctccagatt ggaaagctct atcggagccc tccaaacagt tgtcaatgga cttgattcga     300
gtgttaccca gttgggtgct cgagtggaca acttgagac aggacctgca gagctacgcg     360
ttgatcacga caatctcgct gcgagagtgg atactgcaga acgtaacatt ggatcattga     420
ccactgagct atcaactctg acgttacgag taacatccat acaagcggat ttcgaatcta     480
ggatatccac gttagagcgc acggcggtca ctagcgcggg agctcccctc tcaatccgta     540
```

```
ataaccgtat gaccatggga ttaaatgatg gactcacgtt gtcagggaat aatctcgcca    600
tccgattgcc aggaaatacg ggtctgaata ttcaaaatgg tggacttcag tttcgattta    660
atactgatca attccagata gttaataata acttgactct caagacgact gtgtttgatt    720
ctatcaactc aaggataggc gcaactgagt aaagttacgt ggcgtcggca gtgactccct    780
tgagattaaa cagtagcacg aaggtgctgg atatgctaat agacagttca acacttgaaa    840
ttaattctag tggacagcta actgttagat cgacatcccc gaatttgagg tatccgatgg    900
ctgatgttag cggcggtatc ggaatgagtc caaattatag gtttaggcag agcatgtgga    960
taggaattgt ctcctattct ggtagtgggc tgaattggag ggtacaggtg aactccgaca   1020
tttttattgt agatgattac atacatatat gtcttccagc ttttgacggt ttctctatag   1080
ctgacggtgg agatctatcg ttgaactttg ttaccggatt gttaccaccg ttacttacag   1140
gagacactga gcccgctttt cataatgacg tggtcacata tggagcacag actgtagcta   1200
tagggttgtc gtcgggtggt gcgcctcagt atatgagtaa gaatctgtgg gtggagcagt   1260
ggcaggatgg agtacttcgg ttacgtgttg agggggtgg ctcaattacg cactcaaaca   1320
gtaagtggcc tgccatgacc                                               1340
```

<210> SEQ ID NO 13
<211> LENGTH: 1196
<212> TYPE: DNA
<213> ORGANISM: Mammalian orthoreovirus 3

<400> SEQUENCE: 13

```
gctattttg cctcttccca gacgttgtcg caatggaggt gtgcttgccc aacggtcatc     60
aggtcgtgga cttgattaac aacgcttttg aaggtcgtgt atcaatctac agcgcgcaag    120
agggatggga caaacaatc tcagcacagc cagatatgat ggtatgtggt ggcgccgtcg    180
tttgcatgca ttgtctaggt gttgttggat ctctacaacg caagctgaag catttgcctc    240
accatagatg taatcaacag atccgtcatc aggattacgt cgatgtacag ttcgcagacc    300
gtgttactgc tcactggaag cggggtatgc tgtccttcgt tgcgcagatg cacgagatga    360
tgaatgacgt gtcgccagat gacctggatc gtgtgcgtac tgagggaggt tcactagtgg    420
agctgaaccg gcttcaggtt gacccaaatt caatgtttag atcaatacac tcaagttgga    480
cagatccttt gcaggtggtg gacgaccttg acactaagct ggatcagtac tggacagcct    540
taaacctgat gatcgactca tccgacttga tacccaactt tatgatgaga gacccatcac    600
acgcgttcaa tggtgtgaaa ctggaggagg atgctcgtca aacccaattc tccaggactt    660
ttgattcgag atcgagtttg gaatgggggtg tgatggttta tgattactct gagctggagc    720
atgatccatc gaagggccgt gcttacagaa aggaattggt gacgccagct cgagatttcg    780
gtcactttgg attatcccat tattctaggg cgactacccc aatccttgga agatgccgg    840 ccgtattctc aggaatgttg actgggaact gtaaaatgta tccattcatt aaaggaacgg    900
ctaagctgaa gacagtgcgc aagctagtgg aagcagtcaa tcatgcttgg ggtgtcgaga    960
agattagata tgctcttggg ccaggtggca tgacgggatg gtacaatagg actatgcaac   1020
aggcccccat tgtgctaact cctgctgctc tcacaatgtt cccagatacc atcaagtttg   1080
gggatttgaa ttatccagtg atgattggcg atccgatgat tcttggctaa acaccccat   1140 cttcacagcg ccgggcttga ccaacctggt gtgacgtggg acaggcttca ttcatc       1196
```

<210> SEQ ID NO 14
<211> LENGTH: 1196

<212> TYPE: DNA
<213> ORGANISM: Mammalian orthoreovirus 3

<400> SEQUENCE: 14

```
gctattttg cctcttccca gacgttgtcg caatggaggt gtgcttgccc aacggtcatc    60
aggtcgtgga cttgattaac aacgcttttg aaggtcgtgt atcaatctac agcgcgcaag   120
agggatggga caaaacaatc tcagcacagc cagatatgat ggtatgtggt ggcgccgtcg   180
tttgcatgca ttgtctaggt gttgttggat ctctacaacg caagctgaag catttgcctc   240
accatagatg taatcaacag atccgtcatc aggattacgt cgatgtacag ttcgcagacc   300
gtgttactgc tcactggaag cggggtatgc tgtccttcgt tgcgcagatg cacgagatga   360
tgaatgacgt gtcgccagat gacctggatc gtgtgcgtac tgagggaggt tcactagtgg   420
agctgaaccg gcttcaggtt gacccaaatt caatgtttag atcaatacac tcaagttgga   480
cagatccttt gcaggtggtg gacgaccttg acactaagct ggatcagtac tggacagcct   540
taaacctgat gatcgactca tccgacttga tacccaactt tatgatgaga gacccatcac   600
acgcgttcaa tggtgtgaaa ctgaagggag atgctcgtca acccaattc tccaggactt   660
ttgattcgag atcgagtttg gaatggggtg tgatggttta tgattactct gagctggatc   720
atgatccatc gaagggccgt gcttacagaa aggaattggt gacgccagct cgagatttcg   780
gtcactttgg attatcccat tattctaggg cgactacccc aatccttgga agatgccgg    840
ccgtattctc aggaatgttg actgggaact gtaaaatgta tccattcatt aaaggaacgg   900
ctaagctgaa gacagtgcgc aagctagtgg aggcagtcaa tcatgcttgg ggtgtcgaga   960
agattagata tgctcttggg ccaggtggca tgacgggatg gtacaatagg actatgcaac   1020
aggcccccat tgtgctaact cctgctgctc tcacaatgtt cccagatacc atcaagtttg   1080
gggatttgaa ttatccagtg atgattggcg atccgatgat tcttggctaa acaccccat    1140
cttcacagcg ccgggcttga ccaacctggt gtgacgtggg acaggcttca ttcatc       1196
```

<210> SEQ ID NO 15
<211> LENGTH: 1196
<212> TYPE: DNA
<213> ORGANISM: Mammalian orthoreovirus 3

<400> SEQUENCE: 15

```
gctattttg cctcttccca gacgttgtcg caatggaggt gtgcttgccc aacggtcatc    60
aggtcgtgga cttgattaac aacgcttttg aaggtcgtgt atcaatctac agcgcgcaag   120
agggatggga caaaacaatc tcagcacagc cagatatgat ggtatgtggt ggcgccgtcg   180
tttgcatgca ttgtctaggt gttgttggat ctctacaacg caagctgaag catttgcctc   240
accatagatg taatcaacag atccgtcatc aggattacgt cgatgtacag ttcgcagacc   300
gtgttactgc tcactggaag cggggtatgc tgtccttcgt tgcgcagatg cacgagatga   360
tgaatgacgt gtcgccagat gacctggatc gtgtgcgtac tgagggaggt tcactagtgg   420
agctgaaccg gcttcaggtt gacccaaatt caatgtttag atcaatacac tcaagttgga   480
cagatccttt gcaggtggtg gacgaccttg acactaagct ggatcagtac tggacagcct   540
taaacctgat gatcgactca ttcgacttga tacccaactt tatgatgaga gacccatcac   600
acgcgttcaa tggtgtgaaa ctgaagggag atgctcgtca acccaattc tccaggactt    660
ttgattcgag atcgagtttg gaatggggtg tgatggttta tgattactct gagctggatc   720
atgatccatc gaagggccgt gcttacagaa aggaattggt gacgccagct cgagatttcg   780
```

```
gtctctttgg attatcccat tattctaggg cgactacccc aatccttgga aagatgccgg      840
ccgtattctc aggaatgttg actgggaact gtaaaatgta tccattcatt aaaggaacgg      900
ctaagctgaa gacagtgcgc aagctagtgg aggcagtcaa tcatgcttgg ggtgtcgaga      960
agattagata tgctcttggg ccaggtggca tgacgggatg gtacaatagg actatgcaac     1020
aggcccccat tgtgctaact cctgctgctc tcacaatgtt cccagatacc atcaagtttg     1080
gggatttgaa ttatccagtg atgattggcg atccgatgat tcttggctaa acacccccat     1140
cttcacagcg ccgggcttga ccaacctggt gtgacgtggg acaggcttca ttcatc         1196
```

<210> SEQ ID NO 16  
<211> LENGTH: 4  
<212> TYPE: PRT  
<213> ORGANISM: Artificial Sequence  
<220> FEATURE:  
<223> OTHER INFORMATION: Description of Artificial Sequence: Synthetic Peptide

<400> SEQUENCE: 16

Tyr Val Ala Asp  
1

<210> SEQ ID NO 17  
<211> LENGTH: 20  
<212> TYPE: DNA  
<213> ORGANISM: Artificial Sequence  
<220> FEATURE:  
<223> OTHER INFORMATION: Description of Artificial Sequence: Synthetic Primer

<400> SEQUENCE: 17
ggtgaaacct gtttgttgga                                                    20

<210> SEQ ID NO 18  
<211> LENGTH: 20  
<212> TYPE: DNA  
<213> ORGANISM: Artificial Sequence  
<220> FEATURE:  
<223> OTHER INFORMATION: Description of Artificial Sequence: Synthetic Primer

<400> SEQUENCE: 18
atacacagag gaagccttcg                                                    20

<210> SEQ ID NO 19  
<211> LENGTH: 34  
<212> TYPE: DNA  
<213> ORGANISM: Artificial Sequence  
<220> FEATURE:  
<223> OTHER INFORMATION: Description of Artificial Sequence: Synthetic Primer

<400> SEQUENCE: 19
catgaattca tggatcctcg cctacgttaa gaag                                    34

<210> SEQ ID NO 20  
<211> LENGTH: 32  
<212> TYPE: DNA  
<213> ORGANISM: Artificial Sequence  
<220> FEATURE:  
<223> OTHER INFORMATION: Description of Artificial Sequence: Synthetic Primer

<400> SEQUENCE: 20
cagaagcttc tgatcctcac gtgaaactac gc                                      32

```
<210> SEQ ID NO 21
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
aattcgattt aggtgacact atagctattg gtcggatg                              38

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
cccttttgac agtgatgctc cgttatcact cg                                    32

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
cggagtcaac ggatttggtc gtat                                             24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
agccttctcc atggtggtga agac                                             24
```